US007151097B2

(12) United States Patent
Carpino et al.

(10) Patent No.: US 7,151,097 B2
(45) Date of Patent: Dec. 19, 2006

(54) BICYCLIC PYRAZOLYL AND IMIDAZOLYL COMPOUNDS AND USES THEREOF

(75) Inventors: Philip A. Carpino, Groton, CT (US); Robert L. Dow, Waterford, CT (US); David A. Griffith, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 210 days.

(21) Appl. No.: 10/971,599

(22) Filed: Oct. 22, 2004

(65) Prior Publication Data

US 2005/0101592 A1 May 12, 2005

Related U.S. Application Data

(60) Provisional application No. 60/518,280, filed on Nov. 7, 2003.

(51) Int. Cl.
*C07D 267/02* (2006.01)
*C07D 487/02* (2006.01)
*C07D 491/00* (2006.01)
*A61K 31/55* (2006.01)
*A61P 25/30* (2006.01)

(52) U.S. Cl. ................. 514/211.05; 514/220; 514/221; 540/490; 540/497; 540/498; 540/502

(58) Field of Classification Search ................ 540/490, 540/497, 498, 502; 514/211.05, 220, 221
See application file for complete search history.

(56) References Cited

U.S. PATENT DOCUMENTS

| | | | |
|---|---|---|---|
| 2004/0077650 A1 | 4/2004 | Dow | 514/242 |
| 2004/0092520 A1 | 5/2004 | Griffith | 514/242 |
| 2004/0122074 A1 | 6/2004 | Dow et al. | 514/397 |
| 2004/0157838 A1 | 8/2004 | Griffith | 514/227.8 |
| 2004/0157839 A1 | 8/2004 | Griffith | 514/227.8 |
| 2004/0214837 A1 | 10/2004 | Griffith et al. | 514/262.1 |
| 2004/0214838 A1 | 10/2004 | Carpino et al. | 514/262.1 |
| 2004/0214855 A1 | 10/2004 | Carpino et al. | 514/303 |
| 2004/0214856 A1 | 10/2004 | Carpino et al. | 514/303 |
| 2004/0224970 A1 | 11/2004 | Smith et al. | |
| 2004/0235926 A1 | 11/2004 | Sakya | 514/406 |
| 2004/0248881 A1 | 12/2004 | Carpino et al. | 514/217.05 |
| 2004/0259887 A1 | 12/2004 | Dow | 514/256 |
| 2005/0026983 A1 | 2/2005 | Carpino | 514/397 |

FOREIGN PATENT DOCUMENTS

| | | |
|---|---|---|
| WO | WO 0158869 | 2/2001 |
| WO | WO 03020217 | 8/2002 |
| WO | WO 03027114 | 9/2002 |
| WO | WO 03080609 | 3/2003 |
| WO | WO 04094421 | 4/2004 |
| WO | WO 04094429 | 4/2004 |
| WO | WO 04098520 | 4/2004 |

OTHER PUBLICATIONS

Pertwee, Roger, *Exp. Opin. Invest. Drugs,* "Cannabinoid Receptor Ligands: Clinical and Neuropharmacological Considerations, Relevant to Future Drug Discovery and Development", vol. 9(7), pp. 1553-1571 (2000).

Glushkov, R., et al. *Study of Lactams,* "Reaction of 2, 3-Dioxo-4-(N,N-Dimethylaminomethylene) Hexahydroazepine with Hydrazine and its Derivatitves", vol. 9, pp. 1248-1251 (1978).

Beardsley, P.M., et al., *Behavioural Pharmacology,* "Current Evidence Supporting a Role of Cannabinold CB1 Receptor (CB1R) Antagonists as Potential Pharmacotherapies for Drug Abuse Disorders", vol. 16, pp. 275-296 (2005).

Bermudez-Siva, F., et al., *Journal of Pharmacology,* "Activation of Cannabinoid CB1 Receptors Induces Glucose Intolerance in Rats", vol. 531, pp. 282-284 (2006).

Brittain. H.G., *Drugs and the Pharmaceutical Sciences,* "Polymorphism in Pharmaceutical Solids", vol. 95, pp. 202-207 (1999).

Brodie, B.B., *Life Sciences,* "Rimonabant: The First Therapeutically Relevant Cannabinold Antagonist", vol. 77, pp. 2339-2350 (2005).

Cao, X, et al., A Selective Cannabinoid CB1 Antagonist Increases Levodopa Responses in Parkinsonlan Monkeys.

Chambers, A.P., et al., *Physiology & Behavior,* "Cannabinoid (CB1) Receptor Antagonist, AM 251, causes a Sustained Reduction of Daily Food Intake in the Rat", vol. 82, pp. 863-869 (2004).

Chaperon, F., et al., *Psychopharmacology,* "Involvement of Central Cannabinoid (CB1) Receptors in the Establishment of Place Conditioning in Rats", vol. 135, pp. 324-332 (198).

(Continued)

*Primary Examiner*—Bruck Kifle
(74) *Attorney, Agent, or Firm*—Gregg C. Benson; Arlene K. Musser

(57) ABSTRACT

Compounds of Formula (I) are described herein.

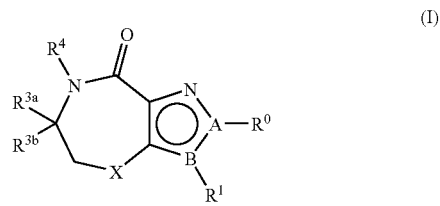

(I)

The compounds have been shown to act as cannabinoid receptor ligands and are therefore useful in the treatment of diseases linked to the mediation of the cannabinoid receptors in animals.

182 Claims, No Drawings

OTHER PUBLICATIONS

Cohen, C., et al., *Behavioural Pharmacology*, SR141716, A Central Cannabinoid (CBI) Receptor Antagonist, Blocks the Motivational and Dopamine-Releasing Effects of Nicotine in Rats, vol. 13, pp. 451-463 (2002).

Croci, T., et al., *British Journal of Pharmacology*, "Role of Cannabinoid CB1 Receptors and Tumor Necrosis Factor—αin the Gut and Systemic Anti-Inflammatory Activity of SR 141716 (Rimonabant) in Rodents", vol. 140, pp. 115-122 (2003).

De Vries, T.J., et al., *Trends in Pharmacological Sciences*, "Cannabinoid CB1 Receptors Control Conditioned Drug Seeking", vol. 26 No. 8, pp. 420-426 (2005).

Di Marzo, V., *TRENDS in Pharmacological Sciences*, "A Brief History of Cannabinoid and Endocannabinoid Pharmacology as Inspired by the Work of British Scientists", vol. 20 No. 20 pp. 1-7 (2006).

Di Marzo, V., et al., *The FASEB Journal*, "Enhanced Levels of Endogenous Cannabinoids in the Globus Pallidus are Associated with a Reduction in Movement in an Animal Model of Parkinson's Disease", vol. 14, pp. 1432-1438 (2000).

Fernandez, J.R., et al., *Current Opinion in Investigational Drugs*, "Rimonabant Sanofl-Synthelabo", vol. 5, No. 4, pp. 430-435 (2004).

Ferrer, B., et al., *European Journal of Neuroscience*, "Effects of Levodopa on Endocannabinoid Levels in Rat Basal Ganglia": Implications for the Treatment of Levodopa-Induced Dyskinesias, vol. 18, pp. 1607-1614 (2003).

Griebel, G., et al., *Biol. Psychiatry*, Effects of the Cannabinoid CB1 Receptor antagonist Rimonabant In Models of Emotional.

Lange, J., et al., *Drug Discovery Today* "Medicinal Chemistry Strategies to CB1 Cannabinoid Receptor Antagonists", vol. 10, No. 10, pp. 693-702 (2005).

Le Foll, B., et al., *NeuroReport*, "Reimonabant, a CB1 Antagonist, Blocks Nicotine-Conditioned Place Preferences", vol. 15, No. 13, pp. 2139-2143 (2004).

Mansbach, R.S., et al., *Psychopharmacology*, "Effects of the Cannabinoid CB1 Receptor Antagonist SR141716A on the Behaviour of Pigeons and Rats", vol. 124, pp. 315-322 (1996).

Mas-Nieto, M., et al., *British Journal of Pharmacology*, "Reduction of Opioid Dependence by the CB1 antagonist SR141716A in Mice: Evaluation of the Interest in Pharmacology of Opioid Addiction", vol. 132, pp. 1809-1816 (2001).

Mechoulam, R., et al., *TRENDS in Pharmacological Sciences*, "Cannabis and Alcohol—A Close Friendship", vol. 24, No. 6, pp. 266-268 (2003).

Muccloli, G.G., et al., *Current Medicinal Chemistry*, "Current Knowledge on the Antagonists and Inverse Agonists of Cannabinoid Receptors", vol. 12, pp. 1361-1394 (2005).

Pagotto, U., et al., *Endocrine Reviews*, "The Emerging Role of the Endocannabinoid System in Endocrine Regulation and Energy Balance", vol. 27, No. 1, pp. 73-100 (2006).

Pagotto, U., et al., *Current Opinion in Endocrinology & Diabetes*, "the Role of the Endocannabinoid Pathway in Metabolism and Diabetes", vol. 13, pp. 171-178 (2006).

Poncelet, M., et al., *Psychopharmacology*, "Blockade of Cannabinoid (CB1) Receptors By SR 141716 Selectively Antagonizes Drug-Induced Reinstatement of Exploratory Behaviour in Gerbils", vol. 144, pp. 144-150 (1999).

Sanudo-Pena, M., et al, *Neuroscience Letters*, "Endogenous Cannabinoids As an Aversive or Counter-Rewarding System in the Rat", vol. 223, pp. 125-128 (1997).

Smith, R.A., et al., *IDrugs*, "Recent Advances in the Research and Development of CB1 Antagonists", vol. 8, No. 1, pp. 53-66 (2005).

Thakur, G.A., et al., *Mini-Reviews in Medicinal Chemistry*, "CB1 Cannabinoid Receptor Ligands", vol. 5, pp. 631-640 (2005).

Van Der Stell, M., et al., *The FASEB Journal*, "A Role For Endocannabinoids in the Generation of Parkinsonism and Levodopa-Induced Dyskinesia in MPTP-Lesioned Non-Human Primate Models of Parkinson's Disease", vol. 19, pp. 1140-1142 (2005).

Van Gaal, L., et al., *Lancet*, "Effects of the Cannabinoid-1 Receptor Blocker Rimonabant on Weight Reduction and Cardiovascular Risk Factors in Overweight Patients: 1-year Experience from the RIO-Europe Study", vol. 365, pp. 1389-1397 (2005).

Witkin, J.M., et al., *TRENDS in Pharmacological Sciences*, "A Therapeutic Role for Cannabinoid CB1 Receptor Antagonists in Major Depressive Disorders", vol. 26, No. 12, pp. 609-617 (2005).

Wolff, M., et al., *European Journal of Pharmcology*, "SR141716A, A Cannabinoid CB1 Receptor Antagonist, Improves Memory in a Delayed Radial Maze Task", vol. 477, pp. 213-217 (2003).

Louis, C., et al., *Psychopharmacology*, "Surinabant, a New CB1 Receptor Antagonist, Displays Efficacy in Animal Models of Attention Deficit/Hyperactivity Disorder", vol. 30, S173, Abstract 77 (2005).

BICYCLIC PYRAZOLYL AND IMIDAZOLYL COMPOUNDS AND USES THEREOF

This patent application claims the benefit of U.S. Provisional Patent Application Ser. No. 60/518,280 filed on Nov. 7, 2003 and incorporated herein by reference in its entirety.

FIELD OF THE INVENTION

The present invention relates to bicyclic pyrazolyl and imidazolyl compounds. The compounds have been found to be cannabinoid receptor ligands, in particular CB1 receptor antagonists, and are therefore useful for treating diseases, conditions and/or disorders modulated by cannabinoid receptor antagonists.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25–29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207–12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5–10% loss of body weight can substantially improve metabolic values, such as blood glucose, blood pressure, and lipid concentrations. Hence, it is believed that a 5–10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," *Obes Res.*, 3(suppl 4), 415s–7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., "Selective Inhibition of Sucrose and Ethanol Intake by SR141716, an Antagonist of Central Cannabinoid (CB1) Receptors," *Psychopharmacol*, 132, 104–106 (1997); Colombo, G., et al., "Appetite Suppression and Weight Loss after the Cannabinoid Antagonist SR141716," *Life Sci.*, 63, PL113-PL117 (1998); Simiand, J., et al., "SR141716, a CB1 Cannabinoid Receptor Antagonist, Selectively Reduces Sweet Food Intake in Marmose," *Behav. Pharmacol.*, 9, 179–181 (1998); and Chaperon, F., et al., "Involvement of Central Cannabinoid (CB1) Receptors in the Establishment of Place Conditioning in Rats," *Psychopharmacology*, 135, 324–332 (1998). For a review of cannabinoid CB1 and CB2 receptor modulators, see Pertwee, R. G., "Cannabinoid Receptor Ligands: Clinical and Neuropharmacological Considerations, Relevant to Future Drug Discovery and Development," *Exp. Opin. Invest. Drugs*, 9(7), 1553–1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., "Selective Inhibition of Sucrose and Ethanol Intake by SR141716, an Antagonist of Central Cannabinoid (CB1) Receptors," *Psychopharmacol*, 132, 104–106 (1997). For a review, see Hungund, B. L and B. S. Basavarajappa, "Are Anadamide and Cannabinoid Receptors involved in Ethanol Tolerance? A Review of the Evidence," *Alcohol & Alcoholism.* 35(2) 126–133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I):

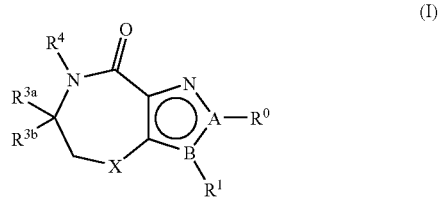

wherein

A is nitrogen and B is carbon, or A is carbon and B is nitrogen;

$R^0$ is an aryl optionally substituted with one or more substituents, or a heteroaryl optionally substituted with one or more substituents;

$R^1$ is aryl optionally substituted with one or more substituents, heteroaryl optionally substituted with one or more substituents, —CH=CH—$R^{1a}$, or —CH$_2$CH$_2$—$R^{1a}$, where $R^{1a}$ is hydrogen or a chemical moiety selected from ($C_1$–$C_8$) alkyl, 3- to 8-membered partially or fully saturated carbocyclic ring(s), 3- to 6-membered partially or fully saturated heterocycle, aryl, heteroaryl, where the chemical moiety is optionally substituted with one or more substituents;

X is O, S, SO, SO$_2$, —N($R^{2a}$)— or —C($R^{2b}$)($R^{2c}$)—, where $R^{2a}$, $R^{2b}$ and $R^{2c}$ are each independently hydrogen, ($C_1$–$C_4$)alkyl, halo-substituted ($C_1$–$C_4$)alkyl or ($C_1$–$C_5$) acyl; (preferably, $R^{2a}$ is hydrogen, ($C_1$–$C_4$)alkyl, or fluoro-substituted ($C_1$–$C_4$)alkyl); and at least one of $R^{2b}$ and $R^{2c}$ is ($C_1$–$C_4$)alkyl or fluoro-substituted ($C_1$–$C_4$)alkyl, or both $R^{2b}$ and $R^{2c}$ are hydrogen);

$R^{3a}$ and $R^{3b}$ are each independently hydrogen, ($C_1$–$C_6$) alkyl, or halo-substituted ($C_1$–$C_6$)alkyl (preferably, $R^{3a}$ and $R^{3b}$ are each independently hydrogen, ($C_1$–$C_4$)alkyl, or fluoro-substituted ($C_1$–$C_4$)alkyl), or either $R^{3a}$ or $R^{3b}$ taken together with $R^4$ forms a fully or partially saturated 5- to 6-membered heterocyclic ring, where the heterocyclic ring optionally contains an additional heteroatom selected from oxygen, nitrogen or sulfur and is optionally substituted with one or more substituents; and $R^4$ is a chemical moiety selected from the group consisting of ($C_1$–$C_8$)alkyl, aryl, heteroaryl, aryl($C_1$–$C_4$)alkyl, a 3- to 8-membered partially or fully saturated carbocyclic ring(s), heteroaryl($C_1$–$C_3$)alkyl, 5–6 membered lactone, 5- to 6-membered lactam, and a 3- to 8-membered partially or fully saturated heterocycle, where said chemical moiety is optionally substituted with one or more substituents, or $R^4$ taken together with either $R^{3a}$ or $R^{3b}$ forms a fully or partially saturated 5- to 6-membered heterocyclic ring, where the heterocyclic ring optionally contains an additional heteroatom selected from oxygen, nitrogen or sulfur and is optionally substituted with one or more substituents;

a pharmaceutically acceptable salt thereof, a prodrug of the compound or the salt, or a solvate or hydrate of the compound, the salt or the prodrug.

Preferably, $R^0$ and $R^1$ are each independently a substituted phenyl. More preferably, $R^0$ and $R^1$ are each independently a phenyl substituted with one to three substituents independently selected from the group consisting of halo (preferably, chloro or fluoro), ($C_1$–$C_4$)alkoxy, ($C_1$–$C_4$)alkyl, halo-substituted ($C_1$–$C_4$)alkyl (preferably fluoro-substituted alkyl, more preferably, trifluoromethyl) and cyano. Most preferably, $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl.

Preferably, $R^4$ is a chemical moiety selected from the group consisting of ($C_1$–$C_8$)alkyl, aryl($C_1$–$C_4$)alkyl, 3- to 8-membered partially or fully saturated carbocyclic ring(s), and 3- to 8-membered partially or fully saturated heterocycle, where said chemical moiety is optionally substituted with one or more substituents.or $R^4$ taken together with either $R^{3a}$ or $R^{3b}$ forms a fully or partially saturated 5- to 6-membered heterocyclic ring, where said heterocyclic ring is optionally substituted with one or more substituents. More preferably, $R^4$ is ($C_1$–$C_8$)alkyl, halo-substituted ($C_1$–$C_8$) alkyl (preferably, fluoro-substituted ($C_1$–$C_8$)alkyl), cyclopentyl, cyclohexyl, piperidin-1-yl, pyrrolidin-1-yl, or morpholin-1-yl.

In a preferred embodiment of the present invention, a compound of Formula (II) is provided:

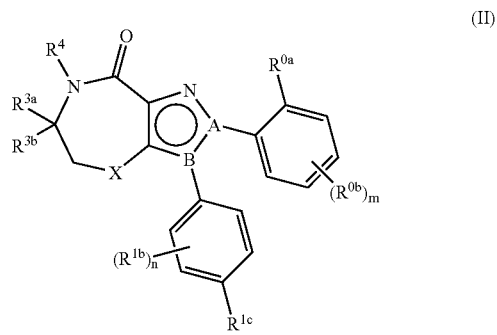

(II)

wherein

A, B, X, $R^{2a}$, $R^{2b}$, $R^{2c}$, $R^{3a}$, $R^{3b}$, and $R^4$ are as defined above (preferred groups are also defined above);

$R^{0a}$, $R^{0b}$, $R^{1b}$, and $R^{1c}$ are each independently halo, ($C_1$–$C_4$)alkoxy, ($C_1$–$C_4$)alkyl, halo-substituted ($C_1$–$C_4$) alkyl, or cyano (preferably, $R^{0a}$ is chloro, fluoro, or methyl; $R^{0b}$ is chloro, fluoro or hydrogen (i.e., m is 0); $R^{1c}$ is chloro, fluoro, ($C_1$–$C_4$)alkyl, trifluoromethyl, ($C_1$–$C_4$)alkoxy, or cyano; and $R^{1b}$ is hydrogen (i.e., n is 0));

n and m are each independently 0, 1 or 2;

a pharmaceutically acceptable salt thereof, a prodrug of the compound or the salt, or a solvate or hydrate of the compound, the salt or the prodrug.

Preferred compounds of the present invention include:
3-(4-chlorophenyl)-2-(2-chlorophenyl)-7-(2,2,2-trifluoroethyl)-6,7-dihydro-2H,5H-4-oxa-1,2,7-triaza-azulen-8-one;
3-(4-chlorophenyl)-2-(2-chlorophenyl)-7-(2,2-difluoropropyl)-6,7-dihydro-2H,5H-4-oxa-1,2,7-triaza-azulen-8-one;
3-(4-chloro-phenyl)-2-(2-chloro-phenyl)-7-(2,2-difluorobutyl)-6,7-dihydro-2H,5H-4-oxa-1,2,7-triaza-azulen-8-one;
3-(4-chloro-phenyl)-2-(2-chloro-phenyl)-7-isopropyl-6,7-dihydro-2H,5H-4-oxa-1,2,7-triaza-azulen-8-one; 3-(4-chlorophenyl)-2-(2-chlorophenyl)-7-(2,2,2-trifluoroethyl)-4,5,6,7-tetrahydro-2H-pyrazolo[4,3-e][1,4]diazepin-8-one; 1-(4-chlorophenyl)-2-(2-chlorophenyl)-5,6,7,7a,8,9-hexahydro-2H-2,3,4a,9-tetraazacyclopenta[f]azulen-4-one; 3-(4-chlorophenyl)-2-(2-chlorophenyl)-7-(2,2,2-trifluoroethyl)-4,5,6,7-tetrahydro-2H-pyrazolo[4,3-e][1,4]diazepin-8-one;
3-(4-chlorophenyl)-2-(2-chlorophenyl)-6,6-dimethyl-7-(2,2,2-trifluoroethyl)-4,5,6,7-tetrahydro-2H-pyrazolo[4,3-e][1,4]diazepin-8one; 2-(2-chlorophenyl)-1-(4-chlorophenyl)-2,5,6,7,8,8a,9,10-octahydro-2,3,4a,10-tetraazabenzo[f]azulen-4-one; 3-(4-chlorophenyl)-2-(2-chlorophenyl)-4,6,6-trimethyl-7-(2,2,2-trifluoroethyl)-4,5,6,7-tetrahydro-2H-pyrazolo[4,3-e][1,4]diazepin-8-one; 2-(2-chlorophenyl)-1-(4-chlorophenyl)-9-methyl-5,6,7,7a,8,9-hexahydro-2H-2,3,4a,9-tetraazacyclopenta[f]azulen-4-one; 3-(4-chlorophenyl)-2-(2-chlorophenyl)-4-methyl-7-(2,2,2-trifluoroethyl)-4,5,6,7-tetrahydro-2H-pyrazolo[4,3-e][1,4]diazepin-8-one; 3-(4-chlorophenyl)-2-(2-chlorophenyl)-7-(2,2,2-trifluoroethyl)-6,7-dihydro-2H,5H-4-thia-1,2,7-triaza-azulen-8-one; 3-(4-chlorophenyl)-2-(2-chlorophenyl)-4-oxo-7-(2,2,2-trifluoroethyl)-4,5,6,7-tetrahydro-2H-4$\lambda^4$-thia-1,2,7-triaza-azulen-8-one; 3-(4- chlorophenyl)-2-(2-chlorophenyl)-4,4-dioxo-7-(2,2,2-trifluoroethyl)-4,5,6,7-tetrahydro-2H-4λ⁴-thia-1,2,7-triaza-azulen-8-one; 3-(4-chlorophenyl)-2-(2-chlorophenyl)-6,6-dimethyl-7-(2,2,2-trifluoroethyl)-6,7-dihydro-2H,5H-4-thia-1,2,7-triaza-azulen-8-one; 2-(2-chlorophenyl)-3-(4-chlorophenyl)-7-(2,2,2-trifluoroethyl)-6,7-dihydro-3H,5H-4-oxa-1,3,7-triaza-azulen-8-one; 2-(2-chlorophenyl)-3-(4-chlorophenyl)-7-(2,2-difluoropropyl)-6,7-dihydro-3H,5H-4-oxa-1,3,7-triaza-azulen-8-one; 3-(4-chlorophenyl)-2-(2-chlorophenyl)-6,6-dimethyl-7-(2,2,2-trifluoroethyl)-6,7-dihydro-2H,5H-4-oxa-1,2,7-triaza-azulen-8-one; 3-(4-chlorophenyl)-2-(2-chlorophenyl)-7-(2,2,2-trifluoroethyl)4,5,6,7-tetrahydro-3H-imidazo[4,5-e][1,4]diazepin-8-one; 3-(4-chlorophenyl)-2-(2-chlorophenyl)-4-methyl-7-(2,2,2-trifluoroethyl)-4,5,6,7-tetrahydro-3H-imidazo[4,5-e][1,4]diazepin-8-one; 3-(4-chlorophenyl)-2-(2-chlorophenyl)-4,6,6-trimethyl-7-(2,2,2-trifluoroethyl)4,5,6,7-tetrahydro-3H-imidazo[4,5-e][1,4]diazepin-8-one; 2-(2-chlorophenyl)-3-(4-chlorophenyl)-7-(2,2,2-trifluoroethyl)-6,7-dihydro-3H, 5H4-thia-1,3,7-triaza-azulen-8-one; 2-(2-chlorophenyl)-3-(4-chlorophenyl)4-oxo-7-(2,2,2-trifluoroethyl)-4,5,6,7-tetrahydro-3H-4λ⁴-thia-1,3,7-triaza-azulen-8-one; 2-(2-chlorophenyl)-3-(4-chlorophenyl)4,4-dioxo-7-(2,2,2-trifluoroethyl)4,5,6,7-tetrahydro-3H-4λ⁴-thia-1,3,7-triaza-azulen-8-one; and 2-(2-chlorophenyl)-3-(4-chlorophenyl)-6,6-dimethyl-7-(2,2,2-trifluoroethyl)-6,7-dihydro-3H,5H-4-thia-1,3,7-triaza-azulen-8-one; a pharmaceutically acceptable salt thereof, or a solvate or hydrate of the compound, or the salt.

Some of the compounds described herein contain at least one chiral center; consequently, those skilled in the art will appreciate that all stereoisomers (e.g., enantiomers and diastereoisomers) of the compounds illustrated and discussed herein are within the scope of the present invention. In addition, tautomeric forms of the compounds are also within the scope of the present invention.

Compounds of the present invention have been shown to be useful cannabinoid receptor ligands (in particular, CB1 receptor antagonists). Accordingly, another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include nicotine receptor partial agonists, opioid antagonists (e.g., naltrexone and nalmefene), dopaminergic agents (e.g., apomorphine), attention deficit disorder (ADD including attention deficit hyperactivity disorder (ADHD)) agents (e.g., Ritalin™, Strattera™, Concerta™ and Adderall™), and anti-obesity agents (described herein below).

In yet another embodiment of the present invention, a method for treating a disease, condition or disorder modulated by a cannabinoid receptor (preferably, a CB1 receptor) antagonists in animals that includes the step of administering to an animal in need of such treatment a therapeutically effective amount of a compound of the present invention (or a pharmaceutical composition thereof).

Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD/ADHD), Parkinson's disease, and type II diabetes. In a preferred embodiment, the method is used in the treatment of weight loss, obesity, bulimia, ADD/ADHD, dementia, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ or analogs thereof, MCR-4 agonists, CCK-A agonists, monoamine reuptake inhibitors, sympathomimetic agents, $\beta_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists, thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described above and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described above and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions and/or disorders modulated by cannabinoid receptor antagonists in an animal. The kit comprises a) a suitable dosage form comprising-a compound of the present invention; and b) instructions describing a method of using the dosage form to treat diseases linked to the modulation of the cannabinoid receptor (preferably, the CB1 receptor).

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described above, and (ii) a pharmaceutically acceptable carrier, excipient or diluent; and c) a container.

DEFINITIONS

As used herein, the term "alkyl" refers to a hydrocarbon radical of the general formula $C_nH_{2n+1}$. The alkane radical may be straight or branched. For example, the term "$(C_1–C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., "fluoro-substituted alkyl" refers to fluoromethyl, difluoromethyl, trifluoromethyl, 1-fluoroethyl, 2-fluoroethyl, 1,1-difluoroethyl, 1,2-difluoroethyl, 2,2-difluoroethyl, 1,1,1-trifluoroethyl, 2,2,2-trifluoroethyl, 1,1,2-trifluoroethyl, 1,2,2-trifluoroethyl, 1,2,2,2-tetrafluoroethyl, 1,1,2,2-tetrafluoroethyl, 1,1,1,2-tetrafluoroethyl, 1,1,2,2,2-pentafluoroethyl, 1,1,1,2,2-pentafluoroethyl, perfluoroethyl, etc.). Preferred halo-substituted alkyls are the chloro- and fluoro-substituted alkyls, more preferably, fluoro-substituted alkyls. When substituted, the alkane radicals or alkyl moieties are preferably fluoro substituents (as described above), or 1 or 2 substituents independently selected from $(C_1–C_3)$alkyl, $(C_3–C_6)$cycloalkyl, $(C_2–C_3)$alkenyl, aryl, heteroaryl, 3- to 6-membered heterocycle, chloro, cyano, hydroxy, $(C_1–C_3)$alkoxy, aryloxy, amino, $(C_1–C_6)$alkyl amino, di-$(C_1–C_4)$alkyl amino, aminocarboxylate (i.e., $(C_1–C_3)$alkyl-O—C(O)—NH—), hydroxy$(C_2–C_3)$alkylamino, or keto (oxo), and more preferably, 1 to 3 fluoro groups, or 1 substituent selected from $(C_1–C_3)$alkyl, $(C_3–C_6)$cycloalkyl, $(C_6)$aryl, 6-membered-heteroaryl, 3- to 6-member heterocycle, $(C_1–C_3)$alkoxy, $(C_1–C_4)$alkyl amino or di-$(C_1–C_2)$alkyl amino.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. When substituted, the carbocyclic group is preferably substituted with 1 or 2 substituents independently selected from $(C_1–C_3)$alkyl, $(C_2–C_3)$alkenyl, $(C_1–C_6)$alkylidenyl, aryl, heteroaryl, 3- to 6-membered heterocycle, chloro, fluoro, cyano, hydroxy, $(C_1–C_3)$alkoxy, aryloxy, amino, $(C_1–C_6)$alkyl amino, di-$(C_1–C_4)$alkyl amino, aminocarboxylate (i.e., $(C_1–C_3)$alkyl-O—C(O)—NH—), hydroxy$(C_2–C_3)$alkylamino, or keto (oxo), and more preferably 1 or 2 from substituents independently selected from $(C_1–C_2)$alkyl, 3- to 6-membered heterocycle, fluoro, $(C_1–C_3)$alkoxy, $(C_1–C_4)$alkyl amino or di-$(C_1–C_2)$alkyl amino. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubstiuted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents independently selected from $(C_1–C_3)$alkyl, $(C_3–C_6)$cycloalkyl, $(C_2–C_4)$alkenyl, aryl, heteroaryl, 3- to 6-membered heterocycle, chloro, fluoro, cyano, hydroxy, $(C_1–C_3)$alkoxy, aryloxy, amino, $(C_1–C_6)$alkyl amino, di-$(C_1–C_3)$alkyl amino, aminocarboxylate (i.e., $(C_1–C_3)$alkyl-O—C(O)—NH—), or keto (oxo), and more preferably with 1 or 2 substituents independently selected from $(C_1–C_3)$alkyl, $(C_3–C_6)$cycloalkyl, $(C_6)$aryl, 6-membered-heteroaryl, 3- to 6-membered heterocycle, or fluoro. The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted." Substituted aryl groups include a chain of aromatic moieties (e.g., biphenyl, terphenyl, phenylnaphthalyl, etc.). When substituted, the aromatic moieties are preferably substituted with 1 or 2 substituents independently selected from $(C_1-C_4)$alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$alkyl-O—C(O)—NH—), and more preferably, 1 or 2 substituents independently selected from $(C_1-C_4)$alkyl, chloro, fluoro, cyano, hydroxy, or $(C_1-C_4)$alkoxy. The aryl group may be attached to the chemical entity or moiety by any one of the carbon atoms within the aromatic ring system. Similarly, the aryl portion (i.e., aromatic moiety) of an aroyl or aroyloxy (i.e., (aryl)-C(O)—O—) has the same definition as above.

The term "heteroaryl" or "heteroaromatic ring" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted." When substituted, the heteroaromatic moieties are preferably substituted with 1 or 2 substituents independently selected from $(C_1-C_4)$ alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$alkyl-O—C(O)—NH—), and more preferably, 1 or 2 substituents independently selected from $(C_1-C_4)$alkyl, chloro, fluoro, cyano, hydroxy, $(C_1-C_4)$alkoxy, $(C_1-C_4)$alkyl amino or di-$(C_1-C_2)$alkyl amino. The heteroaryl group may be attached to the chemical entity or moiety by any one of the atoms within the aromatic ring system (e.g., imidazol-1-yl, imidazol-2-yl, imidazol4-yl, imidazol-5-yl, pyrid-2-yl, pyrid-3-yl, pyrid4-yl, pyrid-5-yl, or pyrid-6-yl). Similarly, the heteroaryl portion (i.e., heteroaromatic moiety) of a heteroaroyl or heteroaroyloxy (i.e., (heteroaryl)-C(O)—O—) has the same definition as above.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as $(C_1-C_6)$alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include $(C_1-C_6)$alkyl, $(C_3-C_7)$cycloalkyl, $(C_2-C_6)$ alkenyl, $(C_1-C_6)$alkylidenyl, aryl, heteroaryl, 3- to 6-membered heterocycle, halo (e.g., chloro, bromo, iodo and fluoro), cyano, hydroxy, $(C_1-C_6)$alkoxy, aryloxy, sulfhydryl (mercapto), $(C_1-C_6)$alkylthio, arylthio, amino, mono- or di-$(C_1-C_6)$alkyl amino, quaternary ammonium salts, amino $(C_1-C_6)$alkoxy, aminocarboxylate (i.e., $(C_1-C_6)$alkyl-O—C(O)—NH—), hydroxy$(C_2-C_6)$alkylamino, amino$(C_1-C_6)$ alkylthio, cyanoamino, nitro, $(C_1-C_6)$carbamyl, keto (oxo), acyl, $(C_1-C_6)$alkyl-$CO_2$—, glycolyl, glycyl, hydrazino, guanyl, sulfamyl, sulfonyl, sulfinyl, thio$(C_1-C_6)$alkyl-C(O)—, thio$(C_1-C_6)$alkyl-$CO_2$—, and combinations thereof. In the case of substituted combinations, such as "substituted aryl $(C_1-C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "solvate" refers to a molecular complex of a compound represented by Formula (I) or (II) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated by a cannabinoid receptor" or "modulation of a cannabinoid receptor" refers to the activation or deactivation of a cannabinoid receptor. For example, a ligand may act as an agonist, partial agonist, inverse agonist, antagonist, or partial antagonist.

The term "antagonist" includes both full antagonists and partial antagonists, as well as inverse agonists.

The term "CB-1 receptor" refers to the G-protein coupled type 1 cannabinoid receptor.

The term "compounds of the present invention" (unless specifically identified otherwise) refer to compounds of Formulae (I), (II) (I-A), (I-B), (I-C), (I-D), (I-E), (I-F), (I-G), (I-H), (I-I), (I-J), (I-K), (I-L), (I-M), (I-N), (I-O), (I-P) and (I-Q), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds. All amorphous and crystalline forms of the compounds are included as well.

As used herein, structures drawn with circles within a ring designate aromaticity. For example, the following chemical moiety designates a pyrazole ring when A is nitrogen and B is carbon; and the chemical moiety designates an imidazole when A is carbon and B is nitrogen.

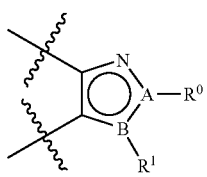 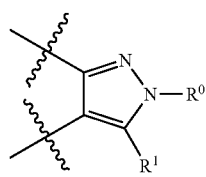

-continued

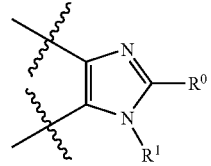

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, New York (1967–1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I outlines the general procedures one could use to provide compounds of the present invention where A is nitrogen, B is carbon and X is O (i.e., compound of Formula (I-A)).

Scheme I

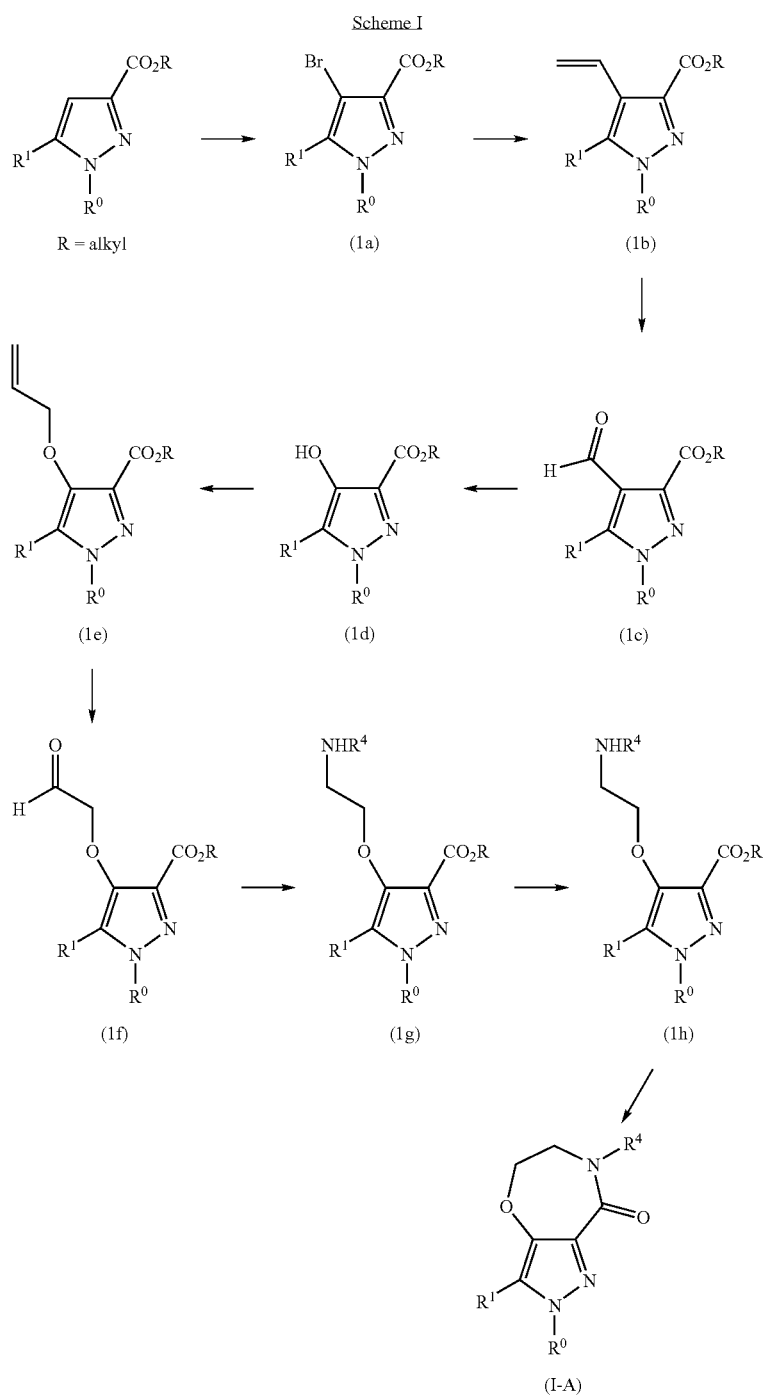

The starting pyrazolo ester may be prepared by procedures described in U.S. Pat. No. 5,624,941 and is incorporated herein by reference. The bromo intermediate (1a) may be prepared using conventional bromination procedures well-known to those skilled in the art. For example, the pyrazolo ester may be treated with bromine in a protic solvent (e.g., acetic acid) at a temperature from about 10° C. to about −10° C. A vinyl group may then be introduced by treating the bromo intermediate (1a) with tributylvinyltin and tetrakistriphenylphosphine palladium in a polar solvent (e.g., dimethylformamide (DMF)) at an elevated temperature. The vinyl group may then be oxidatively cleaved to the corresponding aldehyde. For example, the vinyl intermediate (1b) may be treated with osmium tetroxide in the presence of N-methylmorpholine-N-oxide in an aqueous solvent (e.g., dioxane and water) at about room temperature followed by treatment with sodium periodate. The aldehyde group may then be converted to a hydroxy group by treating aldehyde intermediate (1c) with a percarboxylic acid (e.g., m-chloroperbenzoic acid) in an aprotic solvent (e.g., dichloromethane) followed by treatment with a strong base (e.g., triethylamine) in a protic solvent (e.g., methanol). An appropriate allyl group may be condensed with the hydroxy group to form the desired allyl ether intermediate (1e) using conventional means. For example, hydroxy intermediate (1d) may be treated with a strong base (e.g., sodium hydride) followed by the addition of the desired allyl bromide in a polar solvent (e.g., dimethylsulfoxide (DMSO)). The pendant olefin group may be oxidatively cleaved to its corresponding aldehyde using procedures analogous to those described above for the conversion of vinyl intermediate (1b) to its corresponding aldehyde intermediate (1c). The desired amino group (—NHR$^4$) may be introduced by treating aldehyde intermediate (1e) with the desired amine (R$^4$NH$_2$) in the presence of sodium triacetoxyborohydride (NaBH(OAc)$_3$) in a protic solvent (e.g., acetic acid and 1,2-dichloroethane). The carboxy-protecting group may be removed by treating the ester with a strong base (e.g., an alkali metal hydroxide, such as potassium hydroxide) in a protic solvent (e.g., ethanol). The amino intermediate (1h) may then be cyclized to the final product (I-A) by treatment with 1-propanephosphoric acid cyclic anhydride in the presence of a base (e.g., triethylamine) in an aprotic solvent (1,2-dichloroethane).

Scheme II below illustrates an alternative synthesis of intermediate (1d).

may then be accomplished by heating in a polar solvent (e.g., methanol) in the presence of sodium acetate (or triethylamine).

Scheme III outlines an alternative procedure for synthesizing compounds of the present invention where A is nitrogen, B is carbon and X is O (i.e., compound of Formula (I-B)) starting with intermediate (1d).

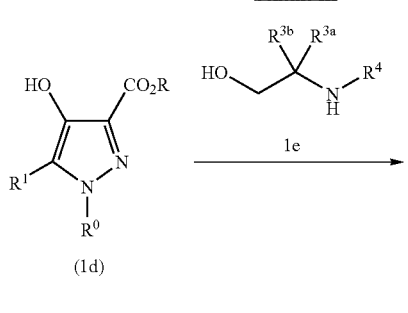

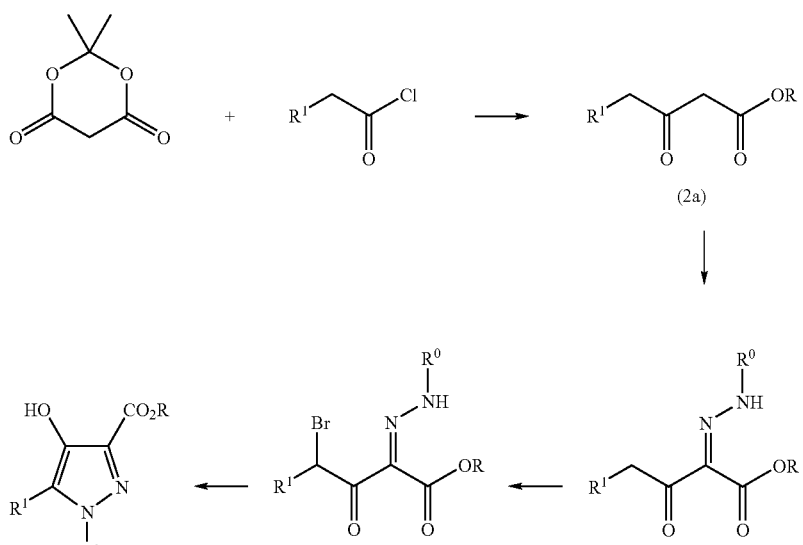

The keto ester intermediate (2a) can be prepared by condensing the desired acid chloride with 2,2-dimethyl-[1,3]dioxane-4,6-dione in the presence of a base (e.g., pyridine) in an aprotic solvent (e.g., methylene chloride) followed by heating at an elevated temperature in a protic solvent (e.g., ethanol). The hydrazono intermediate (2b) can then be prepared by treating the keto ester (2a) with the desired amine in the presence of sodium nitrate in an acidic medium (e.g., aqueous acetic acid). The bromo group may then be introduced using standard bromination procedures well-known to those skilled in the art. For example, intermediate (2b) can be treated with copper (II) bromide in an aprotic solvent (e.g., ethyl acetate and chloroform) at an elevated temperature. Cyclization of the bromo intermediate (2c)

The amide intermediate (3a) may be prepared from the carboxylic ester (1d) by condensing the desired hydroxy amino compound with intermediate (1e) at an elevated temperature in an aprotic solvent (e.g., toluene). The compound of Formula (I-B) may then be produced using standard ether-forming reactions well-known to those skilled in the art. For example, the ether linkage may be formed using the Mitsunobu reaction conditions (1,1'-(azodicarbonyl) dipiperidine (ADDP) in the presence of triphenylphosphine). See, Mitsunobu, O., *Synthesis*, 1 (1981).

Scheme IV outlines the general procedures one could use to provide compounds of the present invention where A is nitrogen, B is carbon, and X is —C($R^{2b}$)($R^{2c}$)—, where $R^{2b}$ and $R^{2c}$ are as defined above.

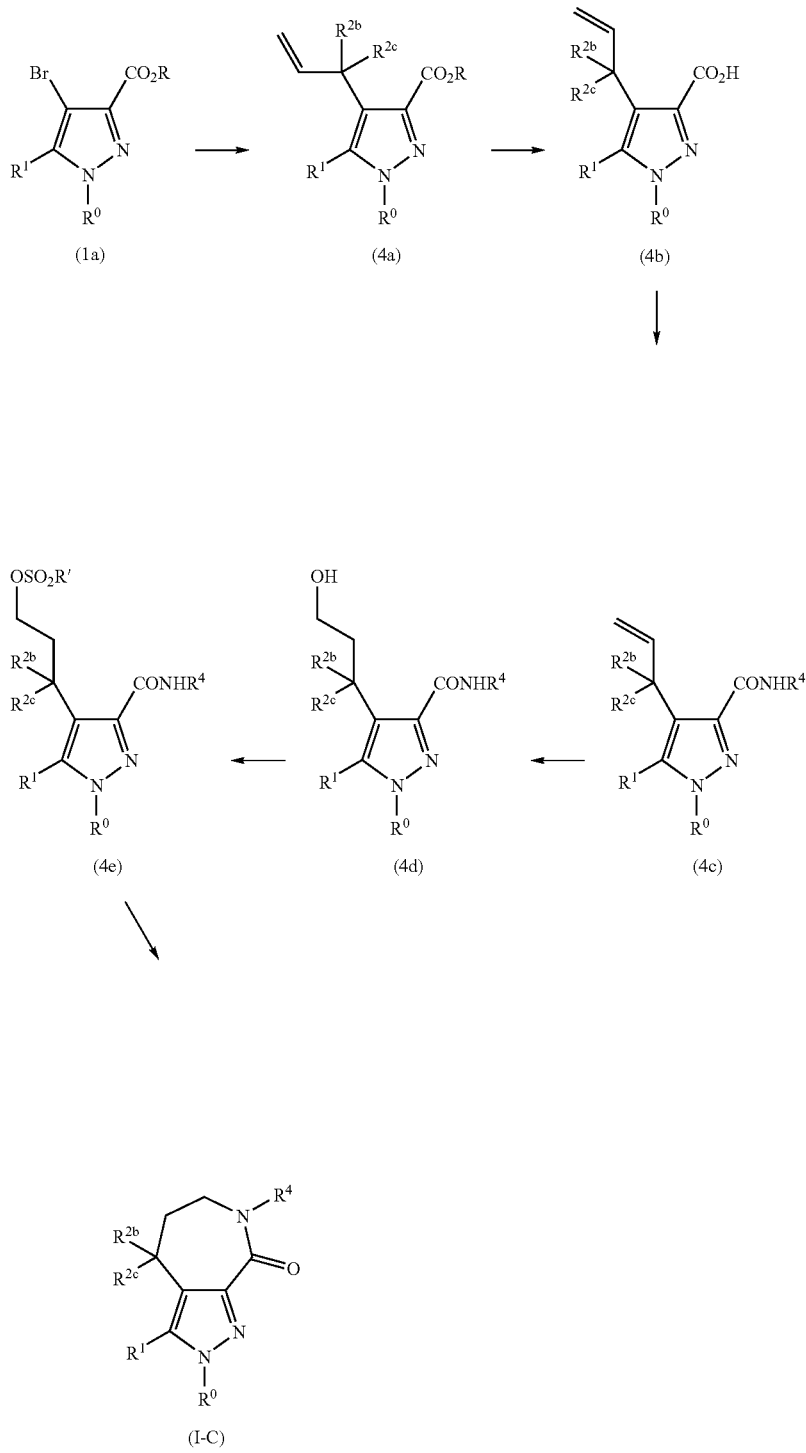

The allyl group of intermediate (4a) may be introduced via a palladium (Pd(0)) catalyzed coupling of the bromo intermediate (1a) with the desired organostannane using procedures analogous to those described by Martorell, G., et al. in "Palladium catalyzed cross-coupling of phenol triflates with organostannanes. A versatile approach for the synthesis of substituted resorcinol dimethyl ethers," *Tetrahedron Lett*, 31(16), 2357–2360 (1990). For example, intermediate (1a) may be treated with the desired organostannane (e.g., allyl-SnBu$_3$) in the presence of a palladium catalyst (e.g., Pd(0)/phosphine (e.g., triphenylphosphine, 1,1'-bisdiphenylphosphinoferrocene (dppf), 1,3-bisdiphenyl-phosphinoopropane (dppp) or 1,2-bisdiphenylphosphinoethane (dppe))/lithium chloride) in refluxing DMF. The carboxy-protecting group may be removed using conventional methods well-known to those skilled in the art, such as treatment with a strong alkali base (e.g., potassium hydroxide) in a protic solvent (e.g., ethanol). The carboxy group may then be condensed with the desired amine (R$^4$NH$_2$) to produce the amide intermediate (4c). For example, carboxylic acid intermediate (4b) may be treated with R$^4$NH$_2$ in the presence of 1-propane-phosphoric acid cyclic anhydride and a base (e.g., triethylamine) in an aprotic solvent (e.g.,1,2-dichloroethane). The vinyl group of the amide intermediate (4c) may be hydrated using conventional means well-known to those skilled in the art. For example, amide intermediate (4c) may be treated with 9-borabicyclo[3.3.1]nonane (9-BBN) in an aprotic solvent (e.g., tetrahydrofuran (THF)) followed by the addition of hydrogen peroxide and aqueous sodium hydroxide. The resultant hydroxy intermediate (4d) may then be sulfonated by reacting the hydroxy group with an alkyl sulfonyl chloride (e.g., R'SO$_2$Cl) in the presence of a base (e.g., triethylamine) and an aprotic solvent (methylene chloride). The sulfonate intermediate (4e) may be cyclized to the final product (I-C) by treating with a strong base (e.g., sodium hydride) in an aprotic solvent (e.g., THF).

Scheme V outlines the general procedures one could use to provide compounds of the present invention where A is nitrogen, B is carbon, and X is —N(R$^{2a}$)—, where R$^{2a}$ is as defined above.

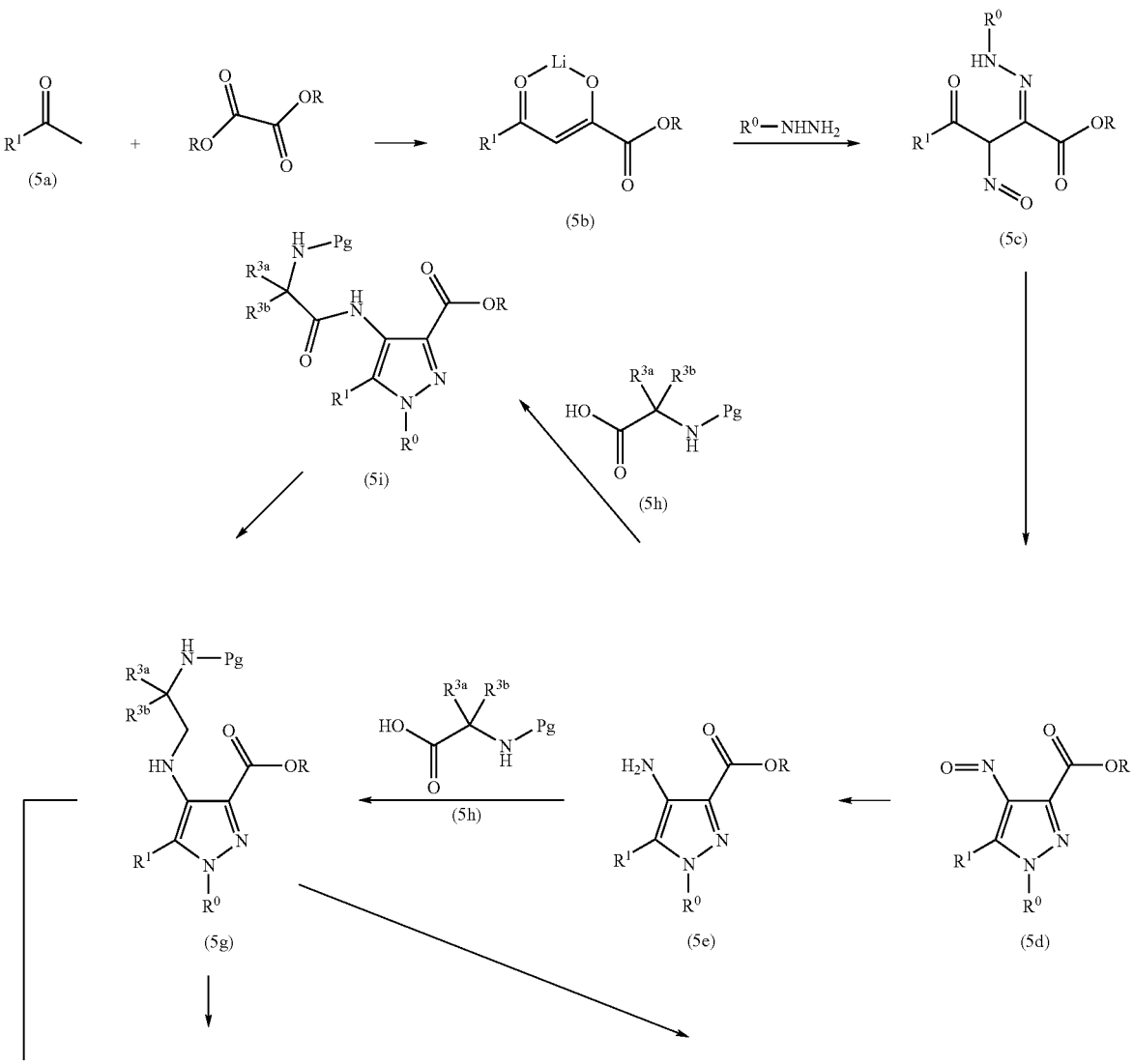

Scheme V

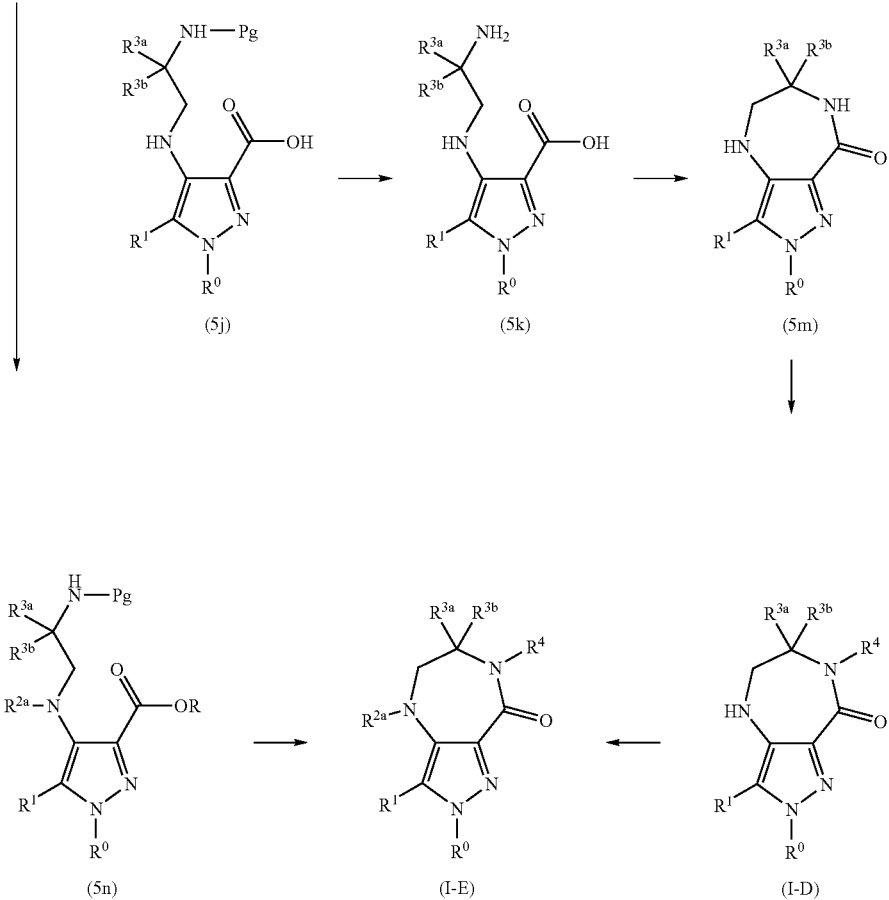

Lithium salt (5b) can be prepared by treatment of methyl ketone (5a) with lithium hexamethyldisilazide at a temperature of about −78° C. in an aprotic solvent such as THF, followed by condensation with diethyl oxalate, as described in WO 00/46209. The isolated lithium salt (5b) is then dissolved in an acid such as acetic acid and nitrosated by dropwise addition of aqueous sodium nitrite at a temperature of about 0–10° C. (*Tetrahedron*, 3, 209 (1958); *Bull. Chem. Soc. Jpn.* 52, 208 (1979)). A substituted hydrazine may then be added directly to the reaction mixture to afford intermediate (5c). Cyclization of (5c) is accomplished by heating intermediate (5c) and a catalytic amount of an acid such as concentrated sulfuric acid in a solvent such isopropanol at a temperature of about 60° C. to provide nitrosopyrazole (5d). The nitroso group of intermediate (5d) can be reduced by treatment of (5d) with sodium dithionite in a mixture of solvents such as ethyl acetate and water, affording aminopyrazole (5e), which may be reductively alkylated with an appropriately protected amino aldehyde (5f) (such as tert-butyl N-(2-oxoethyl)carbamate when $R^4$=H) and a reagent like sodium triacetoxyborohydride or sodium cyanoborohydride to give intermediate (5g) (see, e.g., EP 1329160). Alternatively, amine (5e) can be coupled with acid (5h) under standard conditions to give amide (5i), which can then be reduced (e.g., $BH_3$) to give amine (5g). The carboxy-protecting group in (5g) can be hydrolyzed with a strong base (e.g., an alkali metal hydroxide such as potassium hydroxide) in a polar, protic solvent (e.g., ethanol) to give intermediate (5j). Removal of the amino protecting group using standard methods (e.g., trifluoroacetic acid or aqueous HCl in ethanol for removal of Boc group, hydrogenolysis for removal of Cbz group) can provide the amino acid derivative (5k) which can cyclize in the presence of a coupling reagent (e.g., EDC or O-(7-azabenzotriazol-1-yl)-N,N,N', N'-tetramethyluronium hexafluorophosphate (HATU)) to form the lactam (5m). Alternatively, deprotection of the amino functionality in (5g) using standard conditions, followed by treatment with a base (e.g., sodium ethoxide) in an alcoholic solvent (e.g., ethanol) or with a strong acid such as polyphosphoric acid (PPA) can yield lactam (5m). Compounds of formula (I-D) can be prepared from (5m) by treatment with a suitable alkylating agent (i.e., $R^4$—X where X is a leaving group) in the presence of a strong base (e.g., sodium hydride) in a polar solvent (e.g., DMF, THF). Compounds of formula (I-E) can be prepared from (I-D) by deprotonation with a base such as sodium hydride or sodium hexamethyldisilazide in a solvent such as DMF, followed by alkylation with $R^{2a}$—X. Treatment of (I-D) with an appropriately substituted acyl chloride or acyl anhydride in the presence of a tertiary base such as pyridine, triethylamine, or diisopropylethylamine in a non-polar solvent such as $CH_2Cl_2$ or benzene can provide compounds of Formula (I-E) where $R^{2a}$ is $(C_1–C_4)$alkylcarbonyl. In certain instances, it maybe necessary to first protect the N-4 amino group in intermediate (5m) with a trifluoroacetyl moiety which can be removed in a subsequent step following alkylation with R⁴—X. The $R^{2a}$, group in (I-E) can also be introduced earlier in the sequence by treating intermediate (5g) with an appropriately substituted acylating agent in the presence of base (e.g., DMAP, pyridine) in a non-polar solvent (e.g., $CH_2Cl_2$). If necessary, the amide moiety in intermediate (5g) can be selectively reduced in the presence of the ester functionality using $BH_3$ in a polar solvent (e.g., THF). Deprotection of (5g) and cyclization as previously described can provide compounds of formula (I-E).

Representative examples of compounds of Formula (I-D) that may be prepared by the procedures described above in Scheme IV include: 3-(4-chlorophenyl)-2-(2-chlorophenyl)-7-(2,2,2-trifluoroethyl)4,5,6,7-tetrahydro-2H-pyrazolo[4,3-e][1,4]diazepin-8-one; and 3-(4-chlorophenyl)-2-(2-chlorophenyl)-6,6-dimethyl-7-(2,2,2-trifluoroethyl)-4,5,6,7-tetrahydro-2H-pyrazolo[4,3-e][1,4]diazepin-8-one.

A representative example of a compound of Formula (I-E) that may be prepared by the procedures described above in Scheme IV includes 3-(4-chlorophenyl)-2-(2-chlorophenyl)-4,6,6-trimethyl-7-(2,2,2-trifluoroethyl)-4,5,6,7-tetrahydro-2H-pyrazolo[4,3-e][1,4]diazepin-8-one.

Scheme VI outlines a variation in the procedure described in Scheme V where the R⁴ substituent is already present in the starting aldehyde (6a) or acid (6c).

The aminopyrazole intermediate (5e) can be treated with an aldehyde intermediate (6a) in the presence of an acid catalyst (e.g. acetic acid) and reducing agent (e.g. $NaBH_3CN$, $NaBH(OAc)_3$) in a non-polar solvent (e.g. 1,2-dichloroethane) to give intermediate (6b). Alternatively, amine (5e) can be acylated with acid (6c) under standard conditions to give amide (6d), which can then be reduced (e.g., $BH_3$) to give amine (6b). Removal of the amino protecting group under standard conditions can yield intermediate (6e) that can be converted into lactam (I-F) as previously described. Representative examples of compounds of Formula (I-F) that may be prepared by the procedures described above in Scheme VI include 2-(2-chlorophenyl)-1-(4-chlorophenyl)-9-methyl-5,6,7,7a,8,9-hexahydro-2H-2,3,4a,9-tetraazacyclopenta[f]azulen-4-one; and 2-(2-chlorophenyl)-1-(4-chlorophenyl)-2,5,6,7,8,8a,9,10-octahydro-2,3,4a,10-tetraaza-benzo[f]azulen-4-one.

Scheme VII outlines an alternative procedure to prepare compounds of the present invention where A is nitrogen, B is carbon, $R^{3a}$ is hydrogen and $R^{3b}$ is hydrogen, and X is —$N(R^{2a})$—, where $R^{2a}$ is as defined above.

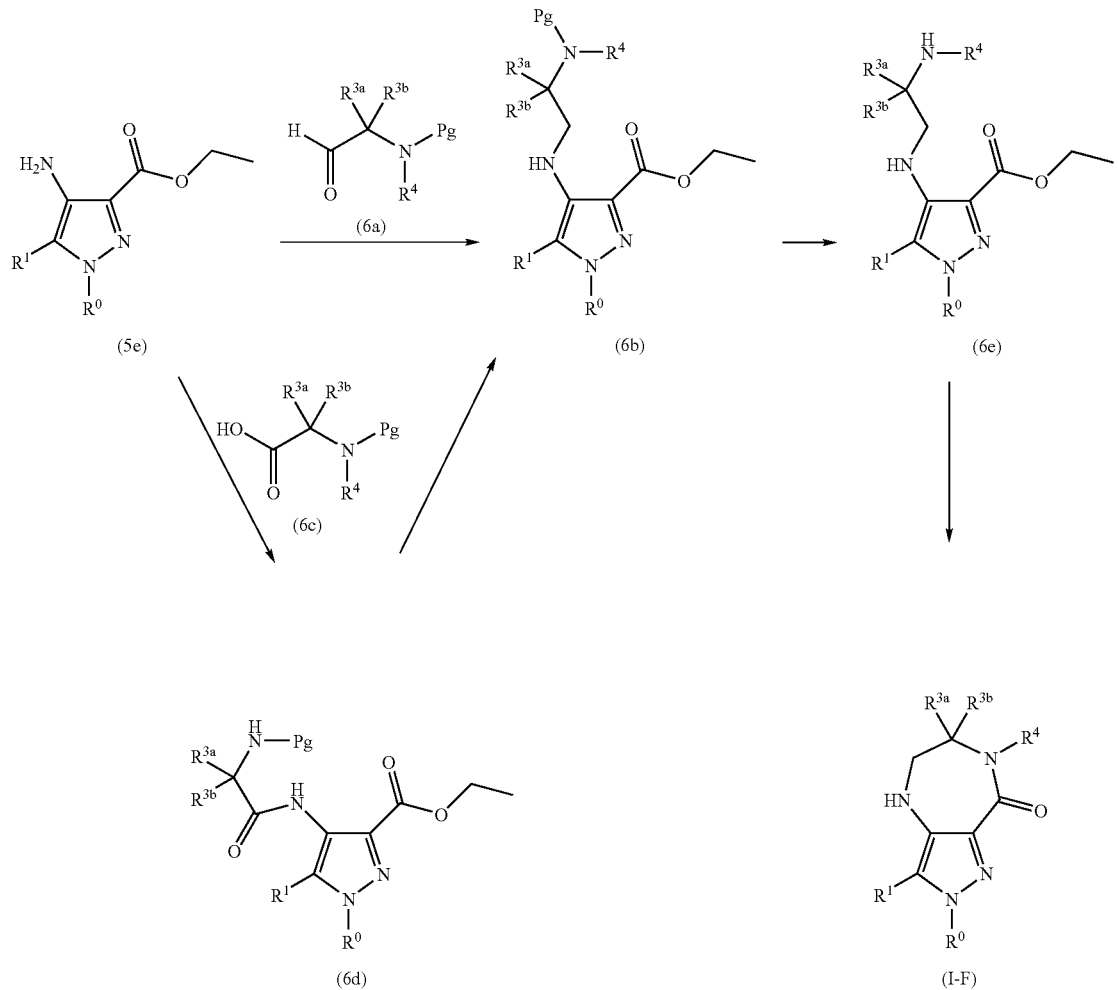

Scheme VI

Scheme VI

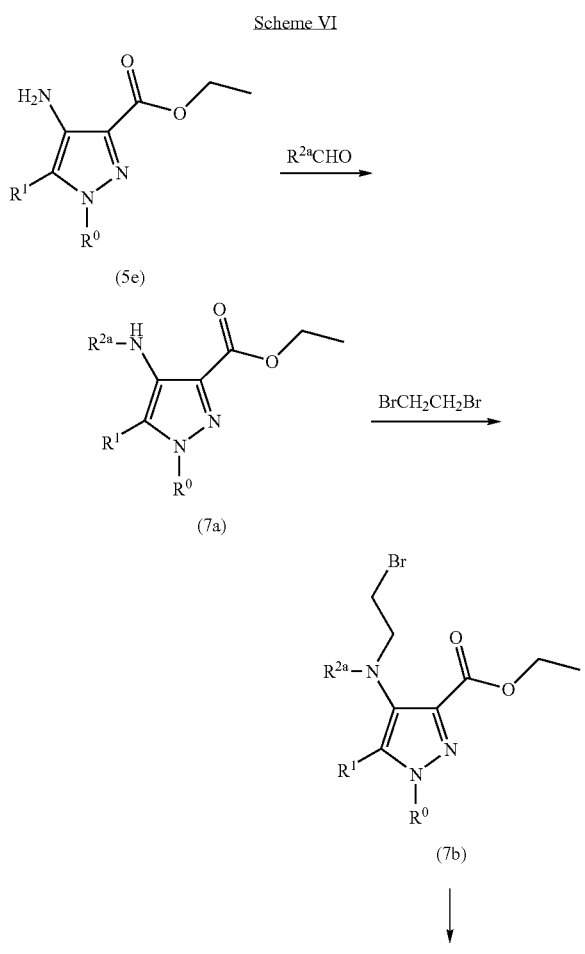

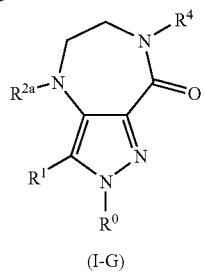

(I-G)

Intermediate (7a) may be prepared from amine (5e) using conventional reductive amination procedures well known to those skilled in the art. Intermediate (7a) may also be prepared by acylation of (5e), followed by selective amide reduction as described earlier. The amine may then be homologated to bromide (7b), such as by alkylation with 1,2-dibromoethane in the presence of a base like potassium carbonate or sodium carbonate in a suitable solvent (e.g., acetonitrile, THF, or DMF) at a temperature from around 0–100° C. using procedures such as those described in *Heteroatom Chemistry*, 13, 63–71 (2002). Subsequent treatment with a primary amine will give an intermediate secondary amine (see U.S. Pat. No. 6,207,663) which may spontaneously cyclize to the lactam (I-G). Alternatively, the ester can be hydrolyzed to the acid and then coupled with the amine to form the lactam (I-G) using conditions well-known to those skilled in the art. A representative example of compound of Formula (I-G) that may be prepared by the procedures described above in Scheme VII includes 3-(4-chlorophenyl)-2-(2-chlorophenyl)-4-methyl-7-(2,2,2-trifluoroethyl)-4,5,6,7-tetrahydro-2H-pyrazolo[4,3-e][1,4]diazepin-8-one.

Compounds of the present invention where A is carbon, B is nitrogen, $R^{3a}$ and $R^{3b}$ are hydrogen, and X is O can be prepared as shown in Scheme VIII.

Scheme VIII

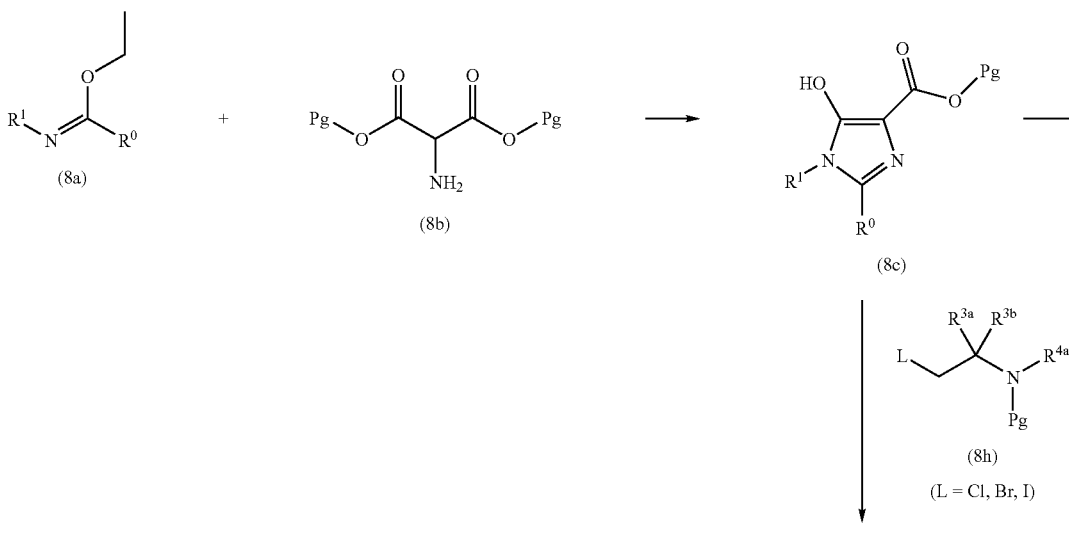

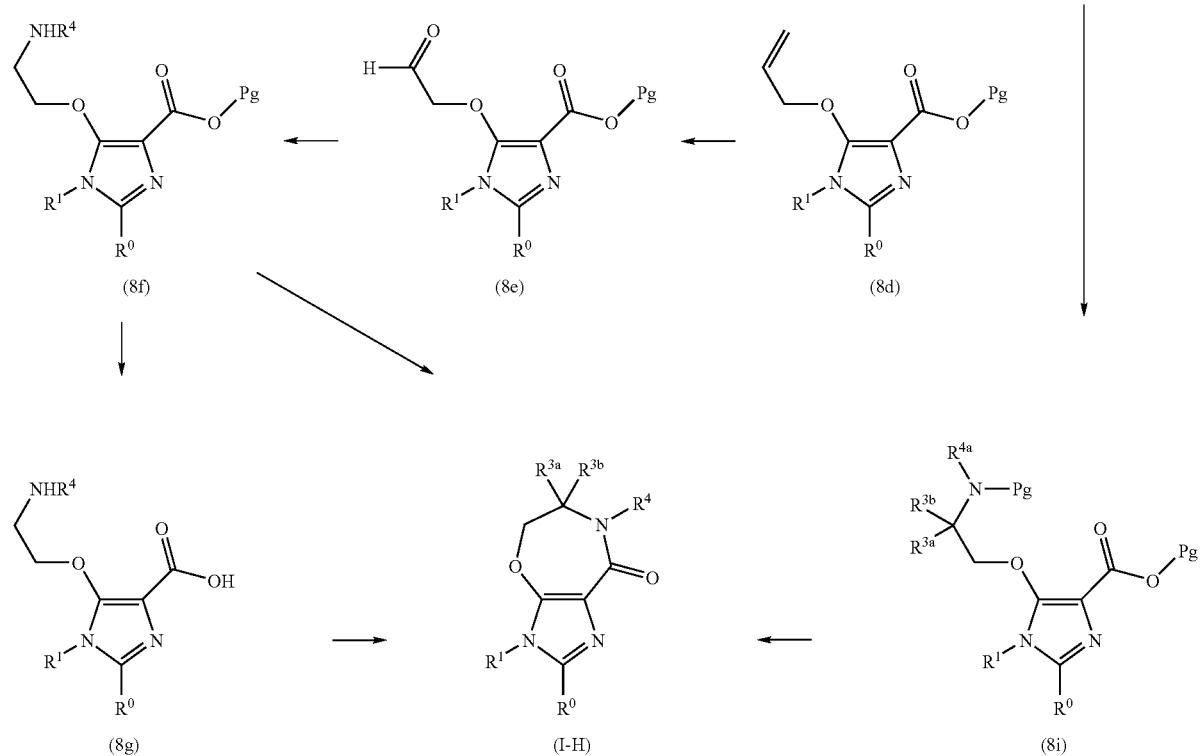

Intermediate (8a) can be reacted with dialkyl aminomalonate (8b) to provide the 5-hydroxy-1H-imidazole4-carboxylic acid alkyl ester derivative (8c) using procedures analogous to those described in *J. Het. Chem.* 19, 193–200 (1982). Treatment of (8c) with allyl bromide in a polar solvent (e.g., THF) using a mild base (e.g., potassium carbonate) can provide the O-alkylated intermediate (8d). The olefin group in (8d) can be di-hydroxylated using osmium tetroxide in the presence of 10 N-methylmorpholine-N-oxide in an aqueous solvent (e.g. dioxane and $H_2O$) and the diol intermediate can be oxidatively cleaved using sodium periodate to give intermediate (8e). Treatment of the aldehyde (8e) with an appropriately substituted amine ($R^4NH_2$) in the presence of an acid catalyst (e.g. HOAc) and a reducing agent (e.g., $NaBH_3CN$, $NaBH(OAc)_3$) can yield intermediate (8f). Hydrolysis of the carboxy-protecting group in (8f) can provide intermediate (8g) which can be cyclized in the presence of EDC or HATU as previously described to provide compound (I-H). Intermediate (8f) can be converted directly into (I-H) under acidic (PPA) or basic (NaOEt/EtOH) conditions as described earlier.

In an alternative synthesis of compounds of formula (I-H) wherein $R^{3a}$ and $R^{3b}$ may be a substituent other than hydrogen, intermediate (8c) can be reacted with a substituted or unsubstituted β-haloethyleneamine derivative where the amino group is suitably protected and $R^{4a}$ is either hydrogen or $R^4$. The product from the alkylation step, intermediate (8i), can be deprotected under standard conditions and cyclized in the presence of acid (e.g., PPA) or base (e.g., NaOEt/EtOH) to yield (I-H) when $R^{4a}$ is $R^4$. When $R^{4a}$ is hydrogen, the amide may be alkylated under standard conditions as described above to provide (I-H).

Scheme IX describes an alternative method for preparing intermediate (8c).

Scheme IX

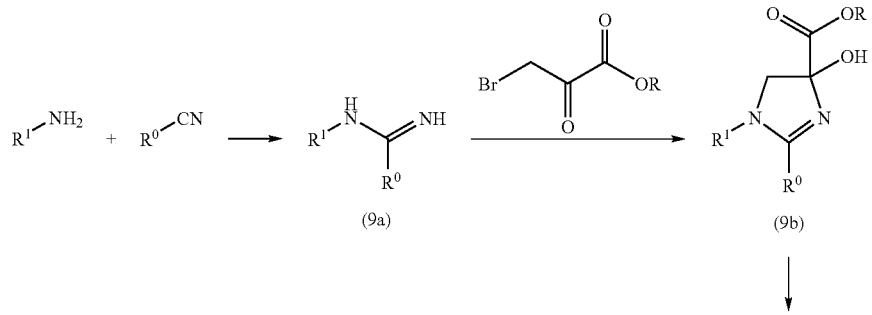

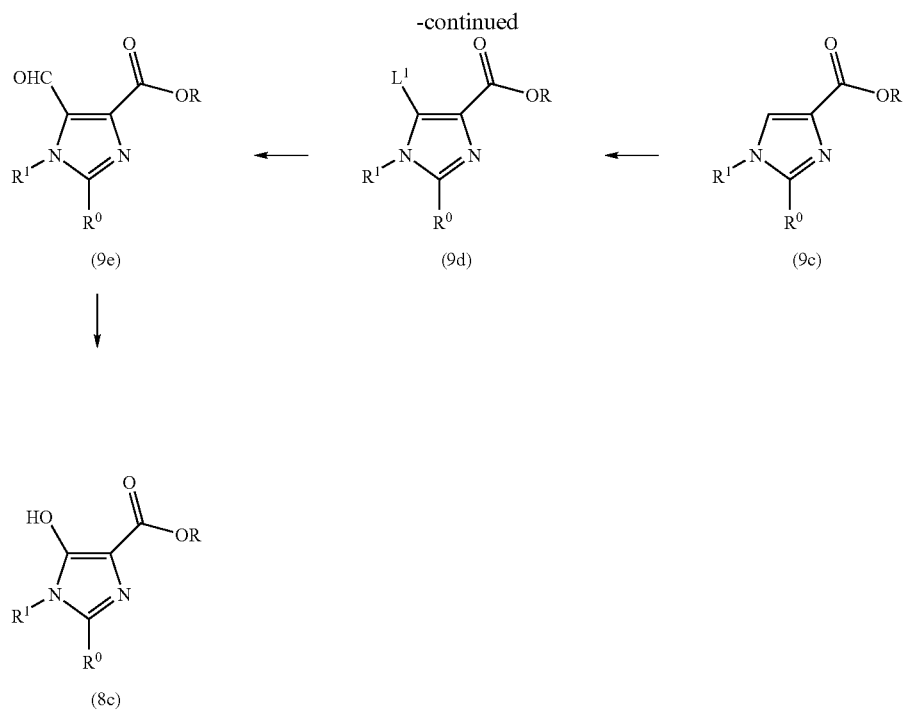

Intermediate (9a) can be prepared by treating the appropriate amine having the desired $R^1$ group with trimethylaluminum under inert atmospheric conditions followed by condensation with the appropriate cyanide having the desired $R^0$ group. Suitable amines include substituted phenyl amines (e.g., 4-chlorophenyl amine, 4-fluorophenyl amine, 4-bromophenyl amine, 4-iodophenyl amine, 4-cyanophenyl amine, and the like) pyridin-2-yl amine, pyridin-3-yl amine, pyridin-4-yl amine, substituted pyridinyl amines (e.g., 2-dimethylaminopyridin-5-yl amine, 2-methoxypyridin-5-yl amine, 5-chloropyridin-2-yl amine, 5-methylpyridin-2-yl, 5-methoxypyridin-2-yl amine, 3-chloropyridin-4-yl; amine, 2-N-morpholinylpyridin-5-yl, and the like), and other commercially available or easily synthesized substituted or unsubstituted aryl and heteroaryl amines. Suitable cyano compounds include substituted benzonitriles (e.g., 2-chlorobenzonitrile, 2-fluorobenzonitrile, 2-methoxybenzonitrile, 2-methylbenzonitrile, 2,4-dichlorobenzonitrile, 2,4-difluorobenzonitrile, 2-chloro4-fluorobenzonitrile, 2-chloro4-methylbenzonitrile, 2,4-dimethoxybenzonitrile, 2-methyl4-chlorobenzonitrile, and the like), cyano-substituted pyridines (e.g., 4-cyano-3-chloropyridine) and other commercially available or easily synthesized substituted or unsubstituted aryl or heteroaryl nitriles.

Intermediate (9a) can then be condensed with a 3-bromo-2-oxo-propionic acid ester (wherein R is an alkyl group like methyl, ethyl, propyl, benzyl, etc.) to produce the cyclized 4-hydroxy-4,5-dihydro-1H-imidazole ester (9b) using procedures analogous to those described by Khanna, I. K., et al., in *J. Med. Chem.*, 40, 1634 (1997). For example, the amidine intermediate (8a) is refluxed in a polar solvent (e.g., isopropanol) in the presence of a mild base (e.g., sodium bicarbonate). Generally, the reaction (i.e., cyclization followed by dehydration) proceeds directly to the desired imidazole ester intermediate (9c). In some instances, it may be necessary to dehydrate the carbinol condensation product (9b) with an acid catalyst (e.g., toluene sulfonic acid in refluxing toluene) to provide the desired imidazole ester (9c).

The imidazole ester (9c) can be prepared from the 4-hydroxy-4,5-dihydro intermediate (9b) using standard dehydration procedures well-known to those skilled in the art. For example, intermediate (9b) may be treated with p-toluenesulfonic acid monohydrate in refluxing toluene. Alternatively, intermediate (9b) may be treated with methanesulfonyl chloride in the presence of a base (e.g., triethylamine).

Intermediate (9d, where $L^1$ is a halogen) can be synthesized from imidazole ester (9c) using a halogenating agent such as bromine, N-bromosuccinimide, iodine, or N-iodosuccinimide in a suitable protic solvent such as glacial acetic acid or trifluoroacetic acid or an aprotic solvent such as acetonitrile, ether or THF, at reaction temperatures ranging from 35° C. to 100° C. Transmetalation of (9d) using an alkyl lithium base, preferentially n-BuLi or tert.-butyl lithium, or an alkyl Grignard reagent such MeMgBr or EtMgBr, in a polar, aprotic solvent such as diethyl ether, dioxane or THF, at reaction temperatures ranging from −100° C. to −78° C., followed by treatment with a formyl equivalent such as DMF, formylpiperidine, or ethyl formate provides the aldehyde derivative (9e). Alternatively, (8e) may be prepared directly from (9c) by: (1) treatment with $POCl_3$ or $POBr_3$ in a solvent such as DMF at reaction temperatures ranging from 35° C. to 100° C., followed by hydrolysis; or (2) preparing in situ several equivalents of a Vilsmeier reagent ($POCl_3$ or $POBr_3$ in DMF) in an aprotic solvent such as $CH_2Cl_2$ or dichloroethane, followed by hydrolysis. The aldehyde intermediate (9e) can be converted into the hydroxy intermediate (8c) by the methods described in Scheme I for the conversion of intermediate (1c) to intermediate (1d).

The aldehyde intermediate (9e) may also be synthesized by the general route shown in Scheme X below.

Scheme X

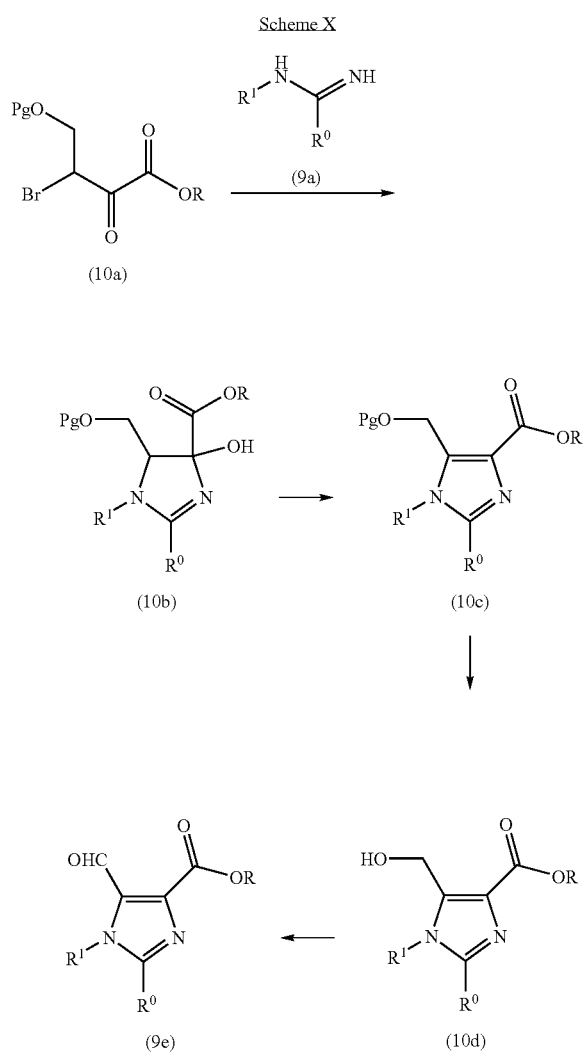

Intermediate (9a) can be condensed with 3-bromo-4-hydroxy-2-oxo-butyric acid alkyl ester derivative (10a with a suitable protecting group on the 4-hydroxy substituent to produce the cyclized intermediate (10b) which can be dehydrated as previously described to give the imidazoyl intermediate (10c). The protecting group (Pg) on the 5-hydroxymethyl group in intermediate (10c can be subsequently removed by standard procedures well known to those skilled in the art. Intermediate (10d) may then be transformed into (9e) using oxidation procedures analogous to those described in *Tett. Lett.*, 35, 9391–4 (1994) or *J. Het. Chem.*, 39, 841–844 (2002). For example, the 5-hydroxymethylimidazolyl derivative (9d) can be treated with oxalyl chloride, DMSO and a tertiary amine base such as triethylamine or diisopropylethylamine in a halogenated solvent such as $CH_2Cl_2$ or $CHCl_3$. Alternatively, the intermediate (10d) can be oxidized using $MnO_2$ in a polar or non-polar solvent such as MeOH, acetone, dioxane, ether, $CH_2Cl_2$, or $CHCl_3$.

Representative examples of compounds of Formula (I-H) that may be prepared by the procedures described above in Schemes VIII, IX or X include: 2-(2-chlorophenyl)-3-(4-chlorophenyl)-7-(2,2,2-trifluoroethyl)-6,7-dihydro-3H,5H-4-oxa-1,3,7-triaza-azulen-8-one; 2-(2-chlorophenyl)-3-(4-chlorophenyl)-7-(2,2-difluoropropyl)-6,7-dihydro-3H,5H-4-oxa-1,3,7-triaza-azulen-8-one; and 3-(4-chlorophenyl)-2-(2-chlorophenyl)-6,6-dimethyl-7-(2,2,2-trifluoroethyl)-6,7-dihydro-2H,5H-4-oxa-1,2,7-triaza-azulen-8-one.

Compounds of the present invention where A is carbon, B is nitrogen and X is N can be prepared as shown in Scheme XI.

Scheme XI

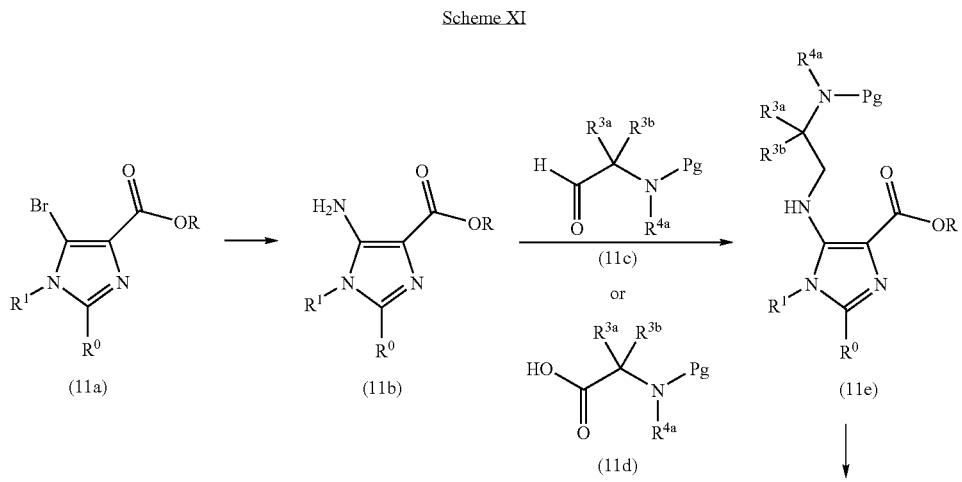

-continued

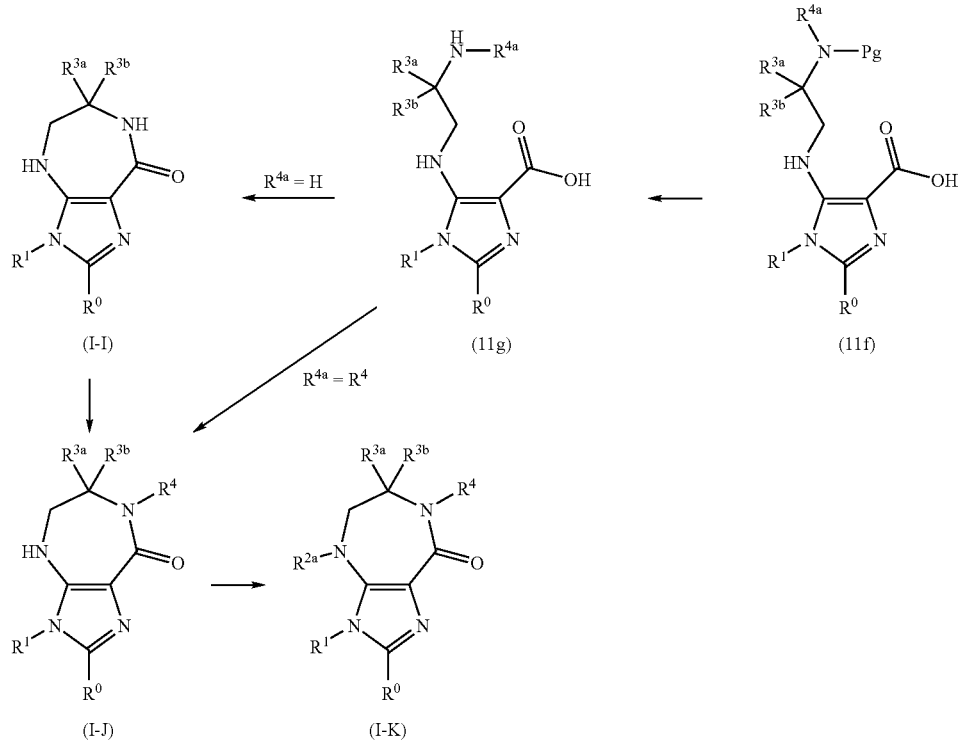

The intermediate (11a), prepared as shown in Scheme IX for compound (9d, L=Br), can be treated with an ammonia equivalent such as lithium bis(trimethylsilyl)amide in the presence of a catalytic amount of $Pd(dba)_2$ and a phosphine ligand such as $P(t-Bu)_3$ in a non-polar solvent (e.g., toluene) at temperatures ranging from 23° C. to reflux to give intermediate (11b). Examples of related procedures are described by Lee et al. in *Organic Letters*, 3, 2729–273 (2001). Treatment of (11b) with an appropriately protected amino aldehyde derivative (11c) (such as tert.-butyl N-(2-oxoethyl)carbamate when $R^{4a}$=H), wherein $R^{4a}$ is either hydrogen or $R^4$, and a reducing reagent (e.g., sodium triacetoxyborohydride or sodium cyanoborohydride) can provide intermediate (11e) (see, e.g., EP 1329160). Alternatively, amine (11b) can be acylated with acid (11d) under standard conditions to give an amide, which can then be reduced (e.g., $BH_3$) to give amine (11e) as described above.

Hydrolysis of the carboxy-protecting group in (11e) with aqueous $K_2CO_3$ in an alcoholic solvent or with an alkali base such as KOH in a polar solvent (e.g., ethanol) can provide intermediate (11f). Deprotection of the amino group in (11f) using standard methods can provide intermediate (11g), which can undergo cyclization as previously described to form lactam (I-I, $R^{4a}$=H) or compound (I-J, $R^{4a}$=$R^4$). Alternatively, the amino protecting group in (11e) can be removed and the product treated with a base (e.g., sodium methoxide) in an alcoholic solvent (e.g., methanol) or an acid (e.g., PPA) to form the lactam (I-I, $R^{4a}$=H) or compound (I-J, $R^{4a}$=$R^4$) as described previously. Compounds of formula (I-J) is and (I-K) can be prepared from (I-I) as described for pyrazolyl analogs (I-D) and (I-E) in Schemes V–VII.

Compounds of formula (I-J) can also be prepared from compound (I-I) via the route shown in Scheme XII.

Scheme XII

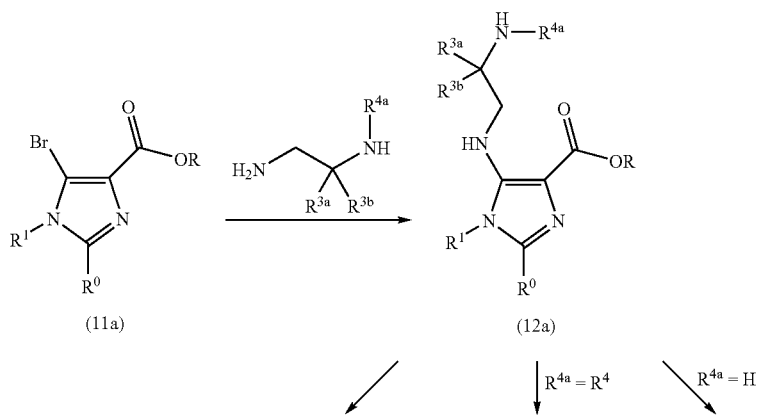

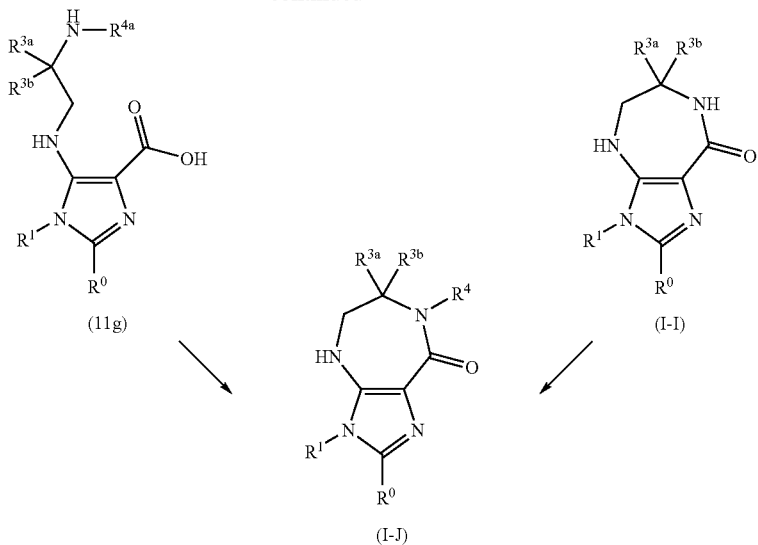

Reaction of intermediate (11a) with ethylenediamine or an appropriately substituted ethylenediamine derivative and cupric oxide in a solvent such as pyridine in the presence of a base such as potassium carbonate can provide intermediate (12a) which can undergo cyclization under basic (NaOMe/MeOH) or acidic (PPA) conditions to provide intermediate (11h, $R^{4a}$=H) or compound (I-I, where $R^{4a}$=$R^4$). Alternatively, ester (12a) may be hydrolyzed to prove acid (11g). Methods described in Scheme XI can be used to convert intermediate (11g) and compound (I-I) to compounds of Formula (I-J).

Representative examples of compounds of Formula (I-I), (I-J) or (I-K) that may be prepared by procedures described above in Schemes XI and XII include: 3-(4-chlorophenyl)-2-(2-chlorophenyl)-7-(2,2,2-trifluoroethyl)4,5,6,7-tetrahydro-3H-imidazo[4,5-e][1,4]diazepin-8-one; 3-(4-chlorophenyl)-2-(2-chlorophenyl)4-methyl-7-(2,2,2-trifluoroethyl)-4,5,6,7-tetrahydro-3H-imidazo[4,5-e][1,4]diazepin-8-one; and 3-(4-chlorophenyl)-2-(2-chlorophenyl)-4,6,6-trimethyl-7-(2,2,2-trifluoroethyl)-4,5,6,7-tetrahydro-3H-imidazo[4,5-e][1,4]diazepin-8-one.

Scheme XIII describes the preparation of compounds of formula (I-L), (I-M), and (I-N) where A is nitrogen, B is carbon, and X is S, SO, or $SO_2$.

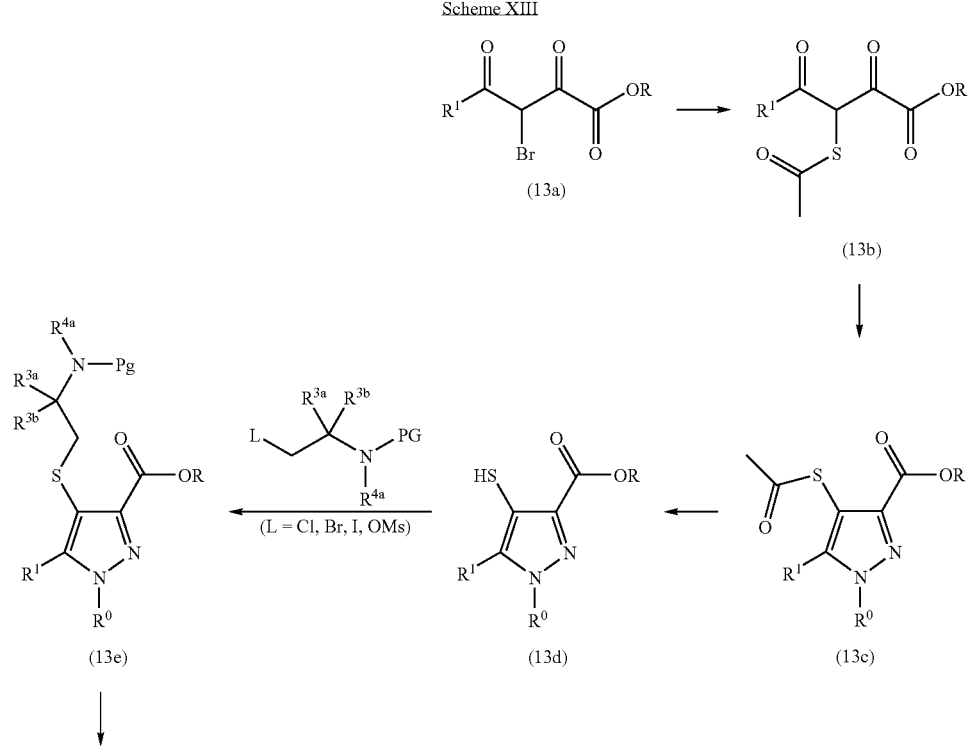

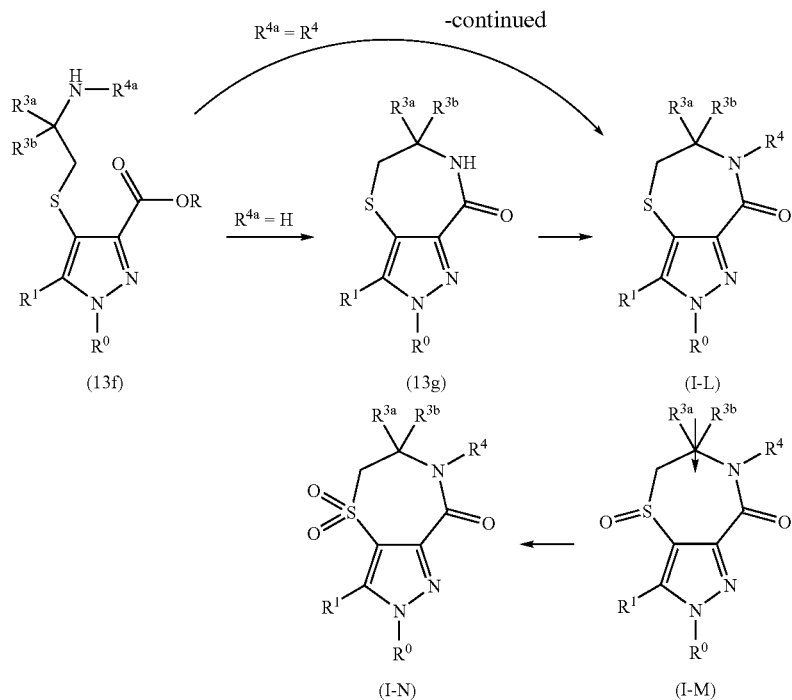

(13f) (13g) (I-L)

(I-N) (I-M)

Compound (13a, see Andreichikov et al., *J. Org. Chem. USSR* (Engl. Transl.), 23(4), 798–792 (1987)) is reacted with thioacetic acid in a polar aprotic solvent (e.g, ether or THF) in the presence of an amine base (e.g., triethylamine) at temperatures ranging from 0° C. to 100° C. to give intermediate (13b). Condensation of (13b) with a substituted hydrazino derivative ($R^0NHNH_2$) in the presence of an acid catalyst (e.g., sulfuric acid, acetic acid) in a solvent such as ethanol, isopropanol, or toluene can provide the pyrazolyl intermediate (13c). Removal of the thioacetyl protecting group with a reducing agent such as $LiBH_4$ in a polar solvent such as THF at temperatures ranging from 0° to 80° C. can provide the 4-mercapto-1H-pyrazole-3-carboxylic acid alkyl ester derivative (13d). Compound (13d) can be reacted with an appropriately substituted or unsubstituted β-haloethyleneamine derivative where the amino group is protected with a suitable group (i.e., Pg) in the presence of a mild base (e.g, $Na_2CO_3$, $K_2CO_3$). Deprotection of the amino group under standard conditions can provide compounds such as (13f) which can be cyclized in the presence of acid (e.g., PPA) or base (e.g. NaOMe/MeOH) as described earlier. Alkylation of (13g) using procedures analogous to those shown in Scheme IV can yield compounds such as (I-L). Compound (I-L) can be converted to the corresponding sulfoxide (I-M) or sulfone (I-N) using an oxidizing agent such as m-chloroperbenzoic acid (m-CPBA) or an oxaziridine, with the oxidation state of the sulfur atom dependent on the reaction time.

Representative examples of compounds of Formula (I-L), (I-M) and (I-N) that may be prepared by the procedures described above in Scheme XII include: 3-(4-chlorophenyl)-2-(2-chlorophenyl)-7-(2,2,2-trifluoroethyl)-6,7-dihydro-2H, 5H-4-thia-1,2,7-triaza-azulen-8-one; 3-(4-chlorophenyl)-2-(2-chlorophenyl)-4-oxo-7-(2,2,2-trifluoroethyl)-4,5,6,7-tetrahydro-2H-4λ$^4$-thia-1,2,7-triaza-azulen-8-one; 3-(4-chlorophenyl)-2-(2-chlorophenyl)-4,4-dioxo-7-(2,2,2-trifluoroethyl)-4,5,6,7-tetrahydro-2H-4λ$^4$-thia-1,2,7-triaza-azulen-8-one; and 3-(4-chlorophenyl)-2-(2-chlorophenyl)-6,6-dimethyl-7-(2,2,2-trifluoroethyl)-6,7-dihydro-2H,5H4-thia-1,2,7-triaza-azulen-8-one.

Scheme XIV describes the preparation of compounds of Formula (I-O), (I-P), and (I-Q) where A is carbon, B is nitrogen, and X is S, SO, or $SO_2$.

Scheme XIV

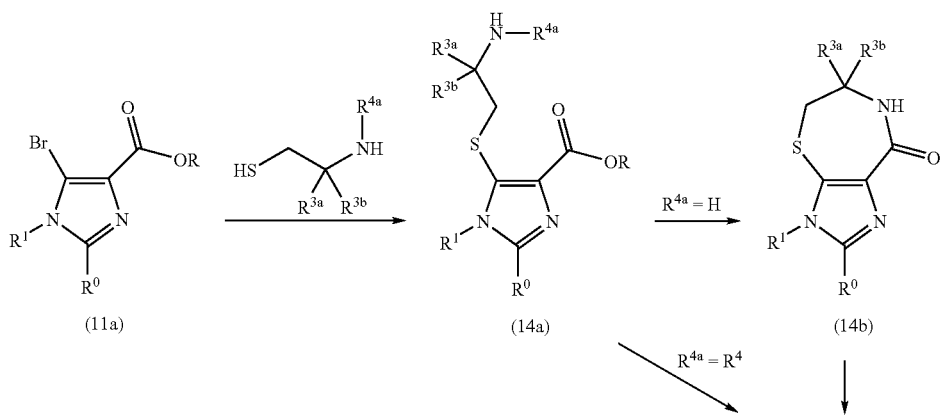

(11a) (14a) (14b)

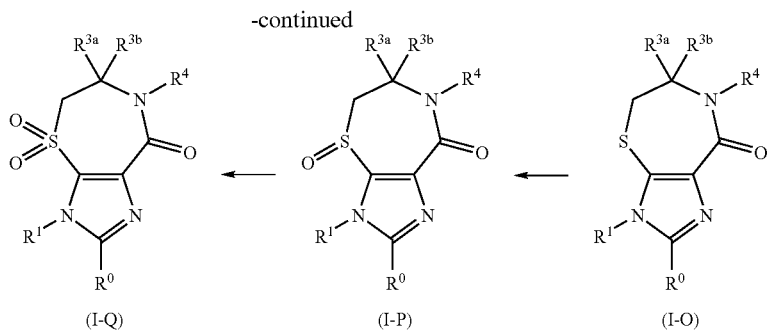

Compound (11a) can be reacted with cysteamine or a substituted 2-amino-propane-1-thiol derivative in a solvent such as DMF in the presence of a base such as 1,8-diazabicyclo[5.4.0]undec-7-ene (DBU) to provide intermediate (14a) which can then be cyclized under acidic (e.g., polyphosphoric acid (PPA)) or basic (e.g., NaOMe/MeOH) conditions to yield intermediate (14b, $R^{4a}$=H) or compound (I-O, $R^{4a}$=$R^4$). Alkylation of (14b) using procedures analogous to those shown in Scheme V can yield compounds such as (I-O). Compound (I-O) can be converted to the corresponding sulfoxide (I-P) or sulfone (I-Q) using an oxidizing agent as previously described.

Representative examples of compounds of Formula (I-O), (I-P), and (I-Q) that may be prepared by the procedures described above in Scheme XIV include: 2-(2-chlorophenyl)-3-(4-chlorophenyl)-7-(2,2,2-trifluoroethyl)-6,7-dihydro-3H,5H-4-thia-1,3,7-triaza-azulen-8-one; 2-(2-chlorophenyl)-3-(4-chlorophenyl)4-oxo-7-(2,2,2-trifluoroethyl)-4,5,6,7-tetrahydro-3H-4λ$^4$-thia-1,3,7-triaza-azulen-8-one; 2-(2-chlorophenyl)-3-(4-chlorophenyl)4,4-dioxo-7-(2,2,2-trifluoroethyl)4,5,6,7-tetrahydro-3H-4λ$^4$-thia-1,3,7-triaza-azulen-8-one; and 2-(2-chlorophenyl)-3-(4-chlorophenyl)-6,6-dimethyl-7-(2,2,2-trifluoroethyl)-6,7-dihydro-3H,5H-4-thia-1,3,7-triaza-azulen-8-one.

Compounds of Formula (I-R) where A is carbon, B is nitrogen, and X is $C(R^{2b})(R^{2c})$ can be prepared as shown in Scheme XV.

Scheme XV

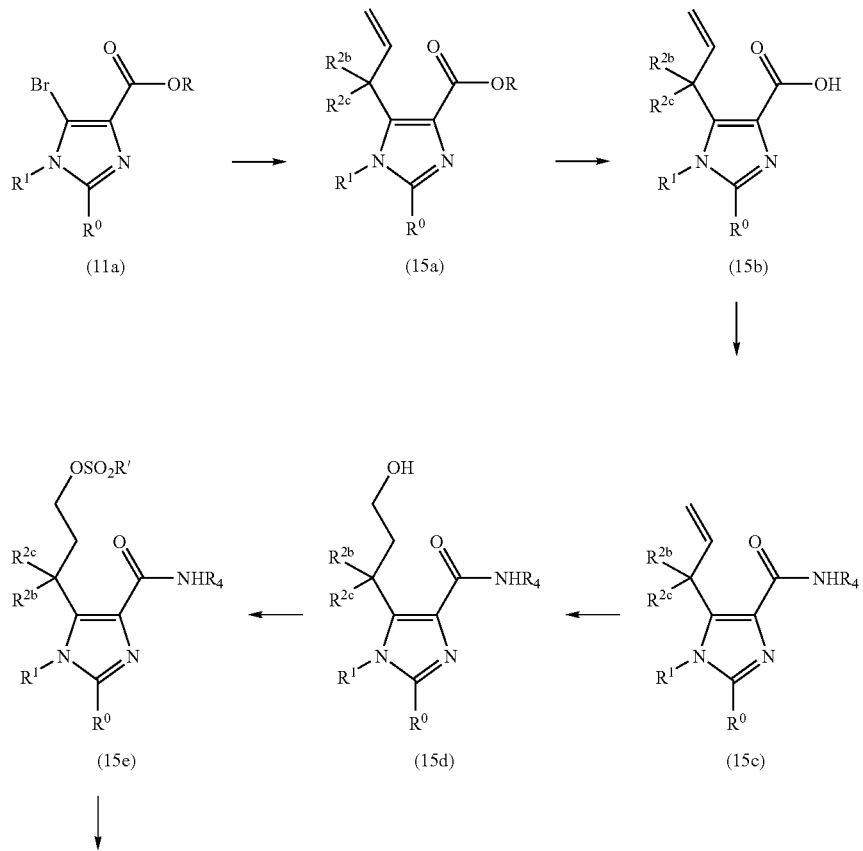

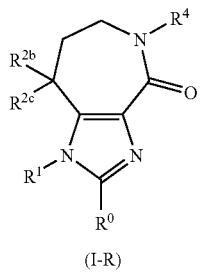

(I-R)

The imidazolyl intermediate (11a) can be converted into intermediate (15e) by methods analogous to those described in Scheme IV. Treatment of (15e) with a strong base (e.g., sodium hydride) in an aprotic solvent (e.g., THF) can provide compounds of formula (I-R).

Representative examples of compounds of Formula (I-R) that may be prepared by the procedures described above in Scheme XIV include: 2-(2-chlorophenyl)-1-(4-chlorophenyl)-5-(2,2-difluoropropyl)-1,6,7,8-tetrahydro-5H-1,3,5-triaza-azulen-4-one; 2-(2-chlorophenyl)-1-(4-chlorophenyl)-5-(2,2-trifluoroethyl)-1,6,7,8-tetrahydro-5H-1,3,5-triaza-azulen4-one; and 2-(2-chlorophenyl)-1-(4-chlorophenyl)-8,8-dimethyl-5-(2,2,2-trifluoroethyl)-1,6,7,8-tetrahydro-5H-1,3,5-triaza-azulen-4-one.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound or prodrug with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino ($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention contains an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$)alkanoyl, α-amino ($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$–$C_6$)alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$–$C_6$)alkyl or benzyl, —C(OY$_0$)Y$_1$ wherein Y$_0$ is ($C_1$–$C_4$) alkyl and Y$_1$ is ($C_1$–$C_6$) alkyl, carboxy($C_1$–$C_6$)alkyl, amino($C_1$–$C_4$)alkyl or mono-N— or di-N,N—($C_1$–$C_6$)alkylaminoalkyl, —C(Y$_2$)Y$_3$ wherein Y$_2$ is H or methyl and Y$_3$ is mono-N— or di-N, N—($C_1$–$C_6$)alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention also embraces isotopically-labeled compounds of the present invention (including intermediates) which are identical to those recited herein, but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" *J. Pharm. Pharmacol.*, 39, 769–773 (1987).

The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD including attention deficit hyperactivity disorder (ADHD)), Parkinson's disease, and type II diabetes.

Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, post-traumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y antagonists, thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, pseudoephedrine and peptide $YY_{3-36}$ or an analog thereof. Preferably, compounds of the present invention and combination therapies are administered in conjunction with exercise s and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and PYY$_{3-36}$ (including analogs) can be prepared as described in U.S. Publication No. 2002/0141985 and WO 03/027637. All of the above recited references are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)-NH$_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16–8714, ICI D7114, CL 316,243; phosphodiesterase inhibitors: L-386, 398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor (e.g., atorvastatin or the hemicalcium salt thereof), or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent will also be generally dependent upon a number of factors including the health of the subject being treated, the extent of treatment desired, the nature and kind of concurrent therapy, if any, and the frequency of treatment and the nature of the effect desired. In general, the dosage range of an anti-obesity agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert customary pharmaceutical excipient (or carrier) such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound of the present invention or the combination, may further comprise suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile condition with a pharmaceutically acceptable carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of pre-mix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

General Experimental Procedures

NMR spectra were recorded on a Varian Unity™ 400 (available from Varian Inc., Palo Alto, Calif.) at room temperature at 400 MHz for proton. Chemical shifts are expressed in parts per million ($\delta$) relative to residual solvent as an internal reference. The peak shapes are denoted as follows: s, singlet; d, doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line ($\lambda$=589 nm) at the indicated temperature and are reported as follows $[\alpha]_D^{temp}$, concentration (c=g/100 ml), and solvent.

Column chromatography was performed with either Baker™ silica gel (40 µm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

The 1,5-disubstituted 1H-pyrazole-3-carboxylic acid ester starting materials were prepared using procedures analogous to those described in U.S. Pat. No. 5,624,941 (Example No. 1) for the preparation of methyl 1-(2,4-dichlorophenyl)-5-(4-chlorophenyl)-1H-pyrazole-3-carboxylate.

The following section provides representative examples of useful intermediates that may be used in the synthesis of compounds of the present invention.

INTERMEDIATES

Preparation of Intermediate 4-Bromo-5-(4-chlorophenyl)-1-(2-chlorophenyl)-1H-pyrazole-3-carboxylic Acid Ethyl Ester (I-1a)

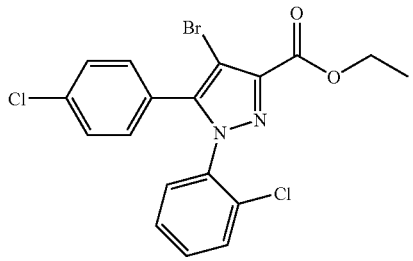

Bromine (15 ml, 294 mmol) was added in one portion to a cooled (ice/water bath) stirred solution of 5-(4-chlorophenyl)-1-(2-chlorophenyl)-1H-pyrazole-3-carboxylic acid ethyl ester (26.6 g, 73.6 mmol) in acetic acid (300 ml). After 45 minutes, the reaction was concentrated in vacuo, the solids slurried in diethyl ether (100 ml), filtered and dried in vacuo to afford the title compound (I-1a) as a light-yellow colored solid, 29.6 g.

Preparation of Intermediate 5-(4-Chlorophenyl)-1-(2-chlorophenyl)-4-vinyl-1H-,pyrazole-3-carboxylic Acid Ethyl Ester (I-1b)

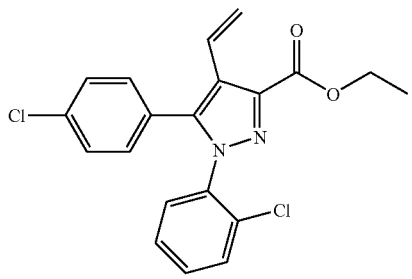

A solution of 4-bromo-5-(4-chlorophenyl)-1-(2-chlorophenyl)-1H-pyrazole-3-carboxylic acid ethyl ester I-1a (5.2 g, 11.9 mmol), tributylvinyltin (7.0 ml, 23.8 mmol) and tetrakistriphenylphosphine palladium (0.7 g, 0.6 mmol) in DMF (12 ml) was heated at 110° C. for 18 hours. The dark solution was cooled, partitioned between ethyl ether/water, the organic layer washed with brine, dried ($Na_2SO_4$) and concentrated in vacuo to afford a semi-solid. This semi-solid was stirred with cyclohexanes (35 ml) and filtered to afford the title compound (I-1b) as a white solid, 3.0 g.

Preparation of Intermediate 5-(4-Chlorophenyl)-1-(2-chlorophenyl)-4-formyl-1H-pyrazole-3-carboxylic Acid Ethyl Ester (I-1c)

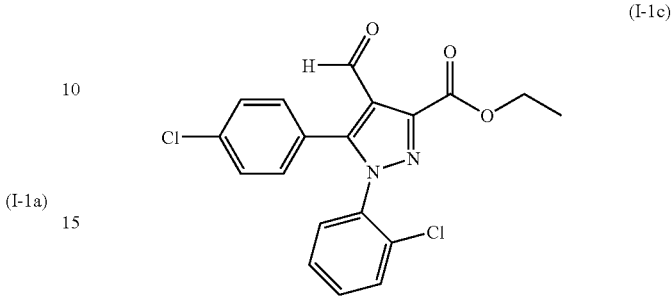

A solution of 5-(4-chlorophenyl)-1-(2-chlorophenyl)-4-vinyl-1H-pyrazole-3-carboxylic acid ethyl ester I-1b (2.9 g, 7.5 mmol), osmium tetroxide (8 mg, 0.08 mmol) and N-methylmorpholine-N-oxide (1.1 g, 8.2 mmol) in dioxane (24 ml)/water (6 ml) was stirred at ambient temperature for 18 hours, then sodium periodate (16 g, 75 mmol) was added and stirring was continued for 3.5 hours. The thick slurry was diluted with ethyl acetate (100 ml), filtered and solids washed 2× with ethyl acetate. The combined filtrates were washed with water, brine, dried ($Na_2SO_4$) and concentrated in vacuo to afford a solid mass. The solids were slurried in hot hexanes (30 ml), cooled, filtered and dried in vacuo to afford the title compound (I-1c) as a tan solid, 2.2 g.

Preparation of Intermediate 5-(4-Chlorophenyl)-1-(2-chlorophenyl)-4-hydroxy-1H-pyrazole-3-carboxylic Acid Ethyl Ester (I-1d)

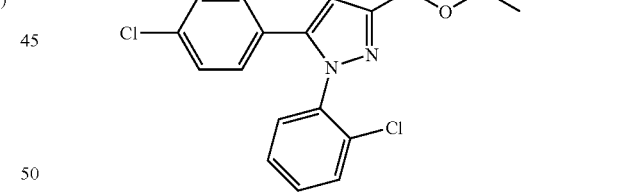

To a stirred solution of 5-(4-chlorophenyl)-1-(2-chlorophenyl)4-formyl-1H-pyrazole-3-carboxylic acid ethyl ester I-1c (2.2 g, 5.6 mmol) in dichloromethane (22 ml) was added m-chloroperbenzoic acid (2.9 g (50% purity), 8.4 mmol) and the resulting slurry was stirred for 6 hours. The mixture was diluted into ethyl ether, washed with half-saturated aqueous sodium bicarbonate, water, brine, dried ($Na_2SO_4$) and concentrated in vacuo to afford a yellow solid, 3.5 g. To a slurry of this material in methanol (20 ml), was added triethylamine (1 ml) to produce a solution. After 45 minutes, the reaction was concentrated in vacuo to afford a yellow solid. This material was purified by silica gel chromatograpy (Combiflash instrument, 120 g silica gel column, 5–25% gradient of ethyl acetate/hexanes to afford the title compound (I-1d) as a yellow solid, 1.5 g.

The following describes an alternative procedure for the preparation of Intermediate 5-(4-Chlorophenyl)-1-(2-chlorophenyl)4-hydroxy-1H-pyrazole-3-carboxylic Acid Ethyl Ester (I-1d).

Preparation of Intermediate 4-(4-Chlorophenyl)-3-oxo-butyric Acid Ethyl Ester (I-2a)

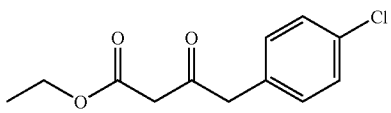
(I-2a)

To a cooled (0° C.), stirred solution of 2,2-dimethyl-1,3-doxane-4,6-dione (78.5 g, 0.54 mol) in dichloromethane (200 ml) was added pyridine (105 ml) dropwise over a 30-minute period. A solution of 4-chlorophenylacetyl chloride (100 g, 0.53 mol) in dichloromethane (150 ml) was added dropwise. The reaction mixture was stirred for 1hour at 0° C., then cooling bath was removed, and stirring was continued an additional 2 hours. Reaction mixture was poured over 2N hydrochloric acid (aq.)/ice, layers separated and the aqueous layer washed with dichloromethane (2×150 ml). Combined organic layers were washed with 2N hydrochloric acid (aq.) (2×150 ml), brine, dried (Na₂SO₄) and concentrated in vacuo to afford a solid.

The material obtained above was slurried in ethanol (1 liter), heated to reflux for 3 hours, then cooled and concentrated in vacuo. The oily residue was fractionally-distilled under vacuum to afford the title compound (I-1a) as a clear oil, 108 g.

Preparation of Intermediate 4-(4-Chlorophenyl)-2-[(2-chlorophenyl)-hydrazono]-3-oxobutyric Acid Ethyl Ester (I-2b)

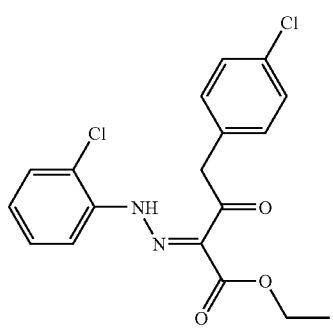
(I-2b)

A solution of sodium nitrite (3.4 g, 50.4 mmol) in water (15 ml) was added dropwise over an hour period to a cooled (0° C.), stirred solution of 2-chloroaniline (6.4 g, 50.4 mmol) in acetic acid (50 ml)/water (7 ml). Then a solution of 4-(4-chloro-phenyl)-3-oxo-butyric acid ethyl ester (10 g, 42 mmol) in acetic acid (30 ml) was added dropwise over a 30-minutes period to produce an orange slurry (20 ml of water added to aid stirring). After an additional hour, the mixture was filtered, solids washed with water and air-dried. Solids slurried in ethanol (75 ml) for 30 minutes, filtered, solids washed with methanol and dried in vacuo to afford the title compound (I-2b) as an orange solid, 11.0 g.

Preparation of 4-Bromo-4-(4-chlorophenyl)-2-[(2-chlorophenyl)-hydrazono]-3-oxobutyric Acid Ethyl Ester (I-2c)

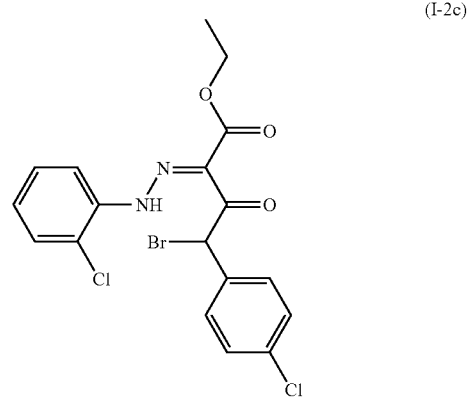
(I-2c)

A stirred slurry of 4-(4-chlorophenyl)-2-[(2-chlorophenyl)-hydrazono]-3-oxobutyric acid ethyl ester I-2b (10.0 g, 26 mmol) and copper(II) bromide (13.4 g, 59.8 mmol) in ethyl acetate (100 ml)/chloroform (100 ml) was heated at 60° C. for 3 hours. Reaction mixture cooled and filtered through diatomaceous earth washing with chloroform. The filtrate was diluted with dichloromethane, washed with water, brine, dried (Na₂SO₄) and concentrated in vacuo to afford the title compound (I-2c) as a red oil, 12.1 g.

Preparation of intermediate 5-(4-Chlorophenyl)-1-(2-chlorophenyl)-4-hydroxy-1H-pyrazole-3-carboxylic Acid Ethyl Ester (I-1d)

A mixture of 4-bromo4-(4-chloro-phenyl)-2-[(2-chlorophenyl)-hydrazono]-3-oxo-butyric acid ethyl ester (12.1 g, 26 mmol) and sodium acetate (10.8 g, 130 mmol) in methanol (100 ml) was heated at reflux for 4 hours, cooled, concentrated in vacuo and the residue partitioned between ethyl acetate and water. The organic layer was washed with brine, dried (Na₂SO₄) and concentrated in vacuo to afford a solid. A slurry of this material in cyclohexane was heated to reflux and allowed to stir at ambient temperature for 2 hours, and filtered to afford the title compound (I-1d) as a yellow solid (I-1d), 6.5 g.

Preparation of Intermediate 4-Allyloxy-5-(4-chlorophenyl)-1-(2-chlorophenyl)-1H-pyrazole-3-carboxylic Acid Ethyl Ester (I-1e)

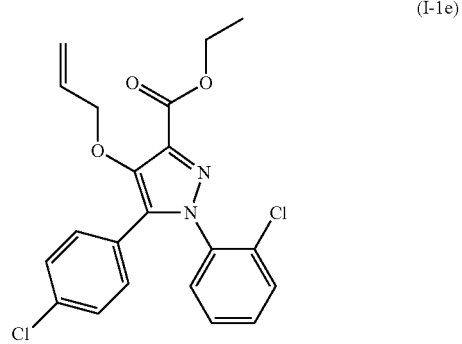
(I-1e)

To a slurry of sodium hydride (39 mg of 60% in oil) in DMSO (2.4 ml) was added 5-(4-chlorophenyl)-1-(2-chlorophenyl)-4-hydroxy-1H-pyrazole-3-carboxylic acid ethyl ester I-1d (300 mg, 0.8 mmol) and the mixture was agitated for 45 minutes. Allyl bromide (0.1 ml, 1.2 mmol) was added and stirring was continued for 4.5 hours. The reaction solution was diluted into ethyl acetate, washed with water (2×), brine, dried (Na$_2$SO$_4$) and concentrated in vacuo to afford the title compound (I-1e) as an orange oil, 340 mg. This material was taken onto the next step without further purification.

Preparation of Intermediate 5-(4-Chlorophenyl)-1-(2-chlorophenyl)-4-(2-oxoethoxy)-1H-pyrazole-3-carboxylic Acid Ethyl Ester (I-1f)

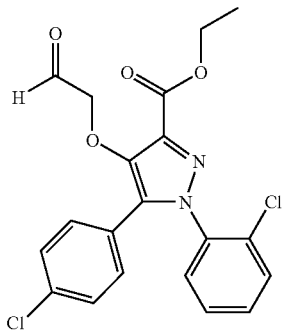

(I-1f)

To a stirred solution of 4-allyloxy-5-(4-chlorophenyl)-1-(2-chlorophenyl)-1H-pyrazole-3-carboxylic acid ethyl ester I-1e (337 mg, 0.8 mmol) osmium tetroxide (53 microliters of a 0.15 M solution in water) and N-methylmorpholine-N-oxide (120 mg, 0.9 mmol) in dioxane (2.4 ml)/water (0.6 ml) was stirred at ambient temperature for 18 hours, then sodium periodate (1.7 g, 8.1 mmol) was added and stirring was continued for 3.5 hours. The thick slurry was diluted with ethyl acetate (100 ml), filtered and solids washed 2× with ethyl acetate. The combined filtrates were washed with water, brine, dried (Na$_2$SO$_4$) and concentrated in vacuo to afford an oil. Silica gel chromatography (25% ethyl acetate/hexanes) afforded the title compound (I-1f) as a colorless foam, 130 mg.

Preparation of Intermediate 5-(4-Chlorophenyl)-1-(2-chlorophenyl)-4-[2-(2,2,2-trifluoroethylamino)-ethoxy]-1H-pyrazole-3-carboxylic Acid Ethyl Ester (I-1g)

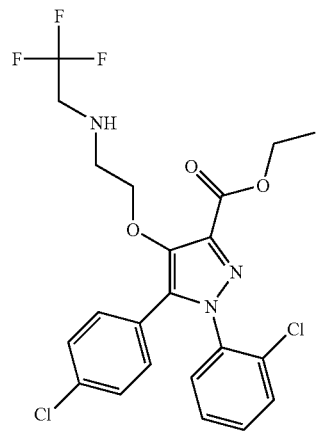

(I-1g)

A solution of 5-(4-chlorophenyl)-1-(2-chlorophenyl)-4-(2-oxoethoxy)-1H-pyrazole-3-carboxylic acid ethyl ester I-1f (40 mg, 0.1 mmol), 2,2,2-trifluoroethylamine (14 mg, 0.14 mmol), sodium triacetoxyborohydride (30 mg, 014 mmol) and acetic acid (6 microliters, 0.1 mmol) in 1,2-dichloroethane (0.5 ml) was stirred for 18 hours. The reaction was partitioned between ethyl acetate/saturated aqueous sodium bicarbonate, the organic layer was dried (Na$_2$SO$_4$) and concentrated in vacuo to afford the title compound (I-1g). This oil was taken on to the next step without further purification.

Preparation of Intermediate 5-(4-Chlorophenyl)-1-(2-chlorophenyl)-4-[2-(2,2,2-trifluoroethylamino)-ethoxy]-1H-pyrazole-3-carboxylic Acid, Hydrochloride (I-1h)

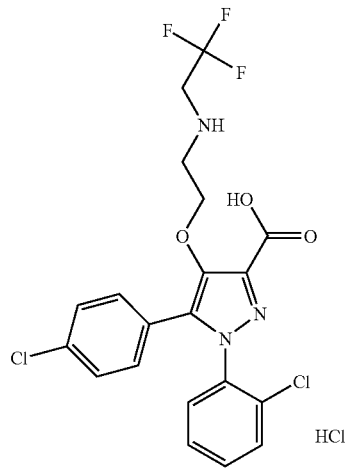

(I-1h)

A solution of 5-(4-chlorophenyl)-1-(2-chlorophenyl)-4-[2-(2,2,2-trifluoroethylamino)-ethoxy]-1H-pyrazole-3-carboxylic acid ethyl ester I-1g (48 mg, 0.1 mmol) and 6 N aqueous KOH (0.1 ml) in ethanol (1 ml) was heated at 50° C. for 2 hours. The reaction solution was cooled, acidified with concentrated aqueous hydrochloric acid, and concentrated in vacuo to a solid. These solids were slurried with ethanol, filtered and the remaining mass was washed with additional portions (2×) of ethanol. The combined filtrates were concentrated in vacuo to afford the title compound (I-1h), which was taken on the next step without further purification.

Preparation of Intermediate 2,2-Difluoro-propionic acid ethyl ester (I-3a)

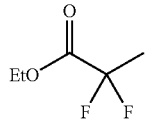

(I-3a)

(Diethylamino)sulfur trifluoride (125 g, 780 mmol) was added dropwise to stirred, cooled (0° C.) ethyl pyruvate (71 ml, 650 mmol). The reaction was allowed to warm to ambient temperature overnight, then quenched by slowly pouring over an ice/water mixture and extracted with diethyl ether. The organic phase was washed with brine, dried (Na₂SO₄) and concentrated in vacuo. The resulting oil was fractionally distilled at ambient pressure (110–115° C.) to afford the title compound (I-3a) as a colorless oil, 55.6 gm.

Preparation of Intermediate 2,2-Difluoro-N-(2-hydroxy-ethyl)-propionamide (I-3b)

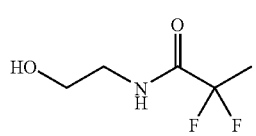

2,2-Difluoro-propionic acid ethyl ester I-3a (10.1 g, 70 mmol) was added dropwise to stirred, cooled (0° C.) ethanolamine (4.4 ml, 70 mmol) and the resulting solution was allowed to stir at ambient temperature for 4 hours. Concentration of the reaction mixture in vacuo afforded the title compound (I-3b) as a solid, 11.2 g.

Preparation of Intermediate 2-(2,2-Difluoro-propylamino)-ethanol (I-3c)

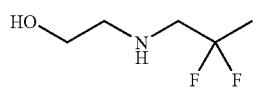

To a stirred solution of lithium aluminum hydride (5.5 g, 146 mmol) in diethyl ether (85 ml) was added a solution of 2,2-difluoro-N-(2-hydroxy-ethyl)-propionamide (11.2 g, 73 mmol) in diethyl ether (55 ml) dropwise at such a rate to maintain a gentle reflux. After an additional 1.5 hours, the reaction was quenched with sodium sulfate decahydrate, diluted with ethyl acetate and allowed to stir for 18 hours. The mixture was filtered with the aid of diatomaceous earth, washing with ethyl acetate. The filtrate was concentrated in vacuo and fractionally distilled (11 torr, collecting fractions distilling at 75–88° C.) to afford the title compound (I-3c) as a colorless oil, 4.5 g.

Preparation of Intermediate 1-(2-Chloro-phenyl)-5-(4-chloro-phenyl)-4-hydroxy-1H-pyrazole-3-carboxylic acid (2,2-difluoro-propyl)-(2-hydroxy-ethyl)-amide (I-3d)

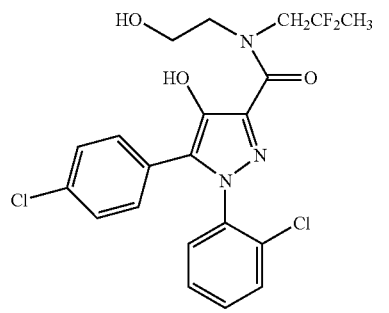

A stirred mixture of 1-(2-chloro-phenyl)-5-(4-chloro-phenyl)-4-hydroxy-1H-pyrazole-3-carboxylic acid ethyl ester I-3c (15 g, 40 mmol) and 2-(2,2-difluoro-propylamino)-ethanol (16.5 g, 120 mmol) were heated at 125° C. for 18 hours. The reaction solution was cooled, diluted into ethyl acetate, washed with 1 N aq. HCl, brine, dried (Na₂SO₄) and concentrated in vacuo. The resulting oil was chromatographed on silica gel (20% to 40% ethyl acetate/hexanes) to afford the title compound (I-3d) as an oil, 10 g.

Preparation of Intermediate 4-Amino-1-(2-chlorophenyl)-5-(4-chlorophenyl)-1H-pyrazole-3-carboxylic Acid Ethyl Ester (I-4a)

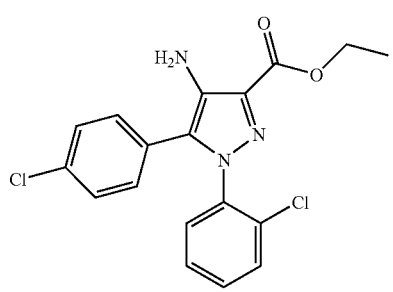

To a solution of LiN(TMS)₂ (1.0 M in THF, 100 ml, 100 mmol) in 400 ml diethyl ether at −78° C. under nitrogen, 1-(4-chlorophenyl)ethanone (14.3 ml, 110 mmol) in 80 ml ether was added dropwise via addition funnel. After the addition was complete, the reaction mixture was stirred at −78° C. for 40 minutes. Oxalic acid diethyl ester (14.3 ml, 105 mmol) was added in one portion via syringe. The reaction mixture was warmed to room temperature and stirred overnight. The pale white precipitate that formed was collected by filtration. The solid was dried in vacuo to give 4-(4-chlorophenyl)-2-hydroxy-4-oxobut-2-enoic acid ethyl ester lithium salt (24.0 g, 92%).

A portion of the product from the previous step (10 g, 38.37 mmol) was dissolved in 400 ml acetic acid. After the solution was cooled to 10° C. with an ice-water bath, a concentrated aqueous solution of sodium nitrite (2.86 g, 40.29 mmol) was added dropwise, keeping the temperature between 10° and 15° C. The reaction mixture was stirred for another 45 minutes, and 2-chlorophenylhydrazine HCl salt (8.5 g, 46.04 mmol) was added in portions. Stirring was continued for 3 hours. Upon completion of the reaction, the reaction mixture was poured into 600 ml ice-cold water. A yellow solid precipitated and after 2 hours it was collected, washed with water and dried to give crude 4-(4-chlorophenyl)-2-[(2-chlorophenyl)hydrazono]-3-nitroso4-oxobutyric acid ethyl ester which was used in the next step without further purification.

The yellow solid obtained from last step was redissolved into i-PrOH and 1 ml concentrated H$_2$SO$_4$ was added. The reaction mixture was heated to 60° C. for 3 hours. After cooling to room temperature, the reaction mixture was poured into ice-NaHCO$_3$ (saturated aqueous). The precipitate was collected by filtration and dried to give 1-(2-chlorophenyl)-5-(4-chlorophenyl)-4-nitroso-1H-pyrazole-3-carboxylic acid ethyl ester. It was used for next step without further purification.

The product obtained from the last step was dissolved in 200 ml of ethyl acetate and 200 ml of water. Sodium dithionite was added until the disappearance of 1-(2-chlorophenyl)-5-(4-chlorophenyl)-4-nitroso-1H-pyrazole-3-carboxylic acid ethyl ester was confirmed by TLC (ethyl acetate/hexane, 50/50). Then the organic layer was separated and the aqueous layer was extracted with ethyl acetate. The combined organic layers were dried over magnesium sulfate and the solvent was removed in vacuo. The red solid obtained was further purified by plug filtration (silica, ethyl acetate/hexane, 50/50) to give 4-amino-1-(2-chlorophenyl)-5-(4-chlorophenyl)-1H-pyrazole-3-carboxylic acid ethyl ester I-4a (21.86 g, 76%). MS: 376.1 (M+1)$^+$.

Preparation of Intermediate 4-(2-tert-Butoxycarbonylaminoethylamino)-1-(2-chlorophenyl)-5-(4-chlorophenyl)-1H-pyrazole-3-carboxylic Acid Ethyl Ester (I-4b)

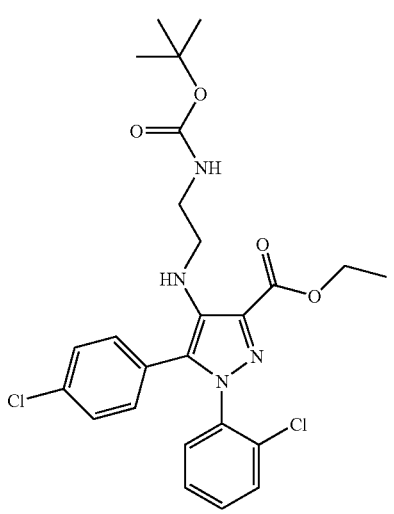

(I-4b)

To a solution of 4-amino-1-(2-chlorophenyl)-5-(4-chlorophenyl)-1H-pyrazole-3-carboxylic acid ethyl ester (I-4a, 1.88 g, 5 mmol) and (2-oxo-ethyl)-carbamic acid tert-butyl ester (1590 mg, 10 mmol) in 1,2-dichloroethane (60 ml) at room temperature was added glacial acetic acid (858 microliters, 15 mmol) and NaBH(OAc)$_3$ (2540 mg, 12 mmol). The reaction mixture was stirred for 23 hours, then additional (2-oxo-ethyl)-carbamic acid tert-butyl ester (500 mg, 3.14 mmol) and NaBH(OAc)$_3$ (1000 mg, 4.7 mmol) were added. The reaction mixture was stirred for an additional 24 hours, quenched with 1 N NaOH, and diluted with CH$_2$Cl$_2$. The organic layer was separated and the aqueous layer extracted with CH$_2$Cl$_2$. The combined organic phases were washed with 0.5 M aqueous citric acid, 1 N NaOH, and saturated aqueous NaCl, dried, and concentrated in vacuo. The crude residue was purified on a Biotage 40+M column using CH$_2$Cl$_2$/MeOH (100:1) to give the desired product I-4b (900 mg): +ES MS (M+1) 519.5.

Preparation of Intermediate 4-(2-tert-Butoxycarbonylaminoethylamino)-1-(2-chlorophenyl)-5-(4-chlorophenyl)-1H-pyrazole-3-carboxylic Acid (I-4c)

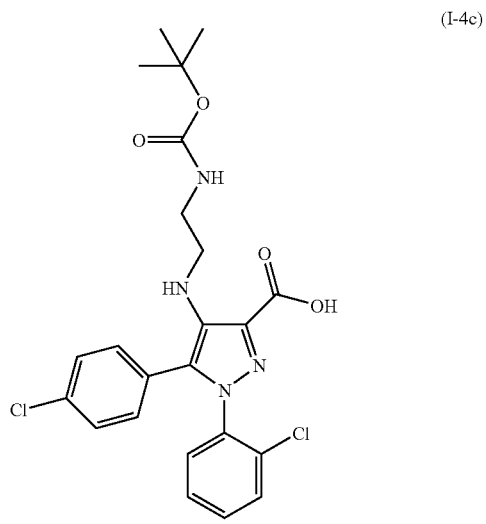

(I-4c)

To a solution of 4-(2-tert-butoxycarbonylaminoethylamino)-1-(2-chlorophenyl)-5-(4-chlorophenyl)-1H-pyrazole-3-carboxylic acid ethyl ester (I-4b, 900 mg) in ethanol (50 ml) at room temperature was added 1 N KOH (25 ml). The reaction mixture was heated at 50° C. for 2 hours, cooled to room temperature, diluted with saturated aqueous NaCl, and acidified to pH 3 with 3N HCl. The aqueous solution was extracted with EtOAc (2×) and the combined organic extracts were dried and concentrated in vacuo to give the product I-4c as an amorphous glass (879 mg): +ES MS (M+1) 491.5.

Preparation of Intermediate 4-(2-Aminoethylamino)-1-(2-chlorophenyl)-5-(4-chlorophenyl)-1H-pyrazole-3-carboxylic Acid (I-4d)

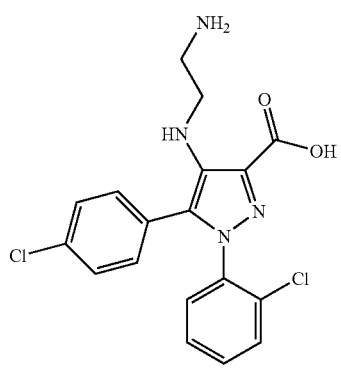

(I-4d)

A solution of 4-(2-tert-butoxycarbonylaminoethylamino)-1-(2-chlorophenyl)-5-(4-chlorophenyl)-1H-pyrazole-3-carboxylic acid (I-4c, 879 mg) in 2:1 conc HCl/EtOH (12 ml) was allowed to stand at room temperature for 17 hours. The reaction mixture was concentrated under vacuum to give the desired product I-4d: +ES MS (M+1) 391.4.

Preparation of Intermediate 3-(4-Chlorophenyl)-2-(2-chlorophenyl)-4,5,6,7-tetrahydro-2H-pyrazolo[4,3-e][1,4]diazepin-8-on (I-4e)

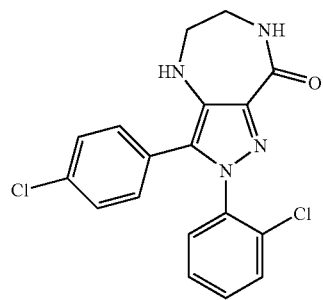

(I-4e)

Diisopropylethylamine (209 microliters, 1.2 mmol) was added slowly via syringe to a solution of 4-(2-aminoethylamino)-1-(2-chlorophenyl)-5-(4-chlorophenyl)-1H-pyrazole-3-carboxylic acid (I-4d, 228 mg, 0.53 mmol) and HATU (456 mg, 1.2 mmol) in anhydrous DMF (30 ml) at room temperature. The reaction mixture was stirred for 17 hours, diluted with saturated aqueous NaCl, and extracted with EtOAc (2×). The combined EtOAc extracts were washed with 0.5 M citric acid, 1 M K$_2$CO$_3$, and saturated aqueous NaCl, dried and concentrated in vacuo. The residue was slurried with CH$_2$Cl$_2$ and the organic solvent decanted, a process that was repeated twice. The combined organic solutions were concentrated in vacuo and the residue was purified on a chromatotron using 4 mm plates and a solvent gradient of 100% EtOAc to 10:1 EtOAC/MeOH to give I-4e as a colorless solid (82 mg): +ES MS (M+1) 373.4.

Preparation of 3-(4-Chlorophenyl)-2-(2-chlorophenyl)-4-trifluoroacetyl-4,5,6,7-tetrahydro-2H-pyrazolo[4,3-e][1,4]diazepin-8-one (I-4f)

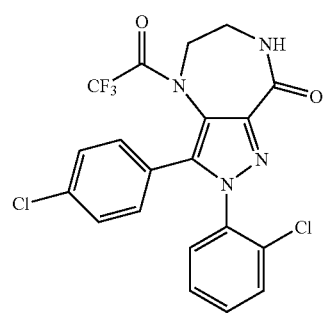

(I-4f)

To a solution of 3-(4-chlorophenyl)-2-(2-chlorophenyl)-4,5,6,7-tetrahydro-2H-pyrazolo[4,3-e][1,4]diazepin-8-on (I-4e, 49 mg, 0.13 mmol) and NEt$_3$ (21 microliters, 0.15 mmol) in 1,2-dichloroethane (1.5 ml) at 0° C. was slowly added triflic anhydride (20 microliters, 0.144 mmol). The reaction mixture was allowed to warm to room temperature and stir for 1 hour. Removal of an aliquot for analysis via APCl mass spectrometry revealed only starting material present. Additional NEt$_3$ (31 mg) and triflic anhydride (50 mg) were added. The reaction mixture was stirred at room temperature for 1 hour and then was diluted with saturated aqueous NaCl. The organic layer was separated and the aqueous layer was extracted twice with CH$_2$Cl$_2$. The combined organic extracts were washed with 0.5 M citric acid, 1 M K$_2$CO$_3$, and saturated aqueous NaCl, dried, and concentrated in vacuo. The crude residue was purified via a chromatotron using 1 mm plates and 100% EtOAc as solvent to give I-4f (45 mg): +ES MS (M+1) 469.2.

Preparation of (L)-4-[(1-tert-Butoxycarbonyl-pyrrolidin-2-ylmethyl)-amino]-1-(2-chlorophenyl)-5-(4-chlorophenyl)-1H-pyrazole-3-carboxylic Acid Ethyl Ester (I-5a)

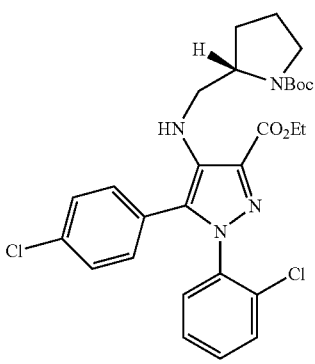

(I-5a)

Glacial acetic acid (57 microliters, 1 mmol) and NaBH(OAc)$_3$ (318 mg, 1.5 mmol) were added to a solution of 4-amino-1-(2-chlorophenyl)-5-(4-chlorophenyl)-1H-pyrazole-3-carboxylic acid ethyl ester (376 mg, 1 mmol) and (L)-2-formyl-pyrrolidine-1-carboxylic acid tert-butyl ester (N-Boc-L-prolinal, 239 mg, 1.2 mmol) at room temperature in 1,2-dichloroethane (10 ml). The reaction mixture was stirred for 17 hours and quenched with 1 M NaOH (0.5 ml). The organic layer was separated and the aqueous layer extracted once with CH$_2$Cl$_2$. The combined organic solution was washed with saturated aqueous NaCl, dried, and concentrated in vacuo. The residue was purified on a chromatotron using 4 mm plates and a solvent gradient of 100% CH$_2$Cl$_2$ to 20:1 CH$_2$Cl$_2$/MeOH to give the desired product I-5a as a colorless white oil (207 mg): +ES MS (M+1) 559.5.

Preparation of 1-(2-Chlorophenyl)-5-(4-chlorophenyl)-4-[(pyrrolidin-2-ylmethyl)-amino]-1H-pyrazole-3-carboxylic Acid (I-5b)

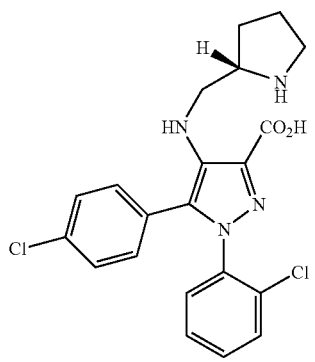

(I-5b)

A solution of (L)-4-[(1-tert-butoxycarbonyl-pyrrolidin-2-ylmethyl)-amino]-1-(2-chlorophenyl)-5-(4-chlorophenyl)-1H-pyrazole-3-carboxylic acid ethyl ester (I-5a, 207 mg, 0.37 mmol) in 2:1 EtOH/1 N KOH (6 ml) was stirred at 50° C. for 2 hours. After cooling to room temperature, the reaction mixture was acidified with conc. HCl (~2 ml), stirred for 4 hours, and concentrated under vacuum to give I-5b as a white solid: +ES MS (M+1) 431.4.

Preparation of 4-(4-chlorophenyl)-2-hydroxy-4-oxo-but-2-enoic acid ethyl ester lithium salt (I-6a)

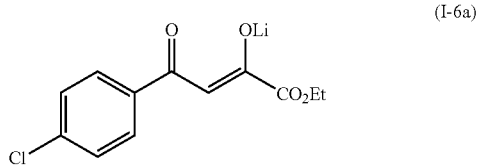

(I-6a)

To tert-butyl methyl ether (350 ml) was added 149 ml of lithium bis(trimethylsilyl)-amide (1.0 M in tetrahydrofuran, 149 mmol) at room temperature. The resulting solution was cooled to −75° C. 1-(4-chlorophenyl) ethanone (23.28 g, 150.6 mmoles) was added as a solution in 23 ml of tert-butyl methyl ether over 3 minutes, keeping internal temperature less than −70° C. The reaction solution was held for 1 hour at −75° C., then diethyl oxalate (22.0 g, 150 mmol) was added neat over 5 minutes keeping internal temperature less than −70° C. The clear dark orange reaction solution was warmed to room temperature over 4 hours. Note: Product began to precipitate at −3° C. The reaction was allowed to stir for 15 hours at room temperature, followed by isolation of precipitated product by filtration. The filtercake was washed with 100 ml of room temperature tert-butyl methyl ether and then dried at 60° C. and 10 mm for 1 hour to give 4-(4-chlorophenyl)-2-hydroxy-4-oxo-but-2-enoic acid ethyl ester lithium salt I-6a (36.72 g, 94%) as a powdery yellow solid.

$^1$H-NMR (DMSO-$d_6$) δ 7.80 (d, 1.94H, J=8.7 Hz), 7.66 (d, 0.06H, J=8.7 Hz), 7.43 (d, 1.94H, J=8.7 Hz), 7.31 (d, 0.06H, J=8.3 Hz), 6.37 (s, 0.97H), 5.22 (s, 0.03H), 4.10 (q, 1.94H, J=7.05 Hz), 4.00 (q, 0.06H, J=7.05 Hz), 1.20 (t, 2.91H, J=7.05 Hz), 1.15 (t, 0.09H, J=7.05 Hz). Shows a 97:3 mixture of geometric isomers. Mass Spec (ESI): M+1=255.2 (mass of neutral compound)

Preparation of 1-(2-chlorophenyl)-5-(4-chlorophenyl)-1H-pyrazole-3-carboxylic acid (I-6b)

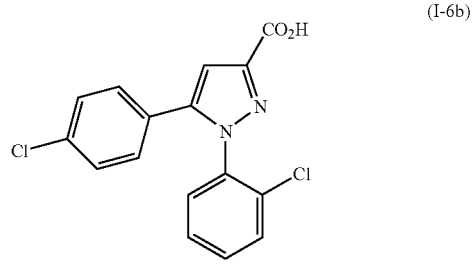

(I-6b)

4-(4-Chlorophenyl)-2-hydroxy-4-oxo-but-2-enoic acid ethyl ester lithium salt I-6a (30.26 g, 116 mmoles) was suspended in 242 ml of ethanol. 2-Chlorophenylhydrazine hydrochloride (20.88 g, 116 mmoles) was added portionwise as a solid over 45 minutes while maintaining an internal temperature between 30–40° C. Note: Reaction mixture goes from a yellow suspension to a dark orange suspension. Reaction stirred for 3 hours while maintaining internal temperature between 25–35° C. An aqueous potassium hydroxide solution (148 ml of 1.8 M solution, 266 mmoles) was added over 20 minutes while maintaining an internal temperature between 20–30° C. The reaction mixture was held for 2.5 hours. Note: Within 30 minutes of potassium hydroxide solution addition, reaction turned almost clear, very dark rust orange in color. Aqueous hydrochloric acid (85 ml of 3.9 M solution, 331 mmoles) was added over 15 minutes while maintaining reaction temperature between 20–30° C. Note: Product precipitated during hydrochloric acid addition. The precipitated product was granulated for 16 hours at room temperature. The crude product was isolated by filtration and the filtercake was washed with 150 ml of water. Note: Filtercake was a yellowish orange solid. After air-drying for 30 minutes, the filtercake was suspended in 480 ml of methanol. This suspension was heated to reflux to give a clear dark orange solution (all solids in solution within 1 hour of reaching reflux) that was held at reflux for 8 hours. The solution was cooled over 4 hours to room temperature, during which time product had precipitated from solution. The reaction mixture was held at room temperature for 10 hours, followed by cooling to 0° C., and stirring for 1.5 hours. Collection of the precipitate by filtration, washing the resulting filtercake with 150 ml of ice-chilled methanol, and drying at 60° C. and 1 mm for 3 hours afforded 1-(2-chlorophenyl)-5-(4-chlorophenyl)-1H-pyrazole-3-carboxylic acid I-6b (29.28 g, 76%) as an off-white solid.

$^1$H-NMR (CD$_3$CN): δ 7.58–7.45 (m, 4H), 7.31 (d, 2H, J=8.7 Hz), 7.21 (d, 2H, J=8.7 Hz), 7.10 (s, 1H). Mass Spec (ESI): M+1=333.2

Preparation of 1-(2-chlorophenyl)-5-(4-chlorophenyl)-4-hydroxy-1H-pyrazole-3-carboxylic acid (I-6c)

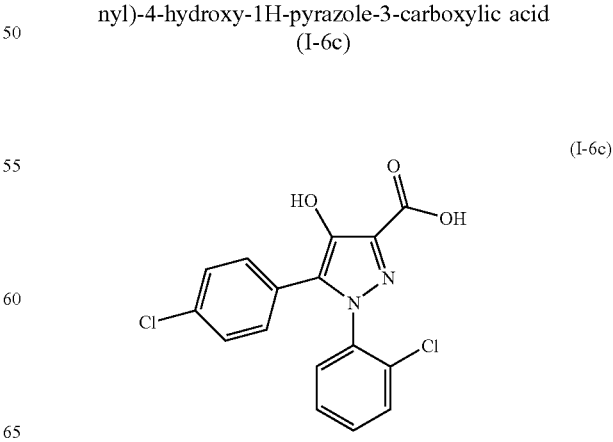

(I-6c)

1-(2-Chlorophenyl)-5-(4-chlorophenyl)-1H-pyrazole-3-carboxylic acid I-6b (628.1 g, 1.88 mol) was dissolved in tetrahydrofuran (11 liters) to give a clear light orange solution. This solution was cooled to −78° C. followed by the addition of hexyllithium (2.0 M solution in hexanes, 2.07 liters, 4.14 mol) over a period of 2 hours while keeping internal temperature less than −70° C. Note: During addition of the first equivalent of hexyllithium, reaction solution remained clear orange, then during addition of second equivalent of hexyllithium, reaction solution turned brown and then very dark green. Reaction mixture held for 20 minutes at −74° C., then warmed to −50° C. over 30 minutes and held for 1hour at this temperature. The reaction was cooled back to less than −70° C., followed by the addition of neat trimethylborate (238 g, 2.01 moles) over 3 minutes while keeping temperature less than −68° C. The reaction solution was then warmed to room temperature over 3 hours. Note: Reaction remained very dark green until reaching room temperature where it turned clear dark orange. Aqueous sodium hydroxide (750 mL of 3.0 M, 2.25 mol) was added over 5 minutes to crude reaction solution while maintaining an internal temperature of 10–15° C. Concentrated aqueous hydrogen peroxide (253 g, 30 wt %, 2.01 moles) was then added over a period of 30 minutes while maintaining an internal temperature between 10–20° C. The reaction was allowed to warm to room temperature and stirred for 3.5 hours. Water (3 liters) was added followed by addition of concentrated aqueous hydrochloric acid (545 ml, 12.1 M, 6.59 mol) over 15 minutes while maintaining a temperature of 20–30° C. Note: pH of crude reaction solution is ~2.5. The tetrahydrofuran and aqueous layers were separated and the aqueous layer was extracted with 4 liters of tert-butyl methyl ether. The tetrahydrofuran and tert-butyl methyl ether layers were combined, washed with 4 liters of brine, and dried over 2.5 Kg of $Na_2SO_4$. The crude solution was concentrated in vacuo to a thick orange oil containing some fine solids. The crude orange oil was then added to 5 liters of methanol, causing a bright yellow precipitate to crystallize from solution. The precipitated product was granulated for 20 hours at room temperature followed by cooling to 0° C. and stirring for 1 hour. The crude product was isolated by filtration and the resulting filtercake was washed with 1 liter of ice-chilled methanol. The filtercake was air-dried for 18 hours. This crude product (390 g) was suspended in 2.1 liters of 2-propanol followed by heating to reflux to give a clear yellow/orange solution. Solution held at reflux for 1 hour, then cooled over a period of 5 hours to 3° C. and stirred for 1 hour. The recrystallized product was isolated by filtration and the resulting filtercake was washed with 900 ml of ice-chilled 2-propanol, followed by air-drying for 18 hours. The product was oven-dried for 18 hours at 60° C. and 10 mm to afford 1-(2-chlorophenyl)-5-(4-chlorophenyl)-4-hydroxy-1H-pyrazole-3-carboxylic acid I-6c (282.9 g, 43%) as an off-white solid.

$^1$H-NMR (CD$_3$CN): δ 7.55–7.44 (m, 4H), 7.31 (d, 2H, J=8.7 Hz), 7.20 (d, 2H, J=8.7 Hz). Mass Spec (ESI): M+1=349.2

Preparation of 4-Acetoxy-1-(2-chlorophenyl)-5-(4-chlorophenyl)-1H-pyrazole-3-carboxylic acid (I-6d)

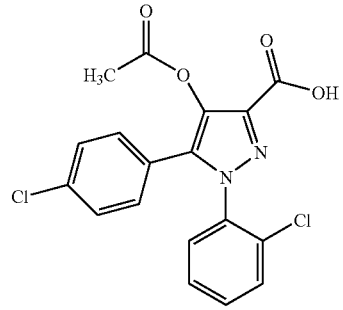

(I-6d)

1-(2-Chlorophenyl)-5-(4-chlorophenyl)-4-hydroxy-1H-pyrazole-3-carboxylic acid I-6c (572.0 g, 1.64 mol) was combined with 8 liters of methylene chloride to give an off-white suspension. N,N-Diisopropylethylamine (427.9 g, 3.29 mol) was added over 15 minutes while keeping the temperature between 20–25° C. A clear yellow solution resulted. Acetic anhydride (334.5 g, 3.24 mol) was added over 5 minutes keeping the temperature between 20–25° C. The reaction was stirred at room temperature for 16 hours. The crude reaction solution was washed twice with 4 liters portions of 0.5 M citric acid and once with 4 liters of brine. The crude solution was concentrated in vacuo to a total volume of 1 liter. This milky suspension was then added to 4 liters of hexanes causing the desired product to precipitate instantly. The solids were granulated for 30 minutes and then collected by filtration. The filtercake was rinsed with 3 liters of hexanes and then air-dried for 16 hours. The isolated product was then further dried at 60° C. and 8 mm for 2 hours. 4-Acetoxy-1-(2-chlorophenyl)-5-(4-chlorophenyl)-1H-pyrazole-3-carboxylic acid I-6d (601.6 g, 94%) was isolated as a powdery, off-white solid.

$^1$H-NMR (CD$_2$Cl$_2$): δ 7.50 (d, 1H, J=7.0 Hz), 7.47–7.37 (m, 3H), 7.28 (d, 2H, J=8.7 Hz), 7.12 (d, 2H, J=8.7 Hz), 2.26 (s, 3H). Mass Spec (ESI): M+1=391.2

Preparation of Acetic acid 1-(2-chlorophenyl)-5-(4-chlorophenyl)-3-[(2,2-difluoro-propyl)-(2-hydroxy-ethyl)-carbamoyl]-1H-pyrazol-4-yl ester (I-6e)

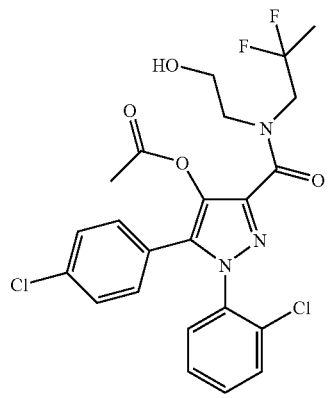

(I-6e)

4-Acetoxy-1-(2-chlorophenyl)-5-(4-chlorophenyl)-1H-pyrazole-3-carboxylic acid I-6d (581.0 g, 1.48 mol) was dissolved in 10 liters of methylene chloride to give a pale yellow, slightly opaque solution. The solution was filtered through Celite® to give a clear green colored solution. 2-Chloro-4,6-dimethoxy-1,3,5-triazine (296.8 g, 1.64 mol) was added in one portion as a solid at room temperature to give an opaque suspension (addition is slightly endothermic). 4-Methylmorpholine (182.9 g, 1.80 mol) was added over 15 minutes while keeping the temperature between 18–22° C. (reaction returned to being yellow in color). Reaction stirred for 3 hours at room temperature, then 2-(2,2-difluoropropylamino)-ethanol (228.3 g, 1.64 mol) was added neat over 10 minutes while keeping the temperature between 20–25° C. The reaction was stirred for 15 hours, then washed twice with 6 liter portions of 10% citric acid and once with 5 liters of brine. The crude product solution was concentrated in vacuo to a thick orange oil, then reconstituted in 4 liters of isopropyl ether. After removing 1 liter of distillates precipitate began to form. To the crude product suspension was added 1.5 liters of isopropyl ether and then the mixture was stirred at room temperature for 1 hour. The precipitated solids were collected by filtration and the resulting filtercake was rinsed with 2 liters of room temperature isopropyl ether, followed by air-drying for 16 hours. Acetic acid 1-(2-chlorophenyl)-5-(4-chlorophenyl)-3-[(2,2-difluoro-propyl)-(2-hydroxyethyl)-carbamoyl]-1H-pyrazol-4-yl ester I-6e (603.0 g, 78%) was isolated as a granular off-white solid.

$^1$H-NMR (CD$_2$Cl$_2$): δ 7.50–7.31 (m, 4H), 7.28 (d, 2H, J=8.3 Hz), 7.14 (d, 2H, J=8.7 Hz), 4.41–3.41 (m, various rotamers, 7H), 2.21 (s, 3H), 1.65 (t, 3H, J$_{HF}$=19.5 Hz). Mass Spec (ESI): M+1=512.2

Preparation of Acetic acid 3-[(2-chloroethyl)-(2,2-difluoropropyl)-carbamoyl]-1-(2-chlorophenyl)-5-(4-chlorophenyl)-1H-pyrazol-4-yl-ester (I-6f)

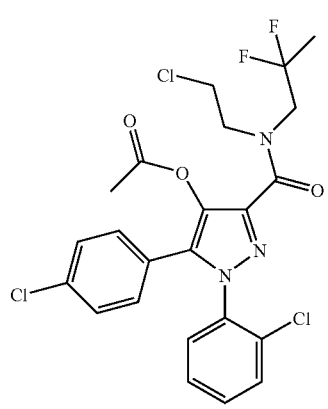

(I-6f)

Method A: Acetic acid 1-(2-chlorophenyl)-5-(4-chlorophenyl)-3-[(2,2-difluoro-propyl)-(2-hydroxy-ethyl)-carbamoyl]-1H-pyrazol-4-yl ester I-6e (580.6 g, 1.12 mol) was dissolved in 10 liters of methylene chloride to give a clear pale yellow solution. After cooling to 0° C., methanesulfonyl chloride (142.4 g, 1.21 mol) was added neat over 5 minutes, followed by addition of neat N,N-diisopropylethylamine (167.9 g, 1.29 mol) over 25 minutes, while keeping the temperature less than 5° C. After stirring 20 minutes at <5° C., the reaction was warmed to room temperature and stirred for 14 hours. The crude reaction solution was washed twice with 4.5 liter portions of 10% citric acid and once with 4 liters of brine. The crude product solution was concentrated in vacuo to give a crude solid, then 2 liters of methanol was added followed by stirring for 1 hour. About half of the crude solid had dissolved in and then crystallized from the methanol. This material was collected by filtration and the resulting filtercake was rinsed with 300 ml of room temperature methanol. This first crop of material was dried at 50° C. and 10 mm for 2 hours to give 245.2 g, 41.2% of the title compound as an off-white solid. The crude solid that had not dissolved in and crystallized from methanol was redissolved in 1 liter of methylene chloride, then concentrated to a viscous brownish oil. The methanol mother liquor left over from the first crop was concentrated to a total volume of 800 ml and was then combined with the viscous brownish oil. This mixture was warmed in a 40° C. waterbath until a clear solution was obtained, then the resulting solution was cooled to 0° C. and stirred for 30 minutes, resulting in product precipitation. The precipitate was collected by filtration, and the resulting filtercake was washed with 200 ml of ice-chilled methanol, followed by air-drying for 16 hours. The second crop material (290.9 g, 48.8% ) was isolated as an off-white solid. The overall combined yield of first and second crops of acetic acid 3-[(2-chloroethyl)-(2,2-difluoropropyl)-carbamoyl]-1-(2-chlorophenyl)-5-(4-chlorophenyl)-1H-pyrazol4-yl-ester I-6f was 536.1 g (90%).

Method B: 1-(2-Chlorophenyl)-5-(4-chlorophenyl)-1H-pyrazole-3-carboxylic acid I-6b (90.8 g, 260 mmol) was dissolved in 1.7 liters of methylene chloride, giving an off-white suspension. 4-Methylmorpholine (58.5 g, 576 mmol) was added, giving a clear yellow solution, followed by addition of acetyl chloride (22.6 g, 284 mmol) over 10 minutes while maintaining a temperature between 20–30° C. The reaction was stirred for 7 hours at room temperature, then cooled to 0° C. 2-(2,2-Difluoropropylamino)-ethanol (39.8 g, 286 mmol) was added neat over 1 minute followed by addition of 2-Chloro4,6-dimethoxy-1,3,5-triazine (49.0 g, 271 mmol) portionwise as a solid over 1 minute. The reaction was allowed to slowly warm to room temperature over a period of 5 hours, followed by stirring for 12 hours at room temperature. The crude reaction solution was washed twice with 900 ml portions of 0.5 M citric acid and once with 900 ml of brine. Residual water was azeotropically removed through two cycles concentrating off methylene chloride and then adding more methylene chloride. The final crude methylene chloride solution volume was 1.2 liters. This solution was cooled to −2° C. followed by addition of neat methanesulfonyl chloride (36.0 g, 311 mmol) and then addition of neat N,N-diisopropylethylamine (42.1 g, 324 mmol) over a 10 minute period while maintaining a reaction temperature less than 10° C. The reaction solution was warmed to room temperature over 1 hour, followed by stirring for 20 hours, then washing the methylene chloride solution twice with 800 ml portions of 0.5 M citric acid and once with 800 ml brine. Product rich methylene chloride layer was clear dark orange in appearance (~1.3 liters total volume). Crude solution was concentrated in vacuo to ~300 ml, followed by addition of 1 liter of methanol. Resulting solution was concentrated in vacuo in a 30° C. waterbath by removing 900 ml of distillates. Another 800 ml portion of methanol was added followed by a final concentration in vacuo (30° C. waterbath) to remove 700 ml of distillates. The final total volume was ~500 ml. The product rich concentrated solution was held at room temperature for 1 hour (solution was initially hazy, dark orange in appearance, then solids precipitated after ~15 minutes). The mixture was cooled to −10° C. and stirred for 1 hour while maintaining temperature less than 0° C. The precipitated solids were collected by filtration, and the resulting filtercake was washed with 50 ml of ice-chilled methanol, followed by air-drying for 15 hours. The isolated solids were further dried at 60° C. and 1 mm for 2 hours (loss on drying was only 0.4 g) to give acetic acid 3-[(2-chloroethyl)-(2,2-difluoropropyl)-carbamoyl]-1-(2-chlorophenyl)-5-(4-chlorophenyl)-1H-pyrazol4-yl-ester I-6f (104.0 g, 75%) as a white solid.

$^1$H-NMR (CD$_2$Cl$_2$): δ 7.49–7.47 (m, 1H), 7.44–7.40 (m, 1H), 7.37–7.33 (m, 2H) 7.28 (d, 2H, rotamers, J=8.7 Hz), 7.14 (d, 2H, rotamers, J=8.7 Hz), 4.46 (t, 0.72H, J cannot be determined), 4.14 (t, 1.28H, J cannot be determined), 3.97 (t, 1.28H, J$_{HF}$=13.0 Hz), 3.87 (t, 0.72H, J=6.4 Hz), 2.22 (s, 1.08H), 2.20 (s, 1.92H), 1.62 (t, 3H, rotamers, J$_{HF}$=19.5 Hz). Two major rotamers present in a ~1.7:1 ratio. Mass Spec (ESI): M+1=530.2

Preparation of 1-(2-chlorophenyl)-5-(4-chlorophenyl)-4-hydroxy-1H-pyrazole-3-carboxylic acid (2-chloroethyl)-(2,2-difluoropropyl)-amide (I-6g)

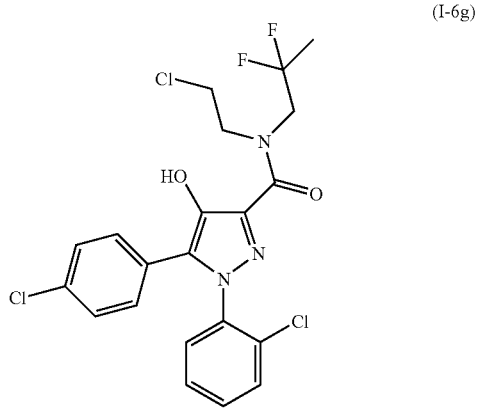

(I-6g)

Acetic acid 3-[(2-chloroethyl)-(2,2-difluoropropyl)-carbamoyl]-1-(2-chlorophenyl)-5-(4-chlorophenyl)-1-H-pyrazol-4-yl-ester I-6f (3.55 g, 6.69 mmol) was dissolved in 90 ml of methanol with warming in a 40° C. waterbath to give a clear colorless solution. The resulting solution was cooled to 0° C. (still a clear, colorless solution), followed by addition of K$_2$CO$_3$ (1.02 g, 7.31 mmol) in one portion as a solid (reaction mixture goes from colorless to yellow). Reaction stirred for 30 minutes at 0° C., followed by addition of concentrated hydrochloric acid (1.2 ml of 12.1 M, 14.5 mmol). Note: upon neutralization, reaction turns colorless and clear, then product begins to precipitate. The reaction was warmed to room temperature, then 45 ml of water was added, followed by stirring for 2.5 hours. The precipitated solids were collected by filtration and the resulting filtercake was washed with 50 ml of room temperature 2:1, methanol:water. Collected solids were dried at 50° C. and 10 mm for 1 hour to give 1-(2-chlorophenyl)-5-(4-chlorophenyl)-4-hydroxy-1H-pyrazole-3-carboxylic acid (2-chloroethyl)-(2,2-difluoropropyl)-amide I-6g (2.86 g, 87%) as a white solid.

$^1$H-NMR (CD$_2$Cl$_2$): δ 9.67 (s, 0.52 H), 9.57 (s, 0.48 H), 7.51–7.48 (m,1H), 7.46–7.41 (m, 1H), 7.39–7.31 (m, 2H), 7.24 (d, 2H, rotamers, J=8.7 Hz), 7.17 (d, 2H, rotamers, J=8.7 Hz), 4.75 (t, 0.52 H, J$_{HF}$=13 Hz), 4.47 (t, 0.48 H, J=6 Hz), 4.08 (t, 0.48 H, J$_{HF}$=13 Hz), 3.94 (t, 0.52 H, J=6 Hz), 3.84–3.79 (m, 2H), 1.66 (t, 1.44H, J$_{HF}$=19.3 Hz), 1.59 (t, 1.56H, J$_{HF}$=19.1 Hz). Two major rotamers present in a ~1.07:1 ratio. Mass Spec (ESI): M+1=488.2

Example 1

Preparation of 3-(4-Chlorophenyl)-2-(2-chlorophenyl)-7-(2,2,2-trifluoroethyl)-6,7-dihydro-2H,5H-4-oxa-1,2,7-triaza-azulen-8-one (1A-1)

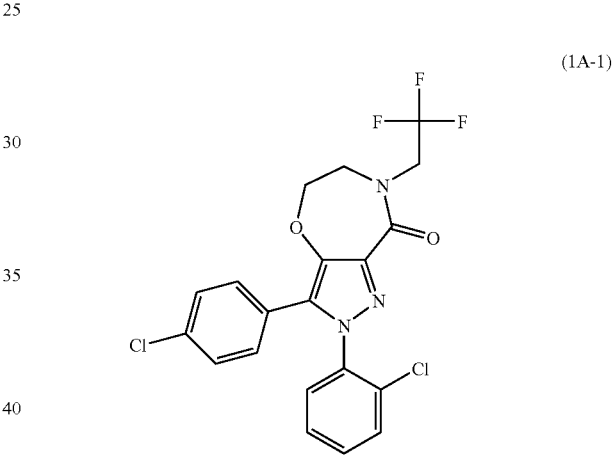

(1A-1)

A solution of 5-(4-chlorophenyl)-1-(2-chlorophenyl)-4-[2-(2,2,2-trifluoroethylamino)-ethoxy]-1H-pyrazole-3-carboxylic acid, hydrochloride I-1h (45 mg, 0.1 mmol), triethylamine (0.05 ml) and 1-propanephosphoric acid cyclic anhydride (0.1 ml, 0.14 mmol) in 1,2-dichloroethane (0.6 ml) were stirred for 8 hours. The reaction was diluted into ethyl ether, washed 1 N aqueous hydrochloric acid, saturated aqueous sodium bicarbonate, brine, dried (Na$_2$SO$_4$) and concentrated in vacuo to afford the title compound (1A-1) as a white solid, 35 mg. $^1$H NMR in CDCl$_3$ (ppm): δ7.52 (d, 1H), 7.38–7.34 (m, 2H), 7.23 (d, 2H), 7.15 (d, 2H), 4.47 (brs, 2H), 4.29 (br s, 2H), 3.91 (br s, 2H); ms (LCMS) m/z=456.3 (M+1).

The compounds listed below were prepared using procedures analogous to those described above for the synthesis of Compound 1A-1 and outlined in Scheme I above using the appropriate starting materials which are available commercially or prepared using preparations well-known to those skilled in the art.

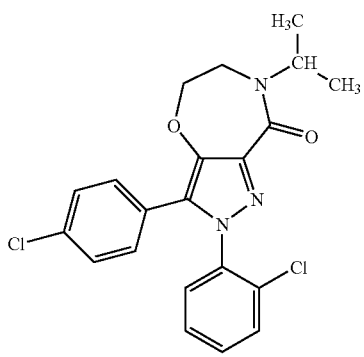

3-(4-Chlorophenyl)-2-(2-chlorophenyl)-7-isopropyl-6,7-dihydro-2H,5H-4-oxa-1,2,7-triaza-azulen-8-one (1A-2): m/z=416.4 (M+1)

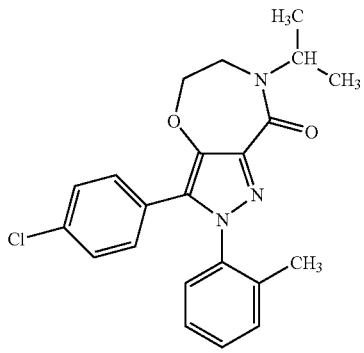

3-(4-Chlorophenyl)-7-isopropyl-2-o-tolyl-6,7-dihydro-2H,5H-4-oxa-1,2,7-triaza-azulen-8-one (1A-3): m/z=396.4 (M+1)

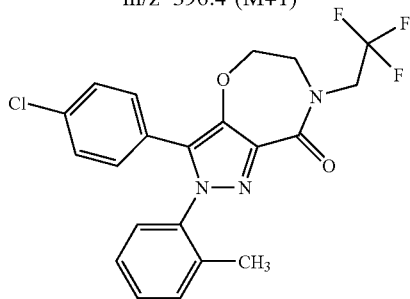

3-(4-Chloro-phenyl)-2-o-tolyl-7-(2,2,2-trifluoro-ethyl)-6,7-dihydro-2H,5H-4-oxa-1,2,7-triaza-azulen-8-one (1A-4): m/z=436.2 (M+1)

Example 2

Preparation of 3-(4-Chloro-phenyl)-2-(2-chloro-phenyl)-7-(2,2-difluoro-propyl)-6,7-dihydro-2H,5H-4-oxa-1,2,7-triaza-azulen-8-one (2A-1)

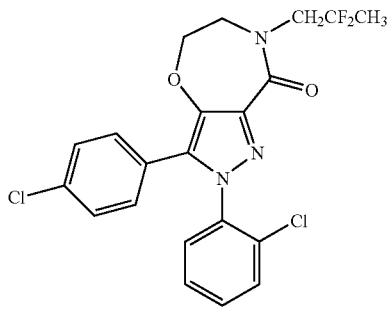

2A-1

To a stirred solution of 1-(2-chloro-phenyl)-5-(4-chloro-phenyl)4-hydroxy-1H-pyrazole-3-carboxylic acid (2,2-difluoro-propyl)-(2-hydroxy-ethyl)-amide I-3d (10 g, 21 mmol), triphenyl phosphine (8.4 g, 31.5 mmol) in toluene (210 ml) was added 1,1'-(azodicarbonyl)dipiperidine (8.0 g, 31.5 mmol). After 18 hours, 20% ethyl acetate:hexanes (210 ml) was added, the mixture was stirred at ambient temperature for 1 hour and filtered. The filtrate was concentrated in vacuo and the resulting oil was chromatographed on silica gel (20–70% ethyl acetate:hexanes) to afford the title compound (2A-1) as a solid, 7.8 g. 1H NMR in CDCl$_3$ (ppm) δ 7.53–7.50 (m, 1H), 7.38–7.33 (m, 3H), 7.24–7.21 (m, 2H), 7.16–7.13 (m, 2H), 4.45 (br s, 2H), 4.02 (t, 2H), 3.90 (br s, 2H), 1.69 (t, 3H); ms (LCMS) m/z=452.2 (M+1). Combustion analysis calculated for: C: 55.77%; H: 3.79%; N: 9.29%. Found: C: 55.69%; H: 3.52%; N: 9.13%.

The compounds listed below were prepared using procedures analogous to those described above for the synthesis of Compound 2A-1 and outlined in Scheme III above using the appropriate starting materials which are available commercially or prepared using preparations well-known to those skilled in the art.

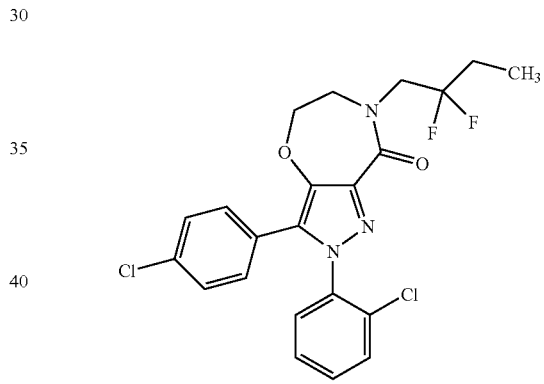

3-(4-Chloro-phenyl)-2-(2-chloro-phenyl)-7-(2,2-difluoro-butyl)-6,7-dihydro-2H,5H-4-oxa-1,2,7-triaza-azulen-8-one (2A-2): m/z=466.1 (M+1)

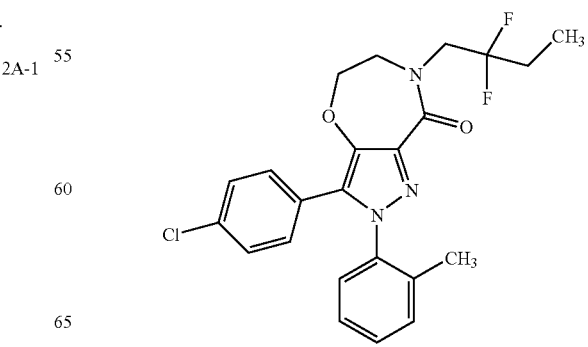

3-(4-Chloro-phenyl)-7-(2,2-difluoro-butyl)-2-o-tolyl-6,7-dihydro-2H,5H-4-oxa-1,2,7-triaza-azulen-8-one (2A-3): m/z=446.2 (M+1)

Example 3

Preparation of 3-(4-Chlorophenyl)-2-(2-chlorophenyl)-7-(2,2,2-trifluoroethyl)-4,5,6,7-tetrahydro-2H-pyrazolo[4,3-e][1,4]diazepin-8-one (3A-1)

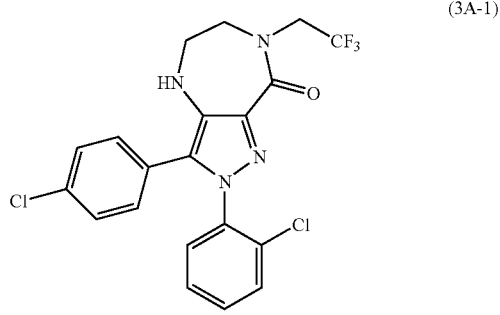

A solution of 3-(4-chlorophenyl)-2-(2-chlorophenyl)-4-trifluoroacetyl-4,5,6,7-tetrahydro-2H-pyrazolo[4,3-e][1,4]diazepin-8-one (I-4f, 47 mg, 0.10 mmol) and NaH (5 mg, 60% dispersion, 0.12 mmol) in DMF (1.5 ml) was stirred for 1 hour at room temperature under a $N_2$ atmosphere, then trifluoromethanesulfonic acid 2,2,2-trifluoroethyl ester (22 microliters, 0.15 mmol) was added dropwise. The reaction mixture was stirred for 2 hours, quenched with saturated aqueous NaCl, and extracted twice with EtOAc. The combined organic extracts were washed with saturated aqueous $NaHCO_3$ and saturated aqueous NaCl, dried, and concentrated under vacuum. The crude residue was purified on a chromatotron using 1 mm plates and a solvent gradient of 1:1 hexanes/EtOAc to 100% EtOAc to 9:1 EtOAc/MeOH to give 3A-1 as an amorphous glass (6 mg): +ES MS (M+1) 455.4; $^1$H NMR ($CD_2Cl_2$) δ 7.50–7.37 (m, 4H), 7.32 (d, 2H, J=8.3 Hz), 7.18 (d, 2H, J=8.3 Hz), 4.29 (q, 2H, J=8.8 Hz), 3.84–3.79 (m, 2H), 3.60–3.55 (m, 2H).

Example 4

Preparation of 1-(4-Chlorophenyl)-2-(2-chlorophenyl)-5,6,7,7a,8,9-hexahydro-2H-2,3,4a,9-tetraazacyclopenta[f]azulen-4-one (4A-1)

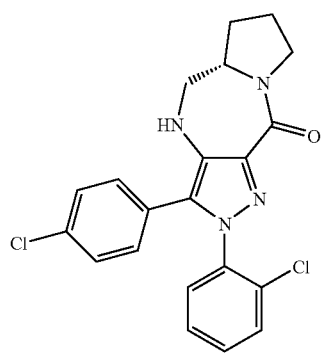

Diisopropylethylamine (250 microliters, 2 mmol) was added to a mixture of 1-(2-chlorophenyl)-5-(4-chlorophenyl)-4-[(pyrrolidin-2-ylmethyl)-amino]-1H-pyrazole-3-carboxylic acid (I-5b, 160 mg, 0.37 mmol) and HATU (380 mg, 1 mmol) in DMF (50 ml) at room temperature. The reaction mixture was stirred for 5 hours, quenched with saturated aqueous NaCl, and extracted twice with EtOAc. The combined organic extracts were washed with 0.5 M citric acid, 1 M $K_2CO_3$, and saturated aqueous NaCl, dried, and concentrated in vacuo. The residue was slurried in $CH_2Cl_2$ and the solvent decanted, a process repeated once more with EtOAc. The combined organic solutions were concentrated under vacuum and the residue was purified on a chromatogram using 4 mm plates and a solvent gradient of 10:1 EtOAc/MeOH to 5:1 EtOAc/MeOH to give 4A-1 as a white solid (46 mg): +ES MS (M+1) 413.4; $^1$H NMR ($CD_3OD$) δ 7.58 (bs, 1H), 7.52–7.44 (m, 3H), 7.34 (d, 2H, J=7.6 Hz), 7.22 (d, 2H, J=7.6 Hz), 3.93–3.82 (m, 2H), 3.64–3.50 (m, 2H), 3.10–2.99 (m,1 H), 2.38–2.29 (m,1 H), 2.04–1.96 (m, 1H), 1.95–1.74 (m, 2H).

The following demonstrates an alternative method for preparing compounds of the present invention where A is nitrogen, B is carbon and X is O.

Example 5

Preparation of 3-(4-Chlorophenyl)-2-(2-chlorophenyl)-7-(2.2-difluoropropyl)-6,7-dihydro-2H,5H-4-oxa-1,2,7-triaza-azulen-8-one (1-5A)

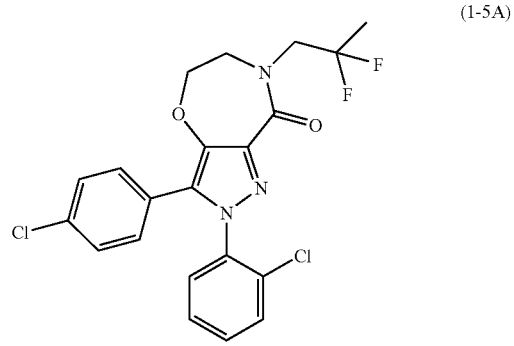

Acetic acid 3-[(2-chloroethyl)-(2,2-difluoropropyl)-carbamoyl]-1-(2-chlorophenyl)-5-(4-chlorophenyl)-1H-pyrazol-4-yl-ester I-6g (513.0 g, 0.97 mol) was suspended in 9.7 liter of ethanol (gives a off-white suspension). Cesium carbonate (348.0 g, 1.07 mol) was added portionwise as a solid over 2 minutes while maintaining internal temperature between 21–27° C. Note: Upon $Cs_2CO_3$ addition, reaction mixture turned pale yellow (still a suspension). Reaction stirred at room temperature for 19 hours, then the crude reaction mixture was filtered through Celite® to remove insoluble solids, giving a clear dark yellow filtrate. The Celite® filtercake was washed with 2 liters of ethanol. The crude product solution was concentrated in vacuo and gave a yellow solid. This solid was reconstituted in 7 liters of methylene chloride and the resulting mixture was washed once with 5 liters of half saturated aqueous $NH_4Cl$ and once with 4 liters of brine. The product rich methylene chloride layer was concentrated in vacuo to a total volume of 2.5 liters. Note: The methylene chloride layer was clear and dark resddish in color. The product rich methylene chloride solution was treated with 105 g of Darco, followed by stirring at reflux for 30 minutes. After cooling, the Darco was filtered off by passing the solution through Celite®. Note: Crude product solution is clear dark orange in appearance. The crude product filtrate was concentrated in vacuo to a total volume of 1.1 liters. This product rich methylene chloride solution was added over 20 minutes to 5 liters of cyclohexane while maintaining a reaction pot temperature of 50–60° C. Note: Halfway through methylene chloride solution addition, precipitate came out of solution. After complete addition, the methylene chloride solvent was atmospherically removed (3.55 liters of distillates collected while simultaneously adding 2 liters of cyclohexane to refluxing solution) from the reaction mixture by heating to 79° C. (internal pot temperature) over a 2.5 hour period. Once internal temperature reached the boiling point of cyclohexane, all of the methylene chloride had been displaced. Note: The reaction mixture took on a very dark pink/purple coloration with white solids suspended. Reaction mixture held at 79° C. for 10 minutes, then cooled to 50° C. and held for 13 hours, followed by cooling to 30° C. and holding for 4 hours. The precipitated product was collected by filtration, and the resulting filtercake was washed with 3 liters of room temperature cyclohexane, followed by air-drying for 3.5 hours. The isolated solids were further dried at 50° C. and 2 mm for 15 hours (loss on drying was only 0.2 g) to give 3-(4-chlorophenyl)-2-(2-chlorophenyl)-7-(2,2-difluoropropyl)-6,7-dihydro-2H,5H-4-oxa-1,2,7-triaza-azulen-8-one 1-5A (321.3 g, 73%) as an off-white solid.

Recrystallization of 3-(4-Chlorophenyl)-2-(2-chlorophenyl)-7-(2,2-difluoropropyl)-6,7-dihydro-2H, 5H-4-oxa-1,2,7-triaza-azulen-8-one (1-5A)

3-(4-Chlorophenyl)-2-(2-chlorophenyl)-7-(2,2-difluoropropyl)-6,7-dihydro-2H,5H-4-oxa-1,2,7-triaza-azulen-8-one 1-5A (5.00 g, 11.1 mmol) was dissolved in 20 ml of methylene chloride to give a clear orange solution. Darco KBB (0.5 g) was added followed by heating to reflux and stirring for 1 hour. After cooling, the Darco KBB was filtered off by passing the solution through Celite®, giving a clear light yellow filtrate. The Celite® filtercake was washed with 10 ml of methylene chloride. The eluent was concentrated in vacuo to give a total solution volume of ~20 ml. The concentrated methylene chloride solution was then diluted with 150 ml of 2-propanol to give a clear pale yellow solution. Methylene chloride was removed from the resulting solution by atmospherically distilling off 71 ml of distillates as solution was heated from room temperature to 82° C. (boiling point of 2-propanol). The solution was then cooled over 3 hours from 82° C. to room temperature. Note: Solution became hazy around 34° C., followed by precipitate formation. The mixture was stirred at room temperature for 62 hours, then cooled to 0° C. and stirred for 2.5 hours before collecting the precipitate by filtration. The resulting filtercake was washed with 80 ml of ice-chilled 2-propanol, then air-dried for 1 hour. The recrystallized 3-(4-Chlorophenyl)-2-(2-chlorophenyl)-7-(2,2-difluoropropyl)-6,7-dihydro-2H,5H-4-oxa-1,2,7-triaza-azulen-8-one 1-5A (4.03 g, 81%) was isolated as a pure white crystalline solid.

$^1$H-NMR (CD$_2$Cl$_2$): δ 7.49–7.46 (m, 1H), 7.45–7.37 (m, 3H), 7.24 (d, 2H, rotamers, J=9.1Hz), 7.16 (d, 2H, rotamers, J=8.7 Hz), 4.44 (dd, 2H, J=5.2 Hz, 1.9 Hz), 3.98 (t, 2H, $J_{HF}$=13 Hz), 3.87 (t, 2H, J=3.7 Hz), 1.67 (t, 3H, $J_{HF}$=19.1 Hz) Mass Spec (ESI): M+1=452.2

In addition to the compounds described above in Examples 1–5, the following compounds may be prepared using the methods and procedures generally described above in Scheme IV:

2-(2-Chlorophenyl)-3-(4-ethylphenyl)-7-(2,2,2-trifluoroethyl)-6,7-dihydro-2H,5H-4-oxa-1,2,7-triaza-azulen-8-one;

2-(2-Chlorophenyl)-7-(2,2-difluoropropyl)-3-(4-ethylphenyl)-6,7-dihydro-2H,5H-4-oxa-1,2,7-triaza-azulen-8-one; and 2-(2-Chlorophenyl)-3-(4-ethylphenyl)-7-isopropyl-6,7-dihydro-2H,5H-4-oxa-1,2,7-triaza-azulen8-one Pharmacological Testing The utility of the compounds of the present invention in the practice of the instant invention can be evidenced by activity in at least one of the protocols described hereinbelow. The following acronyms are used in the protocols described below.

BSA—bovine serum albumin
DMSO—dimethylsulfoxide
EDTA—ethylenediamine tetracetic acid
PBS—phosphate-buffered saline
EGTA—ethylene glycol-bis(β-aminoethyl ether) N,N,N', N'-tetraacetic acid
GDP—guanosine diphosphate
sc—subcutaneous
po—orally
ip—intraperitoneal
icv—intra cerebro ventricular
iv—intravenous
[$^3$H]SR141716A—radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.
[$^3$H]CP-55940—radiolabled 5-(1,1-dimethylheptyl)-2-[5-hydroxy-2-(3-hydroxypropyl)-cyclohexyl]-phenol available from NEN Life Science Products, Boston, Mass.
AM251—N-(piperidin-1-yl)-1-(2,4-dichlorophenyl)-5-(4-iodophenyl)-4-methyl-1H-pyrazole-3-carboxamide available from Tocris™, Ellisville, Mo.

Compounds having an activity <20 nM are generally tested in the CB-1 GTPγ [$^{35}$S] Binding Assay and the CB-2 binding assay described below in the Biological Binding Assays section. Selected compounds are then tested in vivo using one or more of the functional assays described in the Biological Functional Assays section below. CB-1binding activities of 0.5–250 nM were observed for Examples 1–5.

In Vitro Biological Assays

Bioassay systems for determining the CB-1 and CB-2 binding properties and pharmacological activity of cannabinoid receptor ligands are described by Roger G. Pertwee in "Pharmacology of Cannabinoid Receptor Ligands" Current Medicinal Chemistry, 6, 635–664 (1999) and in WO 92/02640 (U.S. application Ser. No. 07/564,075 filed Aug. 8, 1990, incorporated herein by reference).

The following assays were designed to detect compounds that inhibit the binding of [$^3$H] SR141716A (selective radiolabeled CB-1 ligand) and [$^3$H] 5-(1,1-dimethylheptyl)-2-[5- hydroxy-2-(3-hydroxypropyl)-cyclohexyl]-phenol; radiolabeled CB-1/CB-2 ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM $MgCl_2$, and 1 mM EDTA) per brain used. A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [$^3$H] SR141716A was diluted in a ligand buffer (0.5% BSA plus TME) and 25 μl were added to the plate. A BCA protein assay was used to determine the appropriate tissue concentration and then 200 μl of rat brain tissue at the appropriate concentration was added to the plate. The plates were covered and placed in an incubator at 20° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×g for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM $MgCl_2$ and 1 mM EDTA). A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [$^3$H] SR141716A was diluted in a ligand buffer (0.5% BSA plus TME) and 25 μl were added to the plate. The plates were covered and placed in an incubator at 30° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

CB-2 Receptor Binding Protocol

Chinese hamster ovary-K1 (CHO-K1) cells transfected with CB-2 cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM $MgCl_2$ and 1 mM EDTA) per brain used. A protein assay was performed and 200 μl of tissue totaling 10 μg was added to the assay.

The test compounds were diluted in drug buffer (0.5% BSA, 10% DMSO, and 80.5% TME) and then 25 μl were added to the deep well polypropylene plate. [$^3$H] 5-(1,1-Dimethyl-heptyl)-2-[5-hydroxy-2-(3-hydroxy-propyl)-cyclohexyl]-phenol was diluted a ligand buffer (0.5% BSA and 99.5% TME) and then 25 μl were added to each well at a concentration of 1 nM. A BCA protein assay was used to determine the appropriate tissue concentration and 200 μl of the tissue at the appropriate concentration was added to the plate. The plates were covered and placed in an incubator at 30° C. for 60 minutes. At the end of the incubation period 250 μl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 GTPγ [$^{35}$S] Binding Assay

Membranes were prepared from CHO-K1 cells stably transfected with the human CB-1 receptor cDNA. Membranes were prepared from cells as described by Bass et al, in "Identification and characterization of novel somatostatin antagonists," *Molecular Pharmacology*, 50, 709–715 (1996). GTPγ [$^{35}$S] binding assays were performed in a 96 well FlashPlate™ format in duplicate using 100 μM GTPγ [$^{35}$S] and 10 μg membrane per well in assay buffer composed of 50 mM Tris HCl, pH 7.4, 3 mM $MgCl_2$, pH 7.4, 10 mM $MgCl_2$, 20 mM EGTA, 100 mM NaCl, 30 μM GDP, 0.1% bovine serum albumin and the following protease inhibitors: 100 μg/ml bacitracin, 100 μg/ml benzamidine, 5 μg/ml aprotinin, 5 μg/ml leupeptin. The assay mix was then incubated with increasing concentrations of antagonist ($10^{-10}$ M to $10^{-5}$ M) for 10 minutes and challenged with the cannabinoid agonist 5-(1,1-dimethyl-heptyl)-2-[5-hydroxy-2-(3-hydroxy-propyl)-cyclohexyl]-phenol (10 μM). Assays were performed at 30° C. for one hour. The FlashPlates™ were then centrifuged at 2000×g for 10 minutes. Stimulation of GTPγ[$^{35}$S] binding was then quantified using a Wallac Microbeta.$EC_{50}$ calculations done using Prism™ by Graphpad.

Inverse agonism was measured in the absense of agonist.

CB-1 FLIPR-based Functional Assay Protocol

CHO-K1cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4 μM Fluo-4 AM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 min the plates were added to the FLIPR individually and fluorescence levels was continuously monitored over an 80 second period. Compound additions were made simultaneously to all 384 wells after 20 seconds of baseline. Assays were performed in triplicate and 6 point concentration-response curves generated. Antagonist compounds were subsequently challenged with 3 μM WIN 55,212-2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000–14,000 cells per well at a concentration of 100 μl per well. The plates were incubated for 24 hours in a 37° C. incubator. The media was removed and media lacking serum (100 μl) was added. The plates were then incubated for 18 hours at 37° C.

Serum free medium containing 1 mM IBMX was added to each well followed by 10 μl of test compound (1:10 stock solution (25 mM compound in DMSO) into 50% DMSO/PBS) diluted 10× in PBS with 0.1% BSA. After incubating for 20 minutes at 37° C., 2 μM of Forskolin was added and then incubated for an additional 20 minutes at 37° C. The media was removed, 100 μl of 0.01 N HCl was added and then incubated for 20 minutes at room temperature. Cell lysate (75 μl) along with 25 μl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agoinists such as $\Delta^9$-tetrahydrocannabinol ($\Delta^9$-THC) and 5-(1,1-dimethyl-heptyl)-2-[5-hydroxy-2-(3-hydroxy-propyl)-cyclohexyl]-phenolhave been shown to affect four characteristic behaviors in mice, collectively known as the Tetrad. For a description of these behaviors see: Smith, P. B., et al. in "The pharmacological activity of anandamide, a putative endogenous cannabinoid, in mice." J. Pharmacol. Exp. Ther., 270(1), 219–227 (1994) and Wiley, J., et al. in "Discriminative stimulus effects of anandamide in rats," Eur. J. Pharmacol., 276(1–2), 49–54 (1995). Reversal of these activities in the Locomotor Activity, Catalepsy, Hypothermia, and Hot Plate assays described below provides a screen for in vivo activity of CB-1antagonists.

All data is presented as % reversal from agonist alone using the following formula: (5-(1,1-dimethyl-heptyl)-2-[5-hydroxy-2-(3-hydroxy-propyl)-cyclohexyl]-phenol/agonist–vehicle/agonist)/(vehicle/vehicle–vehicle/agonist). Negative numbers indicate a potentiation of the agonist activity or non-antagonist activity. Positive numbers indicate a reversal of activity for that particular test.

Locomotor Activity

Male ICR mice (n=6; 17–19 g, Charles River Laboratories, Inc., Wilmington, Mass.) were pre-treated with test compound (sc, po, ip, or icv). Fifteen minutes later, the mice were challenged with 5-(1,1-dimethyl-heptyl)-2-[5-hydroxy-2-(3-hydroxy-propyl)-cyclohexyl]-phenol (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6; 17–19 g upon arrival) were pre-treated with test compound (sc, po, ip or icv). Fifteen minutes later, the mice were challenged with 5-(1,1-dimethyl-heptyl)-2-[5-hydroxy-2-(3-hydroxy-propyl)-cyclohexyl]-phenol (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5; 17–19 g upon arrival) were pre-treated with test compounds (sc, po, ip or icv). Fifteen minutes later, mice were challenged with the cannabinoid agonist 5-(1,1-dimethyl-heptyl)-2-[5-hydroxy-2-(3-hydroxy-propyl)-cyclohexyl]-phenol (sc). Sixty-five minutes post agonist injection, rectal body temperatures were taken. This was done by inserting a small thermostat probe approximately 2–2.5 cm into the rectum. Temperatures were recorded to the nearest tenth of a degree Hot Plate Male ICR mice (n=7; 17–19 g upon arrival) are pre-treated with test compounds (sc, po, ip or iv). Fifteen minutes later, mice were challenged with a cannabinoid agonist 5-(1,1-dimethyl-heptyl)-2-[5-hydroxy-2-(3-hydroxy-propyl)-cyclohexyl]-phenol (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats Were obtained from Charles River Laboratories, Inc. (Wilmington, Mass.). The rats were individually housed and fed powdered chow. They were maintained on a 12-hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li, T.-K., et al., "Indiana selection studies on alcohol related behaviors" in *Development of Animal Models as Pharmacogenetic Tools* (eds McClearn C. E., Deitrich R. A. and Erwin V. G.), Research Monograph 6,171–192 (1981) NIAAA, ADAMHA, Rockville, Md.; Lumeng, L, et al., "New strains of rats with alcohol preference and nonpreference" *Alcohol And Aldehyde Metabolizing Systems*, 3, Academic Press, New York, 537–544 (1977); and Lumeng, L, et al., "Different sensitivities to ethanol in alcohol-preferring and -nonpreferring rats," *Pharmacol, Biochem Behav.*, 16, 125–130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n=8); Group 2—positive control (e.g., 5.6 mg/kg AM251; n=8); Group 3—low dose test compound (n=8); and Group 4—high dose of test compound (n=8). Test compounds were generally mixed into a vehicle of 30% (w/v) β-cyclodextrin in distilled water at a volume of 1–2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between drug and vehicle-treated animals to determine effects of the compounds on alcohol drinking behavior.

Additional drinking studies were done utilizing female C57Bl/6 mice (Charles River). Several studies have shown that this strain of mice will readily consume alcohol with little to no manipulation required (Middaugh et al., "Ethanol Consumption by C57BU6 Mice: Influence of Gender and Procedural Variables" *Alcohol*, 17 (3),175–183, 1999; Le et al., "Alcohol Consumption by C57BU6, BALA/c, and DBA/2 Mice in a Limited Access Paradigm" *Pharmacology Biochemistry and Behavior*, 47, 375–378, 1994).

For our purposes, upon arrival (17–19 g) mice were individually housed and given unlimited access to powdered rat chow, water and a 10% (w/v) alcohol solution. After 2–3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7–10) so that all groups had equivocal alcohol intake. On day 2 and 3, mice were injected with vehicle or drug and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (300–380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e., sc, ip, iv). Drugs are prepared in methylcellulose, water or other specified vehicle (examples include PEG400, 30% beta-cyclo dextran and propylene glycol). Oxygen consumption and ambulatory activity are measured every 10 minutes for an additional 1–6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min $O_2$ consumption values, excluding periods of high ambulatory activity (ambulatory activity count>100) and excluding the first 5 values of the pre-dose period and the first value from the post-dose period. Change in oxygen consumption is reported as percent and is calculated by dividing the post-dosing resting oxygen consumption by the pre-dose oxygen consumption *100. Experiments will typically be done with n=4–6 rats and results reported are mean +/− SEM.

Interpretation:

An increase in oxygen consumption of >10% is considered a positive result. Historically, vehicle-treated rats have no change in oxygen consumption from pre-dose basal.

What is claimed is:
1. A compound having the Formula (I)

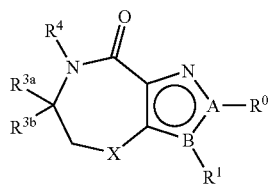

wherein
- A is nitrogen and B is carbon, or A is carbon and B is nitrogen;
- $R^0$ is an aryl optionally substituted with one or more substituents, or a heteroaryl optionally substituted with one or more substituents;
- $R^1$ is aryl optionally substituted with one or more substituents, heteroaryl optionally substituted with one or more substituents, —CH=CH—$R^{1a}$, or —CH$_2$CH$_2$—$R^{1a}$, where $R^{1a}$ is hydrogen or a chemical moiety selected from ($C_1$–$C_8$)alkyl, 3- to 8-membered partially or fully saturated carbocyclic ring(s), 3- to 6-membered partially or fully saturated heterocycle, aryl, or heteroaryl, where the chemical moiety is optionally substituted with one or more substituents;
- X is O, S, SO, SO$_2$, —N($R^{2a}$)— or —C($R^{2b}$)($R^{2c}$)—, where $R^{2a}$, $R^{2b}$ and $R^{2c}$ are each independently hydrogen, ($C_1$–$C_4$)alkyl, halo-substituted ($C_1$–$C_4$)alkyl, or ($C_1$–$C_5$)acyl;
- $R^{3a}$ and $R^{3b}$ are each independently hydrogen, ($C_1$–$C_6$)alkyl, or halo-substituted ($C_1$–$C_6$)alkyl,
- or either $R^{3a}$ or $R^{3b}$ taken together with $R^4$ forms a fully or partially saturated 5- to 6-membered heterocyclic ring, where the heterocyclic ring optionally contains an additional heteroatom selected from oxygen, nitrogen or sulfur and is optionally substituted with one or more substituents; and
- $R^4$ is a chemical moiety selected from the group consisting of ($C_1$–$C_8$)alkyl, aryl, heteroaryl, aryl($C_1$–$C_4$)alkyl, a 3- to 8-membered partially or fully saturated carbocyclic ring(s), heteroaryl($C_1$–$C_3$)alkyl, 5–6 membered lactone, 5- to 6-membered lactam, and a 3- to 8-membered partially or fully saturated heterocycle, where said chemical moiety is optionally substituted with one or more substituents,
- or $R^4$ taken together with either $R^{3a}$ or $R^{3b}$ forms a fully or partially saturated 5- to 6-membered heterocyclic ring, where the heterocyclic ring optionally contains an additional heteroatom selected from oxygen, nitrogen or sulfur and is optionally substituted with one or more substituents;

a pharmaceutically acceptable salt thereof or a solvate or hydrate of said compound, or said salt.

2. The compound of claim 1 wherein A is nitrogen and B is carbon;
a pharmaceutically acceptable salt thereof, or a solvate or hydrate of said compound, or said salt.

3. The compound of claim 2 wherein X is oxygen;
a pharmaceutically acceptable salt thereof, or a solvate or hydrate of said compound, or said salt.

4. The compound of claim 3 wherein $R^{3a}$ and $R^{3b}$ are each independently hydrogen, ($C_1$–$C_4$)alkyl, or fluoro-substituted ($C_1$–$C_4$)alkyl;
a pharmaceutically acceptable salt thereof, or a solvate or hydrate of said compound, or said salt.

5. The compound of claim 3 wherein $R^4$ is a chemical moiety selected from the group consisting of ($C_1$–$C_8$)alkyl, aryl($C_1$–$C_4$)alkyl, and 3- to 8-membered partially or fully saturated carbocyclic ring(s) and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

6. The compound of claim 4 wherein $R^4$ is ($C_1$–$C_8$)alkyl, fluoro-substituted ($C_1$–$C_8$)alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

7. The compound of claim 5 wherein $R^4$ is ($C_1$–$C_8$)alkyl, fluoro-substituted ($C_1$–$C_8$)alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

8. The compound of claim 6 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

9. The compound of claim 7 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

10. The compound of claim 3, 4, 5, 6, 7, 8 or 9 wherein $R^0$ and $R^1$ are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano;
a pharmaceutically acceptable salt thereof, or a solvate or hydrate of said compound, or said salt.

11. The compound of claim 10 wherein $R^0$ and $R^1$ are each independently a phenyl substituted with 1 to 2 substituents independently selected from the group consisting of chloro, fluoro, ($C_1$–$C_4$)alkoxy, ($C_1$–$C_4$)alkyl, fluoro-substituted ($C_1$–$C_4$)alkyl), and cyano;
a pharmaceutically acceptable salt thereof, or a solvate or hydrate of said compound, or said salt.

12. The compound of claim 11 wherein $R^0$ is 2-chlorophenyl, 2-fluorophenyl, 2,4-dichlorophenyl, 2-fluoro-4-chlorophenyl 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl.
a pharmaceutically acceptable salt thereof, or a solvate or hydrate of said compound, or said salt.

13. The compound of claim 12 selected from the group consisting of
3-(4-chlorophenyl)-2-(2-chlorophenyl)-7-(2,2,2-trifluoroethyl)-6,7-dihydro-2H,5H-4-oxa-1,2,7-triaza-azulen-8-one;

3-(4-chlorophenyl)-2-(2-chlorophenyl)-7-(2,2-difluoropropyl)-6,7-dihydro-2H,5H-4-oxa-1,2,7-triaza-azulen-8-one;

3-(4-chloro-phenyl)-2-(2-chloro-phenyl)-7-(2,2-difluorobutyl)-6,7-dihydro-2H,5H-4-oxa-1,2,7-triaza-azulen-8-one; and 3-(4-chloro-phenyl)-2-(2-chloro-phenyl)-7-isopropyl-6,7-dihydro-2H,5H-4-oxa-1,2,7-triaza-azulen-8-one;

or a solvate or hydrate of said compound.

14. The compound of claim 13 which is 3-(4-chlorophenyl)-2-(2-chlorophenyl)-7-(2,2-difluoropropyl)-6,7-dihydro-2H,5H-4-oxa-1,2,7-triaza-azulen-8-one.

15. The compound of claim 2 where X is —C($R^{2b}$)($R^{2c}$)—;

a pharmaceutically acceptable salt thereof, or a solvate or hydrate of said compound, or said salt.

16. The compound of claim 15 wherein at least one of $R^{2b}$ or $R^{2c}$ is ($C_{1-C_4}$)alkyl, or fluoro-substituted ($C_1$–$C_4$)alkyl;

a pharmaceutically acceptable salt thereof, or a solvate or hydrate of said compound, or said salt.

17. The compound of claim 15 wherein both $R^{2b}$ and $R^{2c}$ are hydrogen;

a pharmaceutically acceptable salt thereof, or a solvate or hydrate of said compound, or said salt.

18. The compound of claim 15, 16 or 17 wherein $R^4$ is a chemical moiety selected from the group consisting of ($C_1$–$C_8$)alkyl, aryl($C_1$–$C_4$)alkyl, 3- to 8-membered partially or fully saturated carbocyclic ring(s) and 3- to 8-membered partially or fully saturated heterocycle, where said chemical moiety is optionally substituted with one or more substituents;

or $R^4$ taken together with either $R^{3a}$ or $R^{3b}$ forms a fully or partially saturated 5- to 6-membered heterocyclic ring, where said heterocyclic ring is optionally substituted with one or more substituents;

a pharmaceutically acceptable salt thereof, or a solvate or hydrate of said compound, or said salt.

19. The compound of claim 15, 16 or 17 wherein $R^{3a}$ and $R^{3b}$ are each independently hydrogen, ($C_1$–$C_4$)alkyl, or fluoro-substituted ($C_1$–$C_4$)alkyl.

20. The compound of claim 18 wherein $R^4$ is ($C_1$–$C_8$)alkyl, fluoro-substituted ($C_1$–$C_8$)alkyl, cyclopentyl, cyclohexyl, piperidin-1-yl, pyrrolidin-1-yl, or morpholin-1-yl;

a pharmaceutically acceptable salt thereof, or a solvate or hydrate of said compound, or said salt.

21. The compound of claim 19 wherein $R^4$ is ($C_1$–$C_8$)alkyl, fluoro-substituted ($C_1$–$C_8$)alkyl, cyclopentyl, cyclohexyl, piperidin-1-yl, pyrrolidin-1-yl, or morpholin-1-yl;

a pharmaceutically acceptable salt thereof, or a solvate or hydrate of said compound, or said salt.

22. The compound of claim 20 wherein $R^4$ is ethyl, isopropyl, 2,2,2-trifluoroethyl, 2,2-difluoropropyl or 2,2-difluorobutyl;

a pharmaceutically acceptable salt thereof, or a solvate or hydrate of said compound, or said salt.

23. The compound of claim 21 wherein $R^4$ is ethyl, isopropyl, 2,2,2-trifluoroethyl, 2,2-difluoropropyl or 2,2-difluorobutyl;

a pharmaceutically acceptable salt thereof, or a solvate or hydrate of said compound, or said salt.

24. The compound of claim 15, 16 or 17 wherein $R^0$ and $R^1$ are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano;

a pharmaceutically acceptable salt thereof, or a solvate or hydrate of said compound, or said salt.

25. The compound of claim 24 wherein $R^0$ and $R^1$ are each independently a phenyl substituted with 1 to 2 substituents independently selected from the group consisting of chloro, fluoro, ($C_1$–$C_4$)alkoxy, ($C_1$–$C_4$)alkyl, fluoro-substituted ($C_1$–$C_4$)alkyl), and cyano;

a pharmaceutically acceptable salt thereof, or a solvate or hydrate of said compound, or said salt.

26. The compound of claim 25 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

27. The compound of claim 18 wherein $R^0$ and $R^1$ are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano;

a pharmaceutically acceptable salt thereof, or a solvate or hydrate of said compound, or said salt.

28. The compound of claim 27 wherein $R^0$ and $R^1$ are each independently a phenyl substituted with 1 to 2 substituents independently selected from the group consisting of chloro, fluoro, ($C_1$–$C_4$)alkoxy, ($C_1$–$C_4$)alkyl, fluoro-substituted ($C_1$–$C_4$)alkyl, and cyano;

a pharmaceutically acceptable salt thereof, or a solvate or hydrate of said compound, or said salt.

29. The compound of claim 28 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

30. The compound of claim 19 wherein $R^0$ and $R^1$ are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano;

a pharmaceutically acceptable salt thereof, or a solvate or hydrate of said compound, or said salt.

31. The compound of claim 30 wherein $R^0$ and $R^1$ are each independently a phenyl substituted with 1 to 2 substituents independently selected from the group consisting of chloro, fluoro, ($C_1$–$C_4$)alkoxy, ($C_1$–$C_4$)alkyl, fluoro-substituted ($C_1$–$C_4$)alkyl), and cyano;

a pharmaceutically acceptable salt thereof, or a solvate or hydrate of said compound, or said salt.

32. The compound of claim 31 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

33. The compound of claim 21 wherein R0 and $R^1$ are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano;

a pharmaceutically acceptable salt thereof, or a solvate or hydrate of said compound, or said salt.

34. The compound of claim 30 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

35. The compound of claim 31 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4trifluoromethylphenyl, or 4-fluorophenyl;
a pharmaceutically acceptable salt thereof, or a solvate or hydrate of said compound, or said salt.

36. The compound of claim 2 wherein X is —N($R^{2a}$)—;
a pharmaceutically acceptable salt thereof, or a solvate or hydrate of said compound, or said salt.

37. The compound of claim 36 wherein $R^{2a}$ is hydrogen, $(C_1-C_4)$alkyl, fluoro-substituted $(C_1-C_4)$alkyl;
a pharmaceutically acceptable salt thereof, or a solvate or hydrate of said compound, or said salt.

38. The compound of claim 36 or 37 wherein $R^4$ is a chemical moiety selected from the group consisting of $(C_1-C_8)$alkyl, aryl$(C_1-C_4)$alkyl, 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

39. The compound of claim 36 or 37 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

40. The compound of claim 38 wherein $R^4$ is $(C_1-C_8)$alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

41. The compound of claim 39 wherein $R^4$ is $(C_1-C_8)$alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

42. The compound of claim 40 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

43. The compound of claim 41 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

44. The compound of claim 36 or 37 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

45. The compound of claim 44 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

46. The compound of claim 45 wherein $R^0$ is 2-chlorophenyl, 2-fluorophenyl, 2,4-dichlorophenyl, 2-fluoro-4-chlorophenyl, 2-chloro-4-fluorophenyl 2-methylphenyl or 2,4-difluorophenyl; and $R^1$ is 4-chlorophenyl, 4-cyanophenyl, 4-ethylphenyl 4-isopropylphenyl, 4-ethoxyphenyl, 4-isopropoxyphenyl, 4-trifluoromethylphenyl, or 4-fluorophenyl.
a pharmaceutically acceptable salt thereof, or a solvate or hydrate of said compound, or said salt.

47. The compound of claim 38 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

48. The compound of claim 47 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

49. The compound of claim 48 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

50. The compound of claim 39 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

51. The compound of claim 50 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

52. The compound of claim 51 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

53. The compound of claim 41 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

54. The compound of claim 53 wherein $R^0$ and $R^1$ are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;

a pharmaceutically acceptable salt thereof, or a solvate or hydrate of said compound, or said salt.

55. The compound of claim 54 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

56. The compound of claim 55 selected from the group consisting of 3-(4-chlorophenyl)-2-(2-chlorophenyl)-7-(2,2,2-trifluoroethyl)-4,5,6,7-tetrahydro-2H-pyrazolo[4,3-e][1,4]diazepin-8-one;

1-(4-chlorophenyl)-2-(2-chlorophenyl)-5,6,7,7a,8,9-hexahydro-2H-2,3,4a,9-tetra-azacyclopenta[f]azulen-4-one;

3-(4-chlorophenyl)-2-(2-chlorophenyl)-7-(2,2,2-trifluoroethyl)-4,5,6,7-tetrahydro-2H-pyrazolo[4,3-e][1,4]diazepin-8-one;

3-(4-chlorophenyl)-2-(2-chlorophenyl)-6,6-dimethyl-7-(2,2,2-trifluoroethyl)-4,5,6,7-tetrahydro-2H-pyrazolo[4,3-e][1,4]diazepin-8-one;

2-(2-chlorophenyl)-1-(4-chlorophenyl)-2,5,6,7,8,8a,9,10-octahydro-2,3,4a, 10-tetra-azabenzo[f]azulen-4-one;

3-(4-chlorophenyl)-2-(2-chlorophenyl)-4,6,6-trimethyl-7-(2,2,2-trifluoroethyl)4,5,6,7-tetrahydro-2H-pyrazolo[4,3-e][1,4]diazepin-8-one;

2-(2-chlorophenyl)-1-(4-chlorophenyl)-9-methyl-5,6,7,7a,8,9-hexahydro-2H2,3,4a,9-tetraazacyclopenta[f]azulen-4-one; and 3-(4-chlorophenyl)-2-(2-chlorophenyl)-4-methyl-7-(2,2,2-trifluoroethyl)-4,5,6,7-tetrahydro-2H-pyrazolo[4,3-e][1,4]diazepin-8-one;

or a solvate or hydrate of said compound.

57. The compound of claim 2 wherein X is S, SO or $SO_2$;

a pharmaceutically acceptable salt thereof, or a solvate or hydrate of said compound, or said salt.

58. The compound of claim 57 wherein $R^4$ is a chemical moiety selected from the group consisting of $(C_1–C_8)$alkyl, aryl$(C_1–C_4)$alkyl, 3- to 8-membered partially or fully saturated carbocyclic ring(s), and 3- to 8-membered partially or fully saturated heterocycle, where said chemical moiety is optionally substituted with one or more substituents;

or $R^4$ taken together with either $R^{3a}$ or $R^{3b}$ forms a fully or partially saturated 5- to 6-membered heterocyclic ring, where said heterocyclic ring is optionally substituted with one or more substituents;

a pharmaceutically acceptable salt thereof, or a solvate or hydrate of said compound, or said salt.

59. The compound of claim 57 wherein $R^{3a}$ and $R^{3b}$ are each independently hydrogen, $(C_1–C_4)$alkyl, or fluoro-substituted $(C_1–C_4)$alkyl;

a pharmaceutically acceptable salt thereof, or a solvate or hydrate of said compound, or said salt.

60. The compound of claim 58 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;

a pharmaceutically acceptable salt thereof, or a solvate or hydrate of said compound, or said salt.

61. The compound of claim 59 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;

a pharmaceutically acceptable salt thereof, or a solvate or hydrate of said compound, or said salt.

62. The compound of claim 60 wherein $R^4$ is ethyl, isopropyl, 2,2,2-trifluoroethyl, 2,2-difluoropropyl or 2,2-difluorobutyl;

a pharmaceutically acceptable salt thereof, or a solvate or hydrate of said compound, or said salt.

63. The compound of claim 61 wherein $R^4$ is ethyl, isopropyl, 2,2,2-trifluoroethyl, 2,2-difluoropropyl or 2,2-difluorobutyl;

a pharmaceutically acceptable salt thereof, or a solvate or hydrate of said compound, or said salt.

64. The compound of claim 57, 58, 59, 60, 61, 62 or 63 wherein $R^0$ and $R^1$ are each independently a phenyl substituted with 1 to 3 substituents independently selected from the group consisting of halo, $(C_1–C_4)$alkyl, $(C_1–C_4)$alkyl, halo-substituted $(C_1–C_4)$alkyl, and cyano;

a pharmaceutically acceptable salt thereof, or a solvate or hydrate of said compound, or said salt.

65. The compound of claim 64 wherein $R^0$ and $R^1$ are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;

a pharmaceutically acceptable salt thereof, or a solvate or hydrate of said compound, or said salt.

66. The compound of claim 65 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

67. The compound of claim 66 selected from the group consisting of 3-(4-chlorophenyl)-2-(2-chlorophenyl)-7-(2,2,2-trifluoroethyl)-6,7-dihydro-2H,5H-4-thia-1,2,7-triaza-azulen-8-one;

3-(4-chlorophenyl)-2-(2-chlorophenyl)-4-oxo-7-(2,2,2-trifluoroethyl)-4,5,6,7-tetrahydro-2H-4$\lambda^4$-thia-1,2,7,-triaza-azulen-8-one;

3-(4-chlorophenyl)-2-(2-chlorophenyl)-4,4-dioxo-7-(2,2,2-trifluoroethyl)-4,5,6,7-tetrahydro-2H-4$\lambda^4$-thia-1,2,7-triaza-azulen-8-one; and 3-(4-chlorophenyl)-2-(2-chlorophenyl)-6,6-dimethyl-7-(2,2,2-trifluoroethyl)-6,7-dihydro-2H,5H-4-thia-1,2,7-triaza-azulen-8-one;

or a solvate or hydrate of said compound.

68. The compound of claim 1 wherein A is carbon and B is nitrogen;

a pharmaceutically acceptable salt thereof, or a solvate or hydrate of said compound, or said salt.

69. The compound of claim 68 wherein X is oxygen;

a pharmaceutically acceptable salt thereof, or a solvate or hydrate of said compound, or said salt.

70. The compound of claim 69 wherein $R^{3a}$ and $R^{3b}$ are each independently hydrogen, $(C_1–C_4)$alkyl, or fluoro-substituted $(C_1–C_4)$alkyl;

a pharmaceutically acceptable salt thereof, or a solvate or hydrate of said compound, or said salt.

71. The compound of claim 69 wherein $R^4$ is a chemical moiety selected from the group consisting of $(C_1–C_8)$alkyl, aryl$(C_1–C_4)$alkyl, and 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

72. The compound of claim 70 wherein $R^4$ is $(C_1-C_8)$ alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

73. The compound of claim 71 wherein $R^4$ is $(C_1-C_8)$ alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

74. The compound of claim 72 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

75. The compound of claim 73 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

76. The compound of claim 69, 70, 71, 72, 73, 74 or 75 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

77. The compound of claim 76 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

78. The compound of claim 77 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

79. The compound of claim 78 selected from the group consisting of
2-(2-chlorophenyl)-3-(4-chlorophenyl)-7-(2,2,2-trifluoroethyl)-6,7-dihydro-3H,5H-5H-4-oxa-1,3,7-triaza-azulen-8-one;
2-(2-chlorophenyl)-3-(4-chlorophenyl)-7-(2,2-difluoropropyl)-6,7-dihydro-3H,5H-4-oxa-1,3,7-triaza-azulen-8-one; and
3-(4-chlorophenyl)-2-(2-chlorophenyl)-6,6-dimethyl-7-(2,2,2-trifluoroethyl)-6,7-dihydro-2H,5H-4-oxa-1,2,7-triaza-azulen-8-one;
or a solvate or hydrate of said compound.

80. The compound of claim 68 where X is —C($R^{2b}$)($R^{2c}$)—;
a pharmaceutically acceptable salt thereof, or a solvate or hydrate of said compound, or said salt.

81. The compound of claim 80 wherein at least one of $R^{2b}$ or $R^{2c}$ is $(C_1-C_4)$alkyl, or fluoro-substituted $(C_1-C_4)$alkyl;
a pharmaceutically acceptable salt thereof, or a solvate or hydrate of said compound, or said salt.

82. The compound of claim 80 wherein both $R^{2b}$ and $R^{2c}$ are hydrogen;
a pharmaceutically acceptable salt thereof, or a solvate or hydrate of said compound, or said salt.

83. The compound of claim 80, 81 or 82 wherein $R^4$ is a chemical moiety selected from the group consisting of $(C_1-C_8)$alkyl, aryl$(C_1-C_4)$alkyl, and 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

84. The compound of claim 80, 81 or 82 wherein $R^{3a}$ and $R^{3b}$ are each independently, $(C_1-C_4)$alkyl, or fluoro-substituted $(C_1-C_4)$alkyl.

85. The compound of claim 83 wherein $R^4$ is $(C_1-C_8)$ alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

86. The compound of claim 84 wherein $R^4$ is $(C_1-C_8)$ alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

87. The compound of claim 85 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

88. The compound of claim 86 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

89. The compound of claim 80, 81 or 82 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

90. The compound of claim 89 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

91. The compound of claim 90 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

92. The compound of claim 83 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

93. The compound of claim 92 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl, and cyano;
a pharmaceutically acceptable salt thereof, or a solvate or hydrate of said compound, or said salt.

94. The compound of claim 93 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

95. The compound of claim 84 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

96. The compound of claim 95 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

97. The compound of claim 96 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl or 4-fluorophenyl;
a pharmaceutically acceptable salt thereof, or a solvate or hydrate of said compound, or said salt.

98. The compound of claim 86 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

99. The compound of claim 98 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

100. The compound of claim 99 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

101. The compound of claim 68 wherein X is —N($R^{2a}$)—;
a pharmaceutically acceptable salt thereof, or a solvate or hydrate of said compound, or said salt.

102. The compound of claim 101 wherein $R^{2a}$ is hydrogen, $(C_1-C_4)$alkyl, fluoro-substituted $(C_1-C_4)$alkyl;
a pharmaceutically acceptable salt thereof, or a solvate or hydrate of said compound, or said salt.

103. The compound of claim 101 or 102 wherein $R^4$ is a chemical moiety selected from the group consisting of $(C_1-C_8)$alkyl, aryl$(C_1-C_4)$alkyl, and 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

104. The compound of claim 101 or 102 wherein $R^{3a}$ or $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

105. The compound of claim 103 wherein $R^4$ is $(C_1-C_8)$alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

106. The compound of claim 104 wherein $R^4$ is $(C_1-C_8)$alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

107. The compound of claim 105 wherein $R^4$ is ethyl, isopropyl, 2,2,2-trifluoroethyl, 2,2-difluoropropyl: or 2,2-difluorobutyl;
a pharmaceutically acceptable salt thereof, or a solvate or hydrate of said compound, or said salt.

108. The compound of claim 106 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

109. The compound of claim 101 or 102 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof, or a solvate or hydrate of said compound, or said salt.

110. The compound of claim 109 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof, or a solvate or hydrate of said compound, or said salt.

111. The compound of claim 110 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

112. The compound of claim 103 wherein $R^0$ and $R^1$ are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl, and cyano;
a pharmaceutically acceptable salt thereof, or a solvate or hydrate of said compound, or said salt.

113. The compound of claim 112 wherein $R^0$ and $R^1$ are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;
a pharmaceutically acceptable salt thereof, or a solvate or hydrate of said compound, or said salt.

114. The compound of claim 113 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

115. The compound of claim 104 wherein $R^0$ and $R^1$ are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl), and cyano;
a pharmaceutically acceptable salt thereof, or a solvate or hydrate of said compound, or said salt.

116. The compound of claim 115 wherein $R^0$ and $R^1$ are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;
a pharmaceutically acceptable salt thereof, or a solvate or hydrate of said compound, or said salt.

117. The compound of claim 116 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

118. The compound of claim 106 wherein $R^0$ and $R^1$ are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl, and cyano;
a pharmaceutically acceptable salt thereof, or a solvate or hydrate of said compound, or said salt.

119. The compound of claim 118 wherein $R^0$ and $R^1$ are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;
a pharmaceutically acceptable salt thereof, or a solvate or hydrate of said compound, or said salt.

120. The compound of claim 119 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;
a pharmaceutically acceptable salt thereof, or a solvate or hydrate of said compound, or said salt.

121. The compound of claim 120 selected from the group consisting of
3-(4-chlorophenyl)-2-(2-chlorophenyl)-7-(2,2,2-trifluoroethyl)-4,5,6,7-tetrahydro-3H-imidazo[4,5-e][1,4]diazepin-8-one;
3-(4-chlorophenyl)-2-(2-chlorophenyl)-4-methyl-7-(2,2,2-trifluoroethyl)-4,5,6,7-tetrahydro3H-imidazo[4,5-e][1,4]diazepin-8-one; and
3-(4-chlorophenyl)-2-(2-chlorophenyl)-4,6,6-trimethyl-7-(2,2,2-trifluoroethyl)-4,5,6,7-tetrahydro-3H-imidazo[4,5-e][1,4]diazepin-8-one;
or a solvate or hydrate of said compound.

122. The compound of claim 68 wherein X is S, SO, or $SO_2$;
a pharmaceutically acceptable salt thereof, or a solvate or hydrate of said compound, or said salt.

123. The compound of claim 122 wherein $R^4$ is a chemical moiety selected from the group consisting of $(C_1–C_8)$alkyl, aryl$(C_1–C_4)$alkyl, and 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

124. The compound of claim 122 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

125. The compound of claim 123 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

126. The compound of claim 124 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

127. The compound of claim 125 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

128. The compound of claim 126 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

129. The compound of claim 122, 123, 124, 125, 126, 127 or 128 wherein $R^0$ and $R^1$ are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl, and cyano;
a pharmaceutically acceptable salt thereof, or a solvate or hydrate of said compound, or said salt.

130. The compound of claim 129 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof, or a solvate or hydrate of said compound, or said salt.

131. The compound of claim 130 wherein $R^0$ is 2-chlorophenyl, 2-fluorophenyl, 2,4-dichlorophenyl, 2-fluoro-4-chlorophenyl, 2-chloro-4-fluorophenyl, 2-methylphenyl or 2,4-difluorophenyl; and $R^1$ is 4-chlorophenyl, 4-cyanophenyl, 4-ethylphenyl, 4-isopropylphenyl, 4-ethoxyphenyl, 4-isopropoxyphenyl, 4-trifluoromethylphenyl, or 4-fluorophenyl;

a pharmaceutically acceptable salt thereof, or a solvate or hydrate of said compound, or said salt.

132. The compound of claim 131 selected from the group consisting of
2-(2-chlorophenyl)-3-(4-chlorophenyl)-7-(2,2,2-trifluoroethyl)-6,7-dihydro-3H,5H-4-thia-1,3,7-triaza-azulen-8-one;
2-(2-chlorophenyl)-3-(4-chlorophenyl)-4-oxo-7-(2,2,2-trifluoroethyl)-4,5,6,7-tetrahydro-3H-4λ⁴-thia-1,3,7-triaza-azulen-8-one;
2-(2-chlorophenyl)-3-(4-chlorophenyl)-4,4-dioxo-7-(2,2,2-trifluoroethyl)-4,5,6,7-tetrahydro-3H-4λ⁴-thia-1,3,7-triaza-azulen-8-one; and
2-(2-chlorophenyl)-3-(4-chlorophenyl)6,6-dimethyl-7-(2,2,2-trifluoroethyl)-6,7-dihydro-3H,5H-4-thia-1,3,7-triaza-azulen-8-one;
or a solvate or hydrate of said compound.

133. A compound of Formula (II)

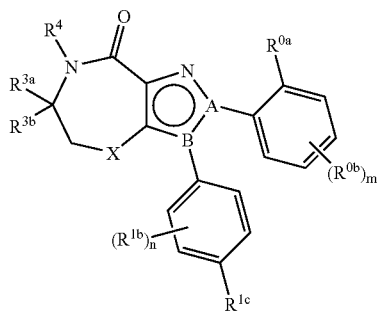

wherein
A is nitrogen and B is carbon, or A is carbon and B is nitrogen;
$R^{0a}$, $R^{0b}$, $R^{1b}$, and $R^{1c}$ are each independently halo, $(C_1-C_4)$alkoxy, $(C_1-C_4)$alkyl, halo-substituted $(C_1-C_4)$alkyl, or cyano;
n and m are each independently 0, 1 or 2;
X is O, S, SO, SO$_2$, —N($R^{2a}$)— or —C($R^{2b}$)($R^{2c}$)—, where $R^{2a}$, $R^{2b}$ and $R^{2c}$ are each independently hydrogen, $(C_1-C_4)$alkyl, halo-substituted $(C_1-C_4)$alkyl or $(C_1-C_5)$acyl;
$R^{3a}$ and $R^{3b}$ are each independently hydrogen, $(C_1-C_6)$alkyl, or halo-substituted $(C_1-C_6)$alkyl,
or either $R^{3a}$ or $R^{3b}$ taken together with $R^4$ forms a fully or partially saturated 5- to 6-membered heterocyclic ring, where the heterocyclic ring optionally contains an additional heteroatom selected from oxygen, nitrogen or sulfur and is optionally substituted with one or more substituents; and $R^4$ is a chemical moiety selected from the group consisting of $(C_1-C_8)$alkyl, aryl, heteroaryl, aryl$(C_1-C_4)$alkyl, a 3- to 8-membered partially or fully saturated carbocyclic ring(s), heteroaryl$(C_1-C_3)$alkyl, 5–6 membered lactone, 5- to 6-membered lactam, and a 3- to 8-membered partially or fully saturated heterocycle, where said chemical moiety is optionally substituted with one or more substituents, or $R^4$ taken together with either $R^{3a}$ or $R^{3b}$ forms a fully or partially saturated 5- to 6-membered heterocyclic ring, where the heterocyclic ring optionally contains an additional heteroatom selected from oxygen, nitrogen or sulfur and is optionally substituted with one or more substituents;

a pharmaceutically acceptable salt thereof, or a solvate or hydrate of said compound, or said salt.

134. The compound of claim 133 wherein A is nitrogen and B is carbon;
a pharmaceutically acceptable salt thereof, or a solvate or hydrate of said compound or said salt.

135. The compound of claim 133 wherein A is carbon and B is nitrogen;
a pharmaceutically acceptable salt thereof, or a solvate or hydrate of said compound or said salt.

136. The compound of claim 134 or 135 wherein X is oxygen;
a pharmaceutically acceptable salt thereof, or a solvate or hydrate of said compound or said salt.

137. The compound of claim 136 wherein $R^4$ is a chemical moiety selected from the group consisting of $(C_1-C_8)$alkyl, aryl$(C_1-C_4)$alkyl, 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

138. The compound of claim 137 wherein $R^4$ is $(C_1-C_8)$alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

139. The compound of claim 138 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

140. The compound of claim 136 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

141. The compound of claim 137 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

142. The compound of claim 138 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

143. The compound of claim 139 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

144. The compound of claim 134 or 135 wherein X is —N($R^{2a}$)—;
a pharmaceutically acceptable salt thereof, or a solvate or hydrate of said compound or said salt.

145. The compound of claim 144 wherein $R^{2a}$ is hydrogen, $(C_1–C_4)$alkyl, or fluoro-substituted $(C_1–C_4)$alkyl;
a pharmaceutically acceptable salt thereof, or a solvate or hydrate of said compound, or said salt.

146. The compound of claim 145 wherein $R^4$ is a chemical moiety selected from the group consisting of $(C_1–C_8)$alkyl, aryl$(C_1–C_4)$alkyl, 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

147. The compound of claim 146 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

148. The compound of claim 147 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

149. The compound of claim 144 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

150. The compound of claim 145 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

151. The compound of claim 146 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

152. The compound of claim 147 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

153. The compound of claim 148 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

154. The compound of claim 134 or 135 wherein X is —C($R^{2b}$)($R^{2c}$)—;
a pharmaceutically acceptable salt thereof, or a solvate or hydrate of said compound or said salt.

155. The compound of claim 154 wherein at least one of $R^{2b}$ or $R^{2c}$ is $(C_1–C_4)$alkyl, or fluoro-substituted $(C_1–C_4)$alkyl;
a pharmaceutically acceptable salt thereof, or a solvate or hydrate of said compound, or said salt.

156. The compound of claim 154 wherein $R^{2b}$ and $R^{2c}$ are both hydrogen;
a pharmaceutically acceptable salt thereof, or a solvate or hydrate of said compound, or said salt.

157. The compound of claim 155 wherein $R^4$ is a chemical moiety selected from the group consisting of $(C_1–C_8)$alkyl, aryl$(C_1–C_4)$alkyl, 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

158. The compound of claim 156 wherein $R^4$ is a chemical moiety selected from the group consisting of $(C_1–C_8)$alkyl, aryl$(C_1–C_4)$alkyl, 3- to 8-membered partially or fully saturated carbocyclic ring(s), and 3- to 3-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

159. The compound of claim 157 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

160. The compound of claim 158 wherein $R^4$ is $(C_1–C_8)$alkyl, fluoro-substituted $(C_1–C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

161. The compound of claim 159 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

162. The compound of claim 160 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

163. The compound of claim 154 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

164. The compound of claim 155 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

165. The compound of claim 156 wherein $R^{3a}$ and $R^{3b}$ are each independently hydrogen, $(C_1–C_4)$alkyl, or fluoro-substituted $(C_1–C_4)$alkyl;
a pharmaceutically acceptable salt thereof, or a solvate or hydrate of said compound, or said salt.

166. The compound of claim 157 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

167. The compound of claim 158 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

168. The compound of claim 159 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

169. The compound of claim 160 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

170. The compound of claim 161 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

171. The compound of claim 162 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

172. The compound of claim 134 or 135 wherein X is S, SO, or $SO_2$;
a pharmaceutically acceptable salt thereof, or a solvate or hydrate of said compound, or said salt.

173. The compound of claim 172 wherein $R^4$ is a chemical moiety selected from the group consisting of $(C_1-C_8)$alkyl, aryl$(C_1-C_4)$alkyl, 3- to 8-membered partially or fully saturated carbocyclic ring(s), and 3- to 8-membered partially or fully saturated heterocycle, where said chemical moiety is optionally substituted with one or more substituents;
or $R^4$ taken together with either $R^{3a}$ or $R^{3b}$ forms a fully or partially saturated 5- to 6-membered heterocyclic ring, where said heterocyclic ring is optionally substituted with one or more substituents;
a pharmaceutically acceptable salt thereof, or a solvate or hydrate of said compound, or said salt.

174. The compound of claim 173 wherein $R^4$ is $(C_1-C_8)$alkyl, fluoro-substituted $(C_1-C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound, or said salt.

175. The compound of claim 174 wherein $R^4$ is ethyl, isopropyl, 2,2,2-trifluoroethyl, 2,2-difluoropropyl or 2,2-difluorobutyl;
a pharmaceutically acceptable salt thereof, or a solvate or hydrate of said compound, or said salt.

176. The compound of claim 172 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

177. The compound of claim 173 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

178. The compound of claim 174 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

179. The compound of claim 175 wherein $R^{3a}$ and $R^{3b}$ are each independently hydrogen, $(C_1-C_4)$alkyl, or fluoro-substituted $(C_1-C_4)$alkyl;
a pharmaceutically acceptable salt thereof, or a solvate or hydrate of said compound, or said salt.

180. A pharmaceutical composition comprising (1) a compound of claim 1, a pharmaceutically acceptable salt thereof, or a solvate or hydrate of said compound or said salt; and (2) a pharmaceutically acceptable excipient, diluent, or carrier.

181. A method for treating a disease, condition or disorder which is modulated by a cannabinoid receptor antagonist in animals comprising the step of administering to an animal in need of such treatment a therapeutically effective amount of a compound of claim 1;
a pharmaceutically acceptable salt thereof, or a solvate or hydrate of said compound or said salt,
wherein said disease, condition or disorder modulated by a cannabinoid receptor antagonist is selected from the group consisting of weight loss, obesity, bulimia, alcoholism, or tobacco abuse.

182. A method for treating a disease, condition or disorder modulated by a cannabinoid receptor antagonist comprising the step of administering a pharmaceutical composition of claim 180, wherein said disease, condition or disorder modulated by a cannabinoid receptor antagonist is obesity, bulimia, alcoholism, or tobacco abuse.

* * * * *